US011000627B2

(12) United States Patent
Buchini et al.

(10) Patent No.: US 11,000,627 B2
(45) Date of Patent: May 11, 2021

(54) TREATMENT OF IMPLANTS WITH PHOSPHONIC ACID COMPOUNDS

(71) Applicant: Nano Bridging Molecules SA, Gland (CH)

(72) Inventors: Sabrina Buchini, St-George (CH); Richard Curno, St-George (CH); Björn-Owe Aronsson, Gland (CH); Péter Péchy, Lausanne (CH)

(73) Assignee: NANO BRIDGING MOLECULES SA, Gland (CH)

( * ) Notice: Subject to any disclaimer, the term of this patent is extended or adjusted under 35 U.S.C. 154(b) by 0 days.

(21) Appl. No.: 16/077,421

(22) PCT Filed: Feb. 13, 2017

(86) PCT No.: PCT/EP2017/053139
§ 371 (c)(1),
(2) Date: Aug. 10, 2018

(87) PCT Pub. No.: WO2017/137623
PCT Pub. Date: Aug. 17, 2017

(65) Prior Publication Data
US 2019/0038802 A1    Feb. 7, 2019

(30) Foreign Application Priority Data
Feb. 12, 2016   (EP) ..................... 16155497

(51) Int. Cl.
*A61L 27/32*    (2006.01)
*A61L 27/10*    (2006.01)
(Continued)

(52) U.S. Cl.
CPC ............ *A61L 27/32* (2013.01); *A61C 8/0013* (2013.01); *A61L 27/04* (2013.01); *A61L 27/045* (2013.01);
(Continued)

(58) Field of Classification Search
CPC .... A61C 8/00; B06B 1/02; B06B 3/00; A61L 27/32; A61L 27/50; A01N 57/20; C25D 11/26
See application file for complete search history.

(56) References Cited

U.S. PATENT DOCUMENTS

| | | | |
|---|---|---|---|
| 7,727,540 B2 * | 6/2010 | Descouts | C07F 9/3808 424/422 |
| 8,906,111 B2 * | 12/2014 | Tei | A61L 27/12 623/23.62 |
| 2002/0130441 A1 * | 9/2002 | Robinson | B06B 3/02 264/442 |

FOREIGN PATENT DOCUMENTS

| | | |
|---|---|---|
| EP | 1351722 | 10/2003 |
| EP | 2769741 | 8/2014 |

(Continued)

OTHER PUBLICATIONS

Extended European Search Report and Opinion issued in European Application 16155497.7, dated Jul. 27, 2016.
(Continued)

*Primary Examiner* — Dah-Wei D. Yuan
*Assistant Examiner* — Andrew J Bowman
(74) *Attorney, Agent, or Firm* — Parker Highlander PLLC

(57) ABSTRACT

The present invention relates to a process of treating an implant, comprising a step of treating the surface of the implant with at least one phosphonic acid compound or a pharmaceutically acceptable salt, ester or amide thereof under sonication at a temperature of about 50° C. to about 90° C. This process is highly advantageous in that it allows the formation of a monolayer of the phosphonic acid compound on the implant surface, having a particularly dense surface coverage which, in turn, results in an improved implant biocompatibility and improved osseointegration. The invention further relates to a surface-treated implant
(Continued)

Figure 1:
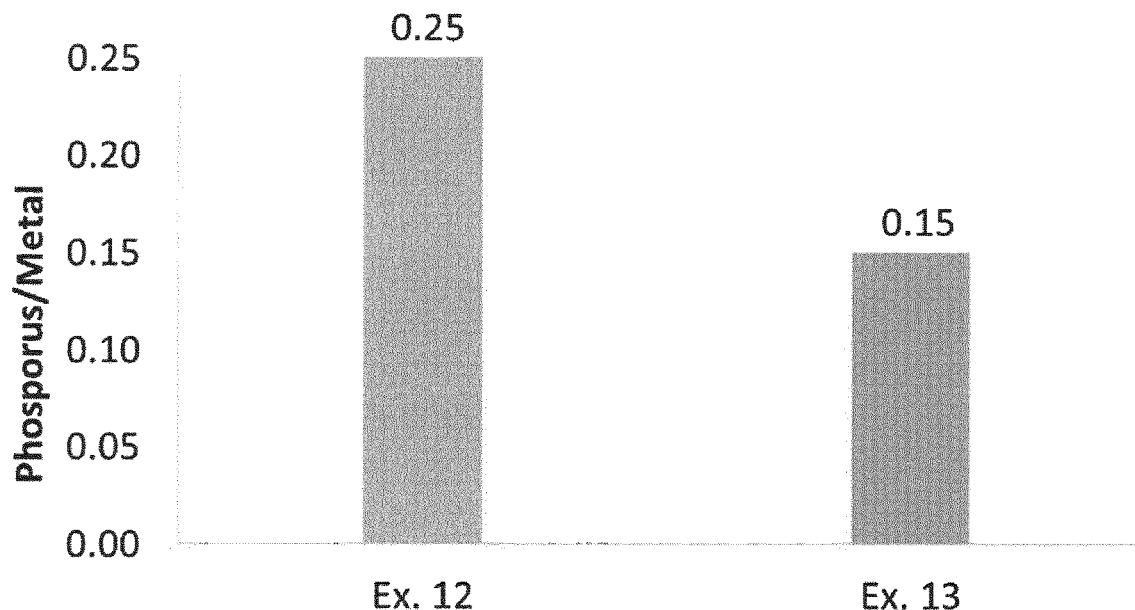

Example 14 obtainable by this process and, in particular, it provides an implant having a surface made of a metal, a metal alloy or a ceramic, wherein a phosphonic acid compound or a pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy (XPS), of at least 70% of a reference maximum surface coverage.

16 Claims, 3 Drawing Sheets

Specification includes a Sequence Listing.

(51) Int. Cl.
*A61L 27/54* (2006.01)
*A61L 31/02* (2006.01)
*A61L 27/50* (2006.01)
*A61L 31/16* (2006.01)
*A61L 31/08* (2006.01)
*A61L 31/14* (2006.01)
*A61L 27/04* (2006.01)
*A61L 27/28* (2006.01)
*A61C 8/00* (2006.01)
*A61L 27/06* (2006.01)

(52) U.S. Cl.
CPC .............. *A61L 27/047* (2013.01); *A61L 27/06* (2013.01); *A61L 27/10* (2013.01); *A61L 27/28* (2013.01); *A61L 27/50* (2013.01); *A61L 27/54* (2013.01); *A61L 31/022* (2013.01); *A61L 31/026* (2013.01); *A61L 31/08* (2013.01); *A61L 31/14* (2013.01); *A61L 31/16* (2013.01); *A61L 2300/20* (2013.01); *A61L 2300/216* (2013.01); *A61L 2420/02* (2013.01)

(56) References Cited

FOREIGN PATENT DOCUMENTS

| JP | 2010-162363 | 7/2010 |
|---|---|---|
| WO | WO 2014/048555 | 4/2014 |
| WO | WO 2014/128280 | 8/2014 |

OTHER PUBLICATIONS

PCT International Preliminary Report on Patentability issued in International Application No. PCT/EP2017/053139, dated Aug. 23, 2018.

PCT International Search Report and Written Opinion issued in International Application No. PCT/EP2017/053139, dated May 26, 2017.

Pinto et al., "Biodegradable chelating agents for industrial, domestic, and agricultural applications — a review," Environ Sci Pollut Res, 2014, 21; 11893-11906.

Roy et al. "Influence of modification time and high frequency ultrasound irradiation on self-assembling of alkylphosphonic acids on stainless steel: Electrochemical and spectroscopic studies," Ultrasonics Sonochemistry 28, 2016, 269-275.

* cited by examiner

Example 14

Example 15

Example 17

Example 20

Example 27

TREATMENT OF IMPLANTS WITH PHOSPHONIC ACID COMPOUNDS

This application is a national phase application under 35 U.S.C. § 371 of International Application No. PCT/EP2017/053139, filed Feb. 13, 2017, which claims benefit of European Application No. 16155497.7, filed Feb. 12, 2016, the entire contents of each of which are hereby incorporated by reference.

The present invention relates to a process of treating an implant, comprising a step of treating the surface of the implant with at least one phosphonic acid compound or a pharmaceutically acceptable salt, ester or amide thereof at a temperature of about 50° C. to about 90° C., preferably under sonication. This process is highly advantageous in that it allows the formation of a monolayer of the phosphonic acid compound on the implant surface, having a particularly dense surface coverage which, in turn, results in an improved implant biocompatibility and improved osseointegration. The invention further relates to a surface-treated implant obtainable by this process and, in particular, it provides an implant having a surface made of a metal, a metal alloy or a ceramic, wherein a phosphonic acid compound or a pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy (XPS), of at least 70% of a reference maximum surface coverage.

Poor implant biocompatibility and osseointegration can create serious problems for patients undergoing implant therapy. Implant loosening and failure due to lack of biocompatibility and osseointegration, can lead to revision surgeries and higher costs for the patient. One strategy to improve biocompatibility consists in making the implant surface appear as natural as possible to the surrounding tissues and thus enabling the natural interaction with biological fluids and molecules. It has been found that the treatment of implants with phosphonic acid compounds enhances implant biocompatibility and osseointegration. In particular, the treatment of implant surfaces with phosphonic acid compounds allows to achieve an improved biocompatibility by virtue of the hydrophilicity of the phosphonic acid groups and their resemblance to naturally occurring minerals, i.e. hydroxyapatite, which render the implant surface highly wettable and favor the interaction with biological molecules (Viornery C et al., Langmuir, 2002, 18, 2582-2589; Viornery C et al., J Biomed Mater Res, 2002, 62, 149-155; Gittens R A et al., Acta Biomater, 2014, 10(7), 2907-2918). Furthermore, the treatment of bone-anchored implants with phosphonic acid compounds has been demonstrated to render the surface osteoconductive, thereby enhancing osseointegration (von Salis-Soglio M et al., J Funct Biomater, 2014, 5(3), 135-157).

A process for treating the surface of endosseous implants with phosphonic acid compounds in order to enhance bone bonding strength and osseointegration has been described in detail in EP-A-1343545 and EP-A-1351722. Through this process, phosphonic acid compounds form a monolayer of molecules firmly bound to the implant surface. This is the result of a chemical reaction taking place between the phosphonic acid molecules and the oxide surface of metal, metal alloy and ceramic implants.

The surface treatment of implants with phosphonic acid compounds as taught in EP-A-1343545 has further been evaluated in pre-clinical and clinical studies. In particular, it has been shown that the surface treatment of dental implants with phosphonic acid compounds, forming a monolayer on the implant surface, improved osseointegration and maintained better marginal bone levels around the implants both in pre-clinical and clinical studies (von Salis-Soglio M et al., J Funct Biomater, 2014, 5(3), 135-157; Esposito M et al., Eur J Oral Implantol, 2013, 6(3), 227-236; Katsoulis J et al., Eur J Dental Implantol, 2014, 10(2), 70-72). The monolayer of phosphonic acid compounds bound to the surface of the implants used in these studies was obtained by applying the process described in EP-A-1343545.

While the clinical results obtained with the surface treatment of implants with phosphonic acid compounds as described in EP-A-1343545 and EP-A-1351722 are very encouraging, there is still an ongoing need for further improvement of implant biocompatibility and osseointegration.

EP-A-2769741 discloses specific implantable medical devices comprising a metallic substrate and a bisphosphonate, wherein both phosphorus atoms of the bisphosphonate are covalently attached to the same carbon atom. In these implantable medical devices, the bisphosphonate continuously coats the external surface of the metallic substrate as monolayer and as outermost layer. However, this document completely fails to teach or suggest the use of sonication in the treatment of the surface of the metallic substrate with the bisphosphonates, and it particularly fails to provide any hint or suggestion pointing to the advantageous effects resulting from the use of sonication together with an elevated temperature in this treatment step, as discussed and demonstrated further below.

WO 2014/048555 relates to certain dental implants or abutments comprising a ceramic body, the surface of which is covered with a phosphate layer. These implants or abutments are prepared by treating the ceramic body of the implant or abutment with an aqueous phosphate buffer solution, i.e. a solution containing a salt of phosphoric acid. However, none of the dental implants or abutments taught in this document are treated with any phosphonic acid compound. In the specific context of certain working examples disclosed in this document, the surface of the respective implants is cleaned with deconex 15 PF. This cleaning agent, deconex 15 PF, contains potassium hydroxide but it does not contain methylglycinediacetate (in contrast to deconex 15 PF-x).

In the context of the present invention, it has surprisingly been found that if the surface treatment of an implant with a phosphonic acid compound is conducted at an elevated temperature of about 50° C. to about 90° C., particularly at about 65° C. while using sonication, a more densely packed monolayer of the phosphonic acid compounds bound to the implant surface can be obtained. As also demonstrated in the appended examples, the implants thus treated exhibit an improved surface coverage with the phosphonic acid compounds, which is reflected by an increased amount of phosphonic acid compounds bound to the implant surface. The greater amount of phosphonic acid compounds bound to the implant surface, in turn, results in an improved implant biocompatibility and improved osseointegration.

The use of sonication in the surface treatment of the implant with the phosphonic acid compound at an elevated temperature results in the formation of an even more densely packed monolayer of the phosphonic acid compounds on the implant surface (see, in particular, Examples 22 to 24) and, consequently, allows to obtain a further improvement in biocompatibility and osseointegration of the implant thus treated.

Notably, the improved implant surface coverage with phosphonic acid compounds that is achieved by the process of the present invention is fundamentally different from the formation of multiple layers of phosphonic acid compounds on the implant surface through hydrogen bonding between the phosphonic acid compounds. Such a formation of multiple layers of phosphonic acid compounds, which typically occurs if high concentrations of phosphonic acid compounds are employed in previously known treatment processes as described in EP-A-1343545 and EP-A-1351722, does not increase the amount of phosphonic acid compounds that are directly bound to the implant surface, and is furthermore disadvantageous since the additional layers of phosphonic acid compounds are prone to flake off and can thus impair osseointegration. In contrast thereto, the surface treatment process of the present invention allows the formation of a densely packed monolayer of a phosphonic acid compound even at high concentrations of the phosphonic acid compound, which would otherwise result in the disadvantageous formation of multiple layers of the phosphonic acid compound when used in the previously known surface treatment processes.

An implant treated in accordance with the present invention, having a surface that is covered by a particularly dense monolayer of a phosphonic acid compound which enhances biocompatibility and osseointegration, is therefore highly advantageous over previously known implants treated with phosphonic acid compounds, which have an implant surface covered by a less densely packed monolayer of phosphonic acid compound, resulting in a less pronounced enhancement of biocompatibility and osseointegration, or an implant surface covered by multiple layers of phosphonic acid compound, which is disadvantageous in terms of stability and osseointegration.

The present invention thus solves the problem of providing an implant treated with a phosphonic acid compound, having an improved biocompatibility and osseointegration, as well as an improved process for the surface treatment of an implant with a phosphonic acid compound, allowing the production of a surface-treated implant having an enhanced biocompatibility and osseointegration.

Accordingly, in a first aspect, the present invention provides a process of treating an implant, the process comprising the following step:

treating the surface of the implant with at least one phosphonic acid compound or a pharmaceutically acceptable salt, ester or amide thereof at a temperature of about 50° C. to about 90° C.

In a second aspect, the invention provides a process of producing a surface-treated implant, comprising conducting the process of the first aspect of the invention to obtain the surface-treated implant.

In a third aspect, the present invention furthermore relates to an implant obtainable by the process of the first or the second aspect of the invention.

Moreover, in a fourth aspect, the invention relates an implant having a surface made of a metal, a metal alloy or a ceramic, wherein a phosphonic acid compound or a pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy (XPS), of at least 70% of a reference maximum surface coverage, wherein the reference maximum surface coverage refers to the surface coverage, in terms of the ratio of the phosphorus content to the metal content as determined by X-ray photoelectron spectroscopy, that is obtained if the implant is first pre-treated with a 2% (v/v) aqueous solution, having a pH greater than 12, of an alkaline phosphate-free liquid cleaning concentrate under sonication at a temperature of 65° C. for a period of 30 min, is then rinsed with water under sonication at a temperature of 65° C. until the used water after rinsing has a pH of 6.2±0.5, and is then treated with a 5 mM aqueous solution of the phosphonic acid compound or the pharmaceutically acceptable salt, ester or amide thereof under sonication at a temperature of 65° C. for a period of 60 min, wherein said liquid cleaning concentrate comprises 5% (w/w) to 15% (w/w) of methylglycinediacetate and 1% (w/w) to 5% (w/w) of potassium hydroxide and has a pH greater than 12. The implant according to this fourth aspect can be produced, e.g., by the process of the first or the second aspect of the invention.

The following description of general and preferred features and embodiments relates to each one of the processes and implants provided in the present specification, including in particular those according to the above-described first, second, third and fourth aspects of the invention, unless explicitly indicated otherwise.

The process according to the first or the second aspect of the invention comprises a step of treating the surface of an implant with at least one phosphonic acid compound or a pharmaceutically acceptable salt, ester or amide thereof at a temperature of about 50° C. to about 90° C. This step of treatment with the phosphonic acid compound is preferably conducted at a temperature of about 55° C. to about 75° C., more preferably at a temperature of about 60° C. to about 70° C., and even more preferably at a temperature of about 65° C. It is furthermore preferred that this step of treatment with the phosphonic acid compound is conducted under sonication.

The phosphonic acid compound (or the pharmaceutically acceptable salt, ester or amide thereof) is not particularly limited, as long as it comprises one or more phosphonic acid groups.

For example, the phosphonic acid compound may be a $C_{1-30}$ hydrocarbon which is substituted with 1 to 6 phosphonic acid groups, wherein said hydrocarbon is optionally substituted with one or more (e.g., one, two, three, or four) groups independently selected from hydroxy and halogen, and further wherein one or more (e.g., one, two, three, or four) carbon atoms comprised in said hydrocarbon are optionally each replaced by a heteroatom independently selected from nitrogen, oxygen and sulfur. Said hydrocarbon preferably has 1 to 15 carbon atoms, more preferably 1 to 10 carbon atoms, and even more preferably 2 to 6 carbon atoms. The hydrocarbon may saturated or unsaturated, and it is preferably saturated. Moreover, while the hydrocarbon may be composed of cyclic and/or acyclic hydrocarbon moieties, it is preferably an acyclic hydrocarbon (e.g., an alkane or an alkene, both of which may be linear or branched), and it is more preferably an alkane, particularly a linear alkane. While the hydrocarbon may further be substituted with one or more (e.g., one, two, or three) groups independently selected from hydroxy and halogen, and/or one or more (e.g., one or two) carbon atoms comprised in the hydrocarbon may each be replaced by a heteroatom independently selected from nitrogen, oxygen and sulfur, it is preferred that the hydrocarbon is not substituted with hydroxy or halogen and that none of its carbon atoms are replaced by heteroatoms. The hydrocarbon is substituted with 1, 2, 3, 4, 5 or 6 phosphonic acid groups, preferably with 3, 4, 5 or 6 phosphonic acid groups, more preferably with 3 or 4 phosphonic acid groups, and even more preferably with 4 phosphonic acid groups.

It is thus particularly preferred that the phosphonic acid compound is a $C_{1-15}$ hydrocarbon (particularly a $C_{1-15}$ alkane or a $C_{2-15}$ alkene) which is substituted with 1 to 6 phosphonic acid groups. More preferably, the phosphonic acid compound is a $C_{1-10}$ alkane (which may be linear or branched, and is preferably linear) which is substituted with 3 to 6 phosphonic acid groups. Even more preferably, the phosphonic acid compound is a linear $C_{2-6}$ alkane which is substituted with 3 or 4 phosphonic acid groups, particularly with 4 phosphonic acid groups.

Examples of such phosphonic acid compounds, particularly of a phosphonic acid compound which is an acyclic saturated linear hydrocarbon (e.g., a linear $C_{1-10}$ alkane) substituted with 1 to 6 phosphonic acid groups, include methanephosphonic acid, ethanephosphonic acid, propane-1-phosphonic acid, propane-2-phosphonic acid, methane-1,1-diphosphonic acid, ethane-1,1-diphosphonic acid, ethane-1,2-diphosphonic acid, propane-1,1-diphosphonic acid, propane-2,2-diphosphonic acid, propane-1,2-diphosphonic acid, propane-1,3-diphosphonic acid, ethane-1,1,11-triphosphonic acid, ethane-1,1,2-triphosphonic acid, propane-1,1,1-triphosphonic acid, propane-1,1,2-triphosphonic acid, propane-1,1,3-triphosphonic acid, propane-1,2,2-triphosphonic acid, propane-1,2,3-triphosphonic acid, butane-1,1,1-triphosphonic acid, butane-1,1,2-triphosphonic acid, butane-1,1,3-triphosphonic acid, butane-1,1,4-triphosphonic acid, butane-1,2,2-triphosphonic acid, butane-2,2,3-triphosphonic acid, butane-1,3,3-triphosphonic acid, butane-1,2,3-triphosphonic acid, butane-1,2,4-triphosphonic acid, pentane-1,1,5-triphosphonic acid, pentane-2,2,5-triphosphonic acid, hexane-1,1,6-triphosphonic acid, hexane-2,2,6-triphosphonic acid, propane-1,1,1,1,2-tetraphosphonic acid, propane-1,1,1,3-tetraphosphonic acid, propane-1,1,2,2-tetraphosphonic acid, propane-1,1,2,3-tetraphosphonic acid, propane-1,1,3,3-tetraphosphonic acid, propane-1,2,2,3-tetraphosphonic acid, butane-1,1,4,4-tetraphosphonic acid, pentane-1,1,5,5-tetraphosphonic acid, hexane-1,1,6,6-tetraphosphonic acid, heptane-1,4,4,7-tetraphosphonic acid, octane-1,4,4,8-tetraphosphonic acid, nonane-1,5,5,9-tetraphosphonic acid, pentane-1,1,3,5,5-pentaphosphonic acid, or pentane-1,1,2,4,5,5-hexaphosphonic acid. Most preferably, the phosphonic acid compound is propane-1,1,3,3-tetraphosphonic acid.

Moreover, examples of the phosphonic acid compound, particularly of a phosphonic acid compound which is an acyclic saturated branched hydrocarbon (e.g., a branched $C_{4-10}$ alkane) substituted with 1 to 6 phosphonic acid groups, include tert-butyl phosphonic acid, 2-methyl-propane-1,1,1-triphosphonic acid, 2-methyl-propane-1,1,3-triphosphonic acid, 2-(phosphono-methyl)-propane-1,3-diphosphonic acid, 2-methyl-propane-1,3,3-tetraphosphonic acid, 2-methyl-butane-1,1,1-triphosphonic acid, 3-methyl-butane-1,1,1-triphosphonic acid, 2-(phosphono-methyl)-propane-1,1-diphosphonic acid, 2-methyl-butane-1,1,3-triphosphonic acid, 2-methyl-butane-1,1,4-triphosphonic acid, 3-methyl-butane-2,2,4-triphosphonic acid, 3-methyl-butane-1,1,4-triphosphonic acid, 2-(phosphono-methyl)-butane-1,3-diphosphonic acid, 2-(phosphono-methyl)-butane-1,4-diphosphonic acid, 3-methyl-butane-1,1,2-triphosphonic acid, 2-methyl-butane-1,1,4,4-tetraphosphonic acid, 2-methyl-pentane-1,1,1-triphosphonic acid, 2-(phosphono-methyl)-pentane-1,1-diphosphonic acid, 2-methyl-pentane-1,1,3-triphosphonic acid, 2-methyl-pentane-1,1,4-triphosphonic acid, 2-methyl-pentane-1,1,5-triphosphonic acid, 2-methyl-pentane-1,3,3-triphosphonic acid, 4-methyl-pentane-2,2,5-triphosphonic acid, 4-methyl-pentane-1,1,5-triphosphonic acid, 2-(phosphono-methyl)-pentane-1,3-diphosphonic acid, 2-methyl-pentane-1,3,4-triphosphonic acid, 2-(phosphono-methyl)-pentane-1,4-diphosphonic acid, 2-(phosphono-methyl)-pentane-1,5-diphosphonic acid, 2-methyl-pentane-1,3,5-triphosphonic acid, 4-methyl-pentane-1,2,5-triphosphonic acid, 2-methyl-pentane-1,1,5,5-tetraphosphonic acid, 3-methyl-pentane-1,1,1-triphosphonic acid, 3-methyl-pentane-1,1,2-triphosphonic acid, 3-(phosphono-methyl)-pentane-1,1-diphosphonic acid, 3-methyl-pentane-1,1,5-triphosphonic acid, 3-(triphosphono-methyl)-pentane, 3-(phosphono-methyl)-pentane-1,5-diphosphonic acid, 3-methyl-pentane-2,2,5-triphosphonic acid, 2-methyl-hexane-1,1,1-triphosphonic acid, 2-(phosphono-methyl)-hexane-1,6-diphosphonic acid, 2-methyl-hexane-1,1,6,6-tetraphosphonic acid, 4-methyl-heptane-1,1,1-triphosphonic acid, 4-methyl-heptane-1,1,6,6-tetraphosphonic acid, 2-methyl-octane-1,1,1-triphosphonic acid, 2-methyl-octane-1,1,8,8-tetraphosphonic acid, 3-(bisphosphono-methyl)-butane-1,1,4,4-tetraphosphonic acid, or 3-(bisphosphono-methyl)-pentane-1,1,5,5-tetraphosphonic acid.

Another example of the phosphonic acid compound, particularly of a phosphonic acid compound which is an acyclic saturated branched hydrocarbon (e.g., a branched $C_{4-15}$ alkane) substituted with 1 to 6 phosphonic acid groups, wherein one or more (e.g., one, two, three, or four) carbon atoms comprised in said hydrocarbon are each replaced by a heteroatom independently selected from nitrogen, oxygen and sulfur, is the compound diethylenetriamine penta(methylene phosphonic acid).

Further examples of the phosphonic acid compound, particularly of a phosphonic acid compound which is an acyclic unsaturated hydrocarbon (e.g., a linear or branched $C_{2-10}$ alkene) substituted with 1 to 6 phosphonic acid groups, include vinyl phosphonic acid, 1-propene-3-phosphonic acid, 2-propene-3-phosphonic acid, 1-propene-2-phosphonic acid, ethene-1,1-diphosphonic acid, ethene-1,2-diphosphonic acid, 1-propene-1,1-diphosphonic acid, 1-propene-3,3-diphosphonic acid, 1-propene-1,2-diphosphonic acid, 1-propene-2,3-diphosphonic acid, 1-propene-1,3-diphosphonic acid, 1-ethene-1,1,2-triphosphonic acid, 1-propene-3,3,3-triphosphonic acid, 1-propene-1,1,2-triphosphonic acid, 1-propene-2,3,3-triphosphonic acid, 1-propene-1,1,3-triphosphonic acid, 1-propene-1,3,3-triphosphonic acid, 1-propene-1,2,3-triphosphonic acid, 1-butene-4,4,4-triphosphonic acid, 2-butene-4,4,4-triphosphonic acid, 1-butene-1,1,2-triphosphonic acid, 2-butene-3,4,4-triphosphonic acid, 1-butene-3,4,4-triphosphonic acid, 1-butene-1,1,3-triphosphonic acid, 2-butene-1,1,3-triphosphonic acid, 1-butene-2,4,4-triphosphonic acid, 1-butene-1,1,4-triphosphonic acid, 2-butene-1,1,4-triphosphonic acid, 1-butene-1,4,4-triphosphonic acid, 1-butene-3,3,4-triphosphonic acid, 1-butene-2,3,3-triphosphonic acid, 1-butene-1,3,3-triphosphonic acid, 1-butene-1,2,3-triphosphonic acid, 2-butene-2,3,4-triphosphonic acid, 1-butene-2,3,4-triphosphonic acid, 1-butene-1,2,4-triphosphonic acid, 2-butene-1,2,4-triphosphonic acid, 1-butene-1,3,4-triphosphonic acid, 2-pentene-1,1,5-triphosphonic acid, 2-pentene-1,5,5-triphosphonic acid, 1-pentene-1,5,5-triphosphonic acid, 2-pentene-1,4,4-triphosphonic acid, 1-pentene-1,4,4-triphosphonic acid, 1-hexene-1,1,6-triphosphonic acid, 2-hexene-1,1,6-triphosphonic acid, 3-hexene-1,1,6-triphosphonic acid, 2-hexene-1,6,6-triphosphonic acid, 1-hexene-1,6,6-triphosphonic acid, 1-hexene-1,5,5-triphosphonic acid, 2-hexene-1,5,5-triphosphonic acid, 3-hexene-2,2,6-triphosphonic acid, 1-propene-2,3,3,3- tetraphosphonic acid, 1-propene-1,3,3,3-tetraphosphonic acid, 1-propene-1,2,3,3-tetraphosphonic acid, 1-propene-1,1,3,3-tetraphosphonic acid, 1-butene-1,1,4,4-tetraphosphonic acid, 2-butene-1,1,4,4-tetraphosphonic acid, 1-pentene-1,1,5,5-tetraphosphonic acid, 2-pentene-1,1,5,5-tetraphosphonic acid, 1-hexene-1,1,6,6-tetraphosphonic acid, 2-hexene-1,1,6,6-tetraphosphonic acid, 3-hexene-1,1,6,6-tetraphosphonic acid, 1-heptene-1,4,4,7-tetraphosphonic acid, 2-heptene-1,4,4,7-tetraphosphonic acid, 1-octene-1,4,4,8-tetraphosphonic acid, 2-octene-1,4,4,8-tetraphosphonic acid, 3-octene-1,5,5,8-tetraphosphonic acid, 1-nonene-1,5,5,9-tetraphosphonic acid, 2-nonene-1,5,5,9-tetraphosphonic acid, or 3-nonene-1,5,5,9-tetraphosphonic acid.

Yet further examples of the phosphonic acid compound, particularly of a phosphonic acid compound which is a cyclic, saturated or unsaturated hydrocarbon (e.g., a $C_{3-7}$ cycloalkane, a $C_{3-7}$ cycloalkene, or a $C_{6-14}$ arene) substituted with 1 to 6 phosphonic acid groups, include 1-cyclopentyl-phosphonic acid, 1,1-cyclopentyl-diphosphonic acid, 1,2-cyclopentyl-diphosphonic acid, 1,3-cyclopentyl-diphosphonic acid, 1-cyclohexyl-phosphonic acid, 1,1-cyclohexyl-diphosphonic acid, 1,2-cyclohexyl-diphosphonic acid, 1,3-cyclohexyl-diphosphonic acid, 1,4-cyclohexyl-diphosphonic acid, or phenyl-1-phosphonic acid.

The phosphonic acid compound may also be a bisphosphonic acid, particularly a phosphonic acid compound comprising two phosphonic acid groups that are attached to the same carbon atom. Bisphosphonic acids form a well-known class of compounds and are further described, e.g., in: Fleisch H, Bisphosphonates in bone disease: from the laboratory to the patient, Academic press, 2000; or Russell R G et al., *Osteoporos Int.* 2008, 19(6), 733-759. Examples of such phosphonic acid compounds include, in particular, etidronic acid, clodronic acid, alendronic acid, tiludronic acid, neridronic acid, olpadronic acid, risedronic acid, pamidronic acid, ibandronic acid, zoledronic acid, incadronic acid, minodronic acid, or EB-1053.

The phosphonic acid compound may further be an amino acid which is substituted with 1 to 6 (i.e., 1, 2, 3, 4, 5 or 6; preferably 1, 2, 3, or 4; more preferably 1 or 2) phosphonic acid groups. The amino acid may be, e.g., any one of the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, or Val), or a non-proteinogenic and/or non-standard α-amino acid (such as, e.g., ornithine, citrulline, homolysine, pyrrolysine, 4-hydroxyproline, α-methylalanine (i.e., 2-aminoisobutyric acid), norvaline, norleucine, terleucine (i.e., tert-leucine), labionin, cyclopentylalanine, cyclohexylalanine, phenylalanine, naphthylalanine, pyridylalanine, thienylalanine, cyclohexylglycine, or phenylglycine), a β-amino acid (such as, e.g., β-alanine), a γ-amino acid (such as, e.g., γ-aminobutyric acid, isoglutamine, or statine) or a δ-amino acid. It is preferred that the amino acid is an α-amino acid (which may be the L-isomer or the D-isomer, and is preferably the L-isomer), more preferably one of the 20 standard proteinogenic α-amino acids (each of which may be the L-isomer or the D-isomer, and is preferably the L-isomer), and it is furthermore preferred that the phosphonic acid group(s) is/are attached to the side chain of the amino acid. Examples of such phosphonic acid compounds include 2-amino-3-phosphonopropionic acid and further compounds depicted in the following (each of which is preferably in the form of the respective L-isomer):

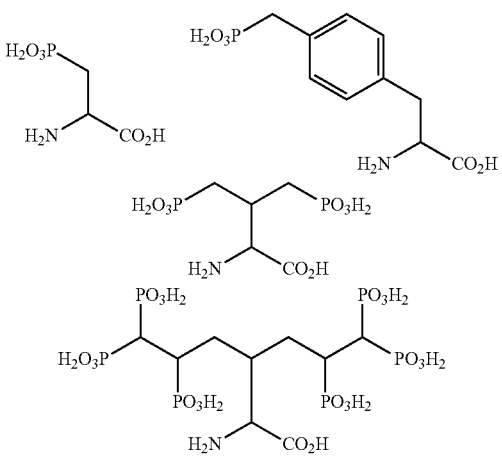

The phosphonic acid compound may also be a peptide of 2 to 15 amino acid residues, wherein the peptide is substituted with 1 to 6 (i.e., 1, 2, 3, 4, 5 or 6; preferably 3, 4, 5 or 6; more preferably 3 or 4) phosphonic acid groups. The amino acid residues comprised in the peptide are preferably selected from α-amino acids (which may each be present as the L-isomer or the D-isomer, and are preferably all present as the L-isomer), more preferably from the 20 standard proteinogenic α-amino acids (which may each be present as the L-isomer or the D-isomer, and are preferably all present as the L-isomer). It is furthermore preferred that the phosphonic acid group(s) is/are attached to the side chain of one or more of the amino acid residues comprised in the peptide.

Moreover, the phosphonic acid compound may be a peptide of 3 to 15 amino acid residues, wherein the peptide contains the amino acid sequence RGD (i.e., Arg-Gly-Asp), and wherein the peptide is substituted with 1 to 6 (i.e., 1, 2, 3, 4, 5 or 6; e.g., 3 or 4) phosphonic acid groups. The peptide containing the amino acid sequence RGD (also referred to as RGD-containing peptide) is preferably selected from RGD, GRGD, RGDE, RGDT, RGDS, GRGDS, GRGDSP, GRGDSPC, GRGDSPK, GRGDSC, RGDSPASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), and c(GRGDSP). The phosphonic acid group(s) is/are preferably attached to the side chain of one or more of the amino acid residues comprised in the RGD-containing peptide.

The phosphonic acid compound may likewise be a pharmaceutically active agent (e.g., a therapeutic drug), which is substituted with 1 to 6 (i.e., 1, 2, 3, 4, 5 or 6; e.g., 3 or 4) phosphonic acid groups. In particular, the phosphonic acid compound may be a statin, an analgesic, an antiinflammatory agent, or a vitamin D, each of which is substituted with 1 to 6 (i.e., 1, 2, 3, 4, 5 or 6; preferably 3 or 4) phosphonic acid groups. The vitamin D may be, e.g., vitamin D (preferably vitamin D3) in which one or more (preferably one) carbon atoms are substituted with a group —O—($C_{1-10}$ alkyl), and wherein the phosphonic acid group(s) is/are attached to the group(s) —O—($C_{1-10}$ alkyl). The vitamin D may also be, e.g., vitamin D (preferably vitamin D3) in which one or more (preferably one) carbon atoms are substituted with a group —O—CO—($C_{1-10}$ alkyl), and wherein the phosphonic acid group(s) is/are attached to the group(s) —O—CO—($C_{1-10}$ alkyl). The statin may be, e.g., simvastatin, lovastatin, or mevastatin, in each of which the —OH group attached to the oxooxane ring may be present as a group —O—CO—(C$_{1-10}$ alkyl), and wherein the phosphonic acid group(s) is/are attached to the group —O—CO—(C$_{1-10}$ alkyl). The statin may also be, e.g., a statin (e.g., simvastatin, lovastatin, mevastatin, or atorvastatin) in which one or more (preferably one) carbon atoms are substituted with a group —O—(C$_{1-10}$ alkyl), and wherein the phosphonic acid group(s) is/are attached to the group(s) —O—(C$_{1-10}$ alkyl). The statin may also be, e.g., a statin (e.g., simvastatin, lovastatin, mevastatin, or atorvastatin) in which one or more (preferably one) carbon atoms are substituted with a group —O—CO—(C$_{1-10}$ alkyl), and wherein the phosphonic acid group(s) is/are attached to the group(s) —O—CO—(C$_{1-10}$ alkyl). The phosphonic acid compound may further be aspirin or ibuprofen, each of which is substituted with 1 to 6 (i.e., 1, 2, 3, 4, 5 or 6; preferably, 1, 2, 3 or 4) phosphonic acid groups. The aspirin or the ibuprofen may be, e.g., aspirin or ibuprofen, in each of which one or more (e.g., one or two) hydrogen atoms are replaced by a C$_{1-10}$ alkyl group, and wherein the phosphonic acid group(s) is/are attached to the C$_{1-10}$ alkyl group(s).

Examples of phosphonic acid compounds comprising a vitamin D moiety are depicted in the following:

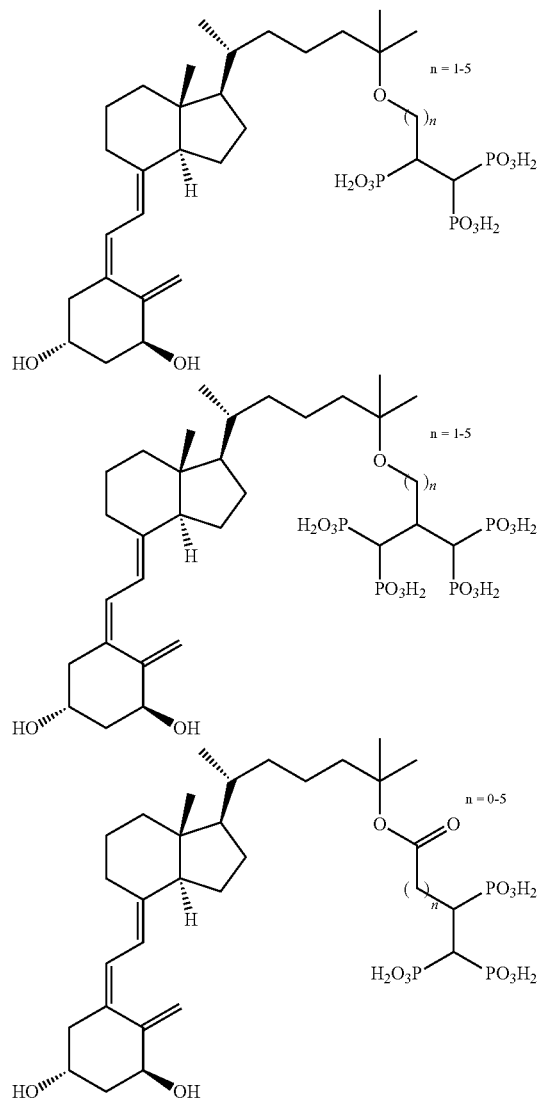

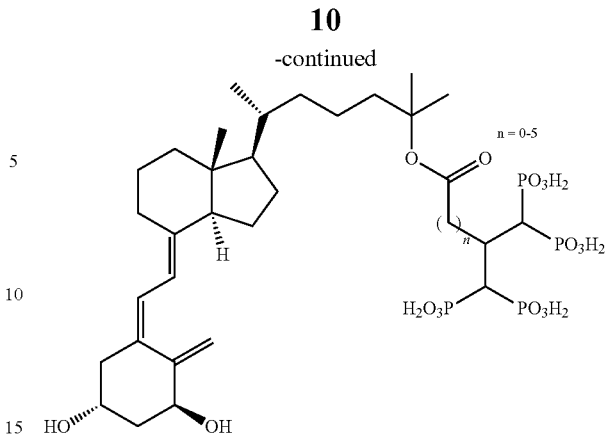

Examples of phosphonic acid compounds comprising a statin moiety are depicted in the following:

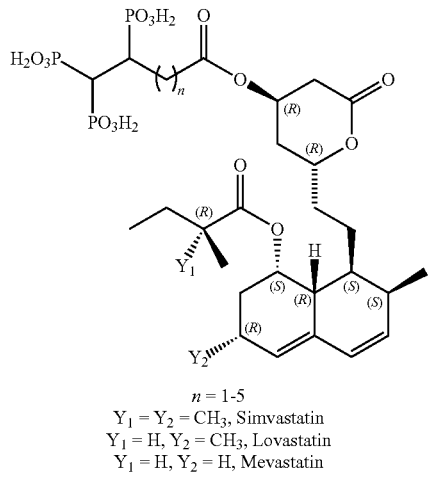

$n = 1-5$
$Y_1 = Y_2 = CH_3$, Simvastatin
$Y_1 = H, Y_2 = CH_3$, Lovastatin
$Y_1 = H, Y_2 = H$, Mevastatin

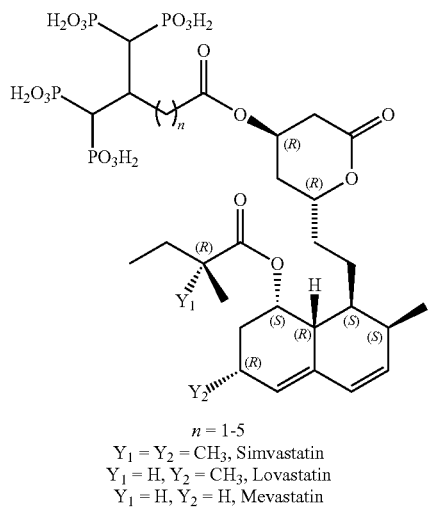

$n = 1-5$
$Y_1 = Y_2 = CH_3$, Simvastatin
$Y_1 = H, Y_2 = CH_3$, Lovastatin
$Y_1 = H, Y_2 = H$, Mevastatin Examples of phosphonic acid compounds comprising an aspirin moiety are depicted in the following (including, inter alia, 2-(2-phosphonoacetoxy)benzoic acid):

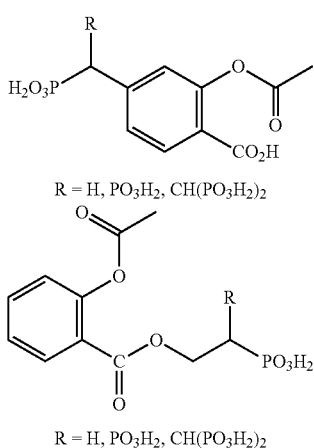

R = H, PO$_3$H$_2$, CH(PO$_3$H$_2$)$_2$

R = H, PO$_3$H$_2$, CH(PO$_3$H$_2$)$_2$

Examples of phosphonic acid compounds comprising an ibuprofen moiety are depicted in the following (wherein each R is independently selected from the indicated groups):

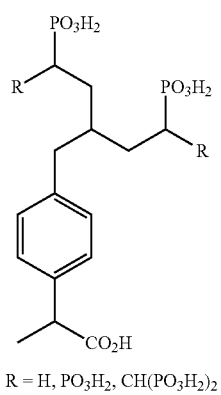

R = H, PO$_3$H$_2$, CH(PO$_3$H$_2$)$_2$

As explained above, the surface of the implant is treated with at least one phosphonic acid compound (including, e.g., any one of the specific phosphonic acid compounds described above) or a pharmaceutically acceptable salt, ester or amide thereof (e.g., of any one of the above-described specific phosphonic acid compounds).

The pharmaceutically acceptable salt of the phosphonic acid compound (e.g., of any one of the above-described specific phosphonic acid compounds) is not particularly limited and may be any pharmaceutically acceptable salt formed from one or more of the phosphonic acid groups of the phosphonic acid compound and a corresponding number of physiologically acceptable cations. Examples of such salts include, inter alia, alkali metal salts (e.g., sodium or potassium salts), alkaline earth metal salts (e.g., calcium or magnesium salts), zinc salts, ammonium salts, aliphatic amine salts (e.g., trimethylamine, triethylamine, dicyclohexylamine, ethanolamine, diethanolamine, triethanolamine, procaine, meglumine, ethylenediamine, or choline salts), aralkyl amine salts (e.g., N,N-dibenzylethylenediamine, benzathine, or benethamine salts), heterocyclic aromatic amine salts (e.g., pyridine, picoline, quinoline, or isoquinoline salts), quaternary ammonium salts (e.g., tetramethylammonium, tetraethylammonium, benzyltrimethylammonium, benzyltriethylammonium, benzyltributylammonium, methyltrioctylammonium, or tetrabutylammonium salts), or basic amino acid salts (e.g., arginine, lysine, or histidine salts).

Preferably, the pharmaceutically acceptable salt of the phosphonic acid compound (e.g., of any one of the above-described specific phosphonic acid compounds) is an alkali metal salt or an alkaline earth metal salt, more preferably a sodium salt, a potassium salt, a calcium salt, a magnesium salt, a strontium salt, or a technetium salt.

The pharmaceutically acceptable ester of the phosphonic acid compound (e.g., of any one of the above-described specific phosphonic acid compounds) is preferably an alkyl phosphonate, i.e., one or more (e.g., all) of the phosphonic acid groups of the compound are present in the form of a group —P(=O)(—OH)(—O-alkyl) or —P(=O)(—O-alkyl)(—O-alkyl). The alkyl phosphonate is more preferably a $C_{1-6}$ alkyl phosphonate. Even more preferably, the pharmaceutically acceptable ester of the phosphonic acid compound is a methyl ester, an ethyl ester, an n-propyl ester, an isopropyl ester, an n-butyl ester, a tert-butyl ester, an n-pentyl ester, or an n-hexyl ester.

The pharmaceutically acceptable amide of the phosphonic acid compound (e.g., of any one of the above-described specific phosphonic acid compounds) is preferably an N,N-dialkyl phosphonamidate, i.e., one or more (e.g., all) of the phosphonic acid groups of the compound are present in the form of a group —P(=O)(—OH)—N(alkyl)$_2$ or —P(=O)[—N(alkyl)$_2$]—N(alkyl)$_2$. The N,N-dialkyl phosphonamidate is more preferably an N,N-di($C_{1-6}$ alkyl) phosphonamidate. Even more preferably, the $C_{1-6}$ alkyl groups comprised in said N,N-di($C_{1-6}$ alkyl) phosphonamidate are selected from methyl, ethyl, n-propyl, isopropyl, n-butyl, tert-butyl, n-pentyl, and n-hexyl.

The pharmaceutically acceptable amide of the phosphonic acid compound (e.g., of any one of the above-described specific phosphonic acid compounds) may also be formed from the phosphonic acid compound and an amino acid or a peptide. In particular, one or more (e.g., all) of the phosphonic acid groups comprised in the phosphonic acid compound may form phosphonic acid amide groups (i.e., phosphonamidate groups) with an amino group comprised in the amino acid or with an amino group comprised in the peptide. Said peptide is preferably a peptide of 2 to 15 amino acid residues. The peptide may also be a peptide of 3 to 15 amino acid residues, wherein said peptide contains the amino acid sequence RGD. Examples of such an RGD-containing peptide include, in particular, RGD, GRGD, RGDE, RGDT, RGDS, GRGDS, GRGDSP, GRGDSPC, GRGDSPK, GRGDSC, RGDSPASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), or c(GRGDSP).

The phosphonic acid compound to be used in accordance with the present invention may exist in the form of different isomers, in particular stereoisomers (including, e.g., geometric isomers (or cis/trans isomers), enantiomers and diastereomers) or tautomers. All such isomers of the phosphonic acid compound are contemplated to be used in the present invention, either in admixture or in pure or substantially pure form. As for stereoisomers, the invention embraces the use of isolated optical isomers of the phosphonic acid compound as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active base, followed by crystallization. The present invention further encompasses the use of any tautomers of the phosphonic acid compound.

Moreover, the phosphonic acid compound can also be a phosphonic acid compound or a pharmaceutically acceptable salt thereof, as described and defined herein above, wherein each of its phosphonic acid groups may independently be in the form of a phosphonic acid ester group (forming a pharmaceutically acceptable ester; as further described herein above) or in the form of a phosphonic acid amide group (forming a pharmaceutically acceptable amide; as further described herein above).

It is preferred that the surface of the implant is treated with at least one phosphonic acid compound or a pharmaceutically acceptable salt thereof (including, e.g., any one of the above-described specific phosphonic acid compounds or salts; most preferably with propane-1,1,3,3-tetraphosphonic acid), rather than with an ester or an amide of a phosphonic acid compound.

It is furthermore preferred that the phosphonic acid compound or the pharmaceutically acceptable salt, ester or amide thereof (particularly the phosphonic acid compound or the pharmaceutically acceptable salt thereof) is employed at a concentration of about 0.1 mM to about 25 mM (i.e., about 0.1 mmol/L to about 25 mmol/L), more preferably at a concentration of about 0.5 mM to about 10 mM, even more preferably at a concentration of about 0.7 mM to about 7 mM, yet even more preferably at a concentration of about 1 mM to about 5 mM, for treating the implant surface. The use of such concentrations allows the formation of a particularly dense monolayer of the phosphonic acid compound on the implant surface.

While the use of high concentrations of phosphonic acid compounds (e.g., more than 1 mM) in previously known surface treatment processes, as described in EP-A-1343545 and EP-A-1351722, would typically result in the disadvantageous formation of multiple layers of phosphonic acid compounds, the process of the first or second aspect of the present invention prevents the formation of such multiple layers of phosphonic acid compounds on the implant surface. Without being bound by theory, the prevention of the formation of multiple layers of phosphonic acid compounds in the process of the invention results from a suppression of hydrogen bonding between the phosphonic acid compounds during the step of treating the implant surface with the phosphonic acid compound. The process of the present invention is thus highly advantageous as it allows the formation of a densely packed monolayer of phosphonic acid compounds even if high concentrations of phosphonic acid compounds are employed. Moreover, it is also advantageous that phosphonic acid compounds can be used in the process of the invention over a broad range of different concentrations, including at high concentrations, as this facilitates the conduction of the process and enhances its adaptability.

The duration (i.e., the incubation time) of the step of treatment with the phosphonic acid compound is not particularly limited and can be, e.g., about 5 min to about 120 min, preferably about 10 min to about 80 min, more preferably about 40 min to about 60 min.

The surface of the implant may be treated with only one phosphonic acid compound or a pharmaceutically acceptable salt, ester or amide thereof (i.e., with only a single type of compound), or it may be treated with two or more different phosphonic acid compounds or pharmaceutically acceptable salts, esters or amides thereof (i.e., with two or more different types of compounds). The treatment of the implant surface with only one type of compound is preferred.

In the step of treating the surface of the implant with at least one phosphonic acid compound or a pharmaceutically acceptable salt, ester or amide thereof at a temperature of about 50° C. to about 90° C., it is possible to treat the complete surface of the implant or only a part (e.g., a substantial part, such as 50% or more, preferably at least 70%, more preferably at least 80%, even more preferably at least 90%, still more preferably at least 95%) of the implant surface.

This can be accomplished, e.g., by subjecting the complete implant or only a part thereof to an aqueous composition (particularly an aqueous solution) comprising the phosphonic acid compound or the pharmaceutically acceptable salt, ester or amide thereof, or by subjecting the complete implant to an aqueous composition (as described above) while masking a part of the implant surface. It is preferred that substantially the complete surface of the implant, most preferably the complete surface, is treated with at least one phosphonic acid compound or a pharmaceutically acceptable salt, ester or amide thereof. The treatment of the implant surface with the phosphonic acid compound can be effected, e.g., by placing, dipping or immersing the implant in an aqueous composition (particularly an aqueous solution) of the corresponding phosphonic acid compound.

The process according to the first or the second aspect of the invention may further comprise, before the step of treatment with the phosphonic acid compound, a step of pre-treating the surface of the implant with a cleaning agent. This step of pre-treatment with a cleaning agent is preferably conducted at a temperature of about 50° C. to about 90° C., more preferably at a temperature of about 55° C. to about 75° C., even more preferably at a temperature of about 60° C. to about 70° C., and yet even more preferably at a temperature of about 65° C. It is furthermore preferred that the step of pre-treatment with the cleaning agent is conducted under sonication. Such a pre-treatment of the implant surface with a cleaning agent is advantageous as it facilitates the binding of the subsequently applied phosphonic acid compound(s) to the implant surface.

The cleaning agent to be used in the above-described pre-treatment step is not particularly limited and may be, e.g., potassium hydroxide, sodium hydroxide, or hydrogen peroxide. Preferably, the cleaning agent is (i) a phosphate-free alkaline cleaning agent, and/or (ii) comprises a chelating agent and an inorganic base. More preferably, the cleaning agent is a phosphate-free alkaline cleaning agent which comprises a chelating agent and an inorganic base. The chelating agent is preferably methylglycinediacetic acid (also known as MGDA or DL-alanine-N,N-diacetic acid) or a salt thereof (e.g., trisodium methylglycinediacetate). Moreover, the inorganic base is preferably potassium hydroxide and/or sodium hydroxide, more preferably potassium hydroxide.

It is particularly preferred that the cleaning agent is an aqueous solution of an alkaline phosphate-free liquid concentrate, wherein the liquid concentrate has a pH greater than 12 and comprises about 5% (w/w) to about 15% (w/w) of methylglycinediacetate and about 1% (w/w) to about 5% (w/w) of an inorganic base (which is preferably potassium hydroxide and/or sodium hydroxide, and is more preferably potassium hydroxide), and wherein the aqueous solution of the concentrate has a pH equal to or greater than 11. More preferably, said aqueous solution is a 0.5% (v/v) to 5% (v/v)

aqueous solution, even more preferably a 1% (v/v) to 3% (v/v) aqueous solution and still more preferably a 2% (v/v) aqueous solution, of the alkaline phosphate-free liquid concentrate. Accordingly, it is even more preferred that the cleaning agent is a 2% (v/v) aqueous solution of an alkaline phosphate-free liquid concentrate, wherein the liquid concentrate has a pH greater than 12 and comprises about 5% (w/w) to about 15% (w/w), e.g. about 10% (w/w), of methylglycinediacetate and about 1% (w/w) to about 5% (w/w), e.g. about 3% (w/w), of an inorganic base (which is preferably potassium hydroxide and/or sodium hydroxide, and is more preferably potassium hydroxide), and wherein said 2% (v/v) aqueous solution has a pH greater than 12. It is furthermore preferred that the aqueous solution of the alkaline phosphate-free liquid concentrate comprises at least about 70% (v/v) water, more preferably at least about 80% (v/v) water, even more preferably at least about 85% (v/v) water, even more preferably at least about 90% (v/v) water, and yet even more preferably at least about 95% (v/v) water, with respect to the total volume of the aqueous solution; most preferably, the aqueous solution of the alkaline phosphate-free liquid concentrate comprises only (i.e., consists of) water and the alkaline phosphate-free liquid concentrate.

The alkaline phosphate-free liquid concentrate comprises about 5% (w/w) to about 15% (w/w) of methylglycinediacetate and about 1% (w/w) to about 5% (w/w) of an inorganic base, preferably about 8% (w/w) to about 12% (w/w) of methylglycinediacetate and about 2% (w/w) to about 4% (w/w) of an inorganic base, and more preferably about 10% (w/w) of methylglycinediacetate and about 3% (w/w) of an inorganic base. The inorganic base is preferably potassium hydroxide and/or sodium hydroxide, and it is more preferably potassium hydroxide. The alkaline phosphate-free liquid concentrate may further comprise one or more surfactants, e.g., one or more amphoteric surfactants (e.g., less than 5% (w/w)) and/or one or more anionic surfactants (e.g., less than 5% (w/w)). An example of a corresponding alkaline phosphate-free liquid concentrate is deconex 15 PF-x (commercially available, e.g., from Borer Chemie AG, Zuchwil, Switzerland or from AppliChem GmbH, Darmstadt, Germany). Accordingly, it is particularly preferred that the cleaning agent is a 0.5% (v/v) to 5% (v/v) aqueous solution of deconex 15 PF-x, wherein said aqueous solution has a pH equal to or greater than 11, and it is even more preferred that the cleaning agent is a 2% (v/v) aqueous solution of deconex 15 PF-x, wherein said aqueous solution has a pH greater than 12. Such aqueous solutions of deconex 15 PF-x can be prepared, e.g., by diluting deconex 15 PF-x with water.

If a pre-treatment step with a cleaning agent is conducted (e.g., as further described herein above), the duration of this pre-treatment step is not particularly limited and can be, e.g., about 1 min to about 60 min, preferably about 1 min to about 30 min, more preferably about 2 min to about 15 min, even more preferably about 3 min to about 10 min (e.g., about 5 min).

It will be appreciated that in the process of the first or the second aspect of the present invention, the implant to be treated should preferably be rinsed with water after any step in which it is subjected to chemical agents. Thus, if a pre-treatment step with a cleaning agent is performed, it is preferred that the process further comprises, after the step of pre-treatment with the cleaning agent and before the step of treatment with the phosphonic acid compound, a first step of rinsing the surface of the implant with water. It is likewise preferred that the process further comprises, after the step of treatment with the phosphonic acid compound, a second step of rinsing the surface of the implant with water (this step is referred to as the "second" rinsing step, regardless of whether or not any other rinsing step has been carried out before). The first step and/or the second step of rinsing with water are each preferably conducted at a temperature of about 50° C. to about 90° C., more preferably at a temperature of about 55° C. to about 75° C., even more preferably at a temperature of about 60° C. to about 70° C., and still more preferably at a temperature of about 65° C. It is furthermore preferred that the first step and/or the second step of rinsing with water are each conducted under sonication. Moreover, it is preferred that the first step and/or the second step of rinsing with water are each repeated until the used water after rinsing has a pH of 6.2±0.5. If the first step and/or the second step of rinsing with water is/are repeated, it is advantageous that the respective rinsing step is conducted at least once at the above-described temperature and preferably under sonication, while any repetitions of the corresponding rinsing step can also vary with respect to temperature and the use of sonication (e.g., can also be conducted at room temperature and/or without sonication).

In accordance with the present invention, it is possible to conduct all steps of the process according to the first or the second aspect at a temperature of about 50° C. to about 90° C., preferably at a temperature of about 55° C. to about 75° C., more preferably at a temperature of about 60° C. to about 70° C., and even more preferably at a temperature of about 65° C. Furthermore, all steps of the respective process can be conducted under sonication.

The process according to the first or the second aspect of the invention thus preferably comprises the following steps (in the indicated order):
  pre-treating the surface of an implant with a cleaning agent;
  rinsing the surface of the implant with water;
  treating the surface of the implant with a phosphonic acid compound or a pharmaceutically acceptable salt, ester or amide thereof; and
  rinsing the surface of the implant with water;
  wherein all of the above-mentioned steps are conducted under sonication at a temperature of about 55° C. to about 75° C. Each of the above-mentioned steps is preferably conducted as described in detail herein above.

The implant of the present invention, i.e. the implant to be treated with a phosphonic acid compound in accordance with the first aspect, the implant to be produced in the process of the second aspect, and the implant of the third or fourth aspect of the invention, is not particularly limited and may be, e.g., a bone-anchored implant or a soft tissue-interfacing implant.

Both soft tissue-interfacing implants and bone-anchored implants can benefit from improved biocompatibility and/or osseointegration and, accordingly, the present invention relates to the treatment of implants of both of these types. Examples of soft tissue-interfacing implants include, inter alia, a dental abutment, or a stent (e.g., a coronary stent). Examples of bone-anchored implants include, inter alia, a dental implant, a hip implant (e.g., a hip stem, a hip ball, or a hip cap), a spinal implant (e.g., a spinal cage, a spinal disc, a spinal screw, or a pedical screw), a small joints implant, a shoulder implant, or a knee implant (e.g., a tibia plate or a femoral component).

Dental abutments are connectors placed on, or built into, the top of a dental implant, and on which a replacement tooth, fixed bridge or overdenture will be placed. Dental abutments are often made from titanium or titanium alloys or ceramic.

Coronary stents are expandable mesh-like tubes used to treat narrowed or diseased arteries. Stents are often made of metals, e.g. stainless steel, or of nickel-titanium alloys.

Dental implants include, e.g., endosseous dental implants to replace missing teeth (Brunette D M et al., Titanium in medicine, Springer, 2001). The most commonly used endosseous implants are root form analogs, such as straight or tapered screw-shaped cylinders, or custom-made root form dental implants. Commercially pure titanium and titanium alloys (e.g., Ti6Al4V) are the most common materials for dental implants. Furthermore, dental implants made of yttrium stabilized zirconia, zirconia and alumina alloys, titanium and zirconium alloys are becoming more common.

Hip implants are typically constituted of three components: stem, ball and cup. The hip stem can be made of metal or ceramic. The ball and cup can exist in multiple variations: metal-on-polyethylene, the ball is made of metal and the cup is made of polyethylene or has a plastic lining; ceramic-on-polyethylene, the ball is made of ceramic and the cup is made of polyethylene or has a plastic lining; metal-on-metal, the ball and cup are both made of metal; ceramic-on-ceramic, the ball is made of ceramic and the cup has a ceramic lining; ceramic-on-metal, the ball is made of ceramic and the cup has a metal lining.

Spinal implants are, e.g., pedicle screws, spinal cages or spinal discs: pedicle screws, often made of stainless steel or titanium or titanium alloys or cobalt-chrome or ceramics, provide means of gripping a spinal segment and act as firm anchor points that can be connected with a rod. Spinal cages are used in the disc space. The cages can be porous titanium or tantalum cylinders, enabling bone graft material to grow between vertebrae and through the cage.

Spinal discs, which can be made of cobalt chrome or a combination of cobalt chrome and polyethylene, act as a shock absorber between adjacent vertebrae and replace the natural discs that hold the distance between the vertebrae and maintain mobility of the spine. Small joints implants are implants intended for hand, finger, wrist, ankle or foot joints. There exist multiple design and material combinations (e.g., metal, ceramic and plastic).

Shoulder implants are typically constituted of three components: the stem, which can be made of roughened titanium or titanium alloys, the ball, which can be made of smooth titanium or titanium alloys or cobalt-chrome, and the socket, which can be made of a smooth plastic, cupped surface.

Knee implants are typically constituted of several components: femoral, tibial and patellar implants. The femoral implant can be made of a metal (e.g., titanium or cobalt-chromium based alloys), have a smooth surface and fit over the end of the femur. The tibial implant typically consists of two parts: a metal baseplate (e.g., titanium or cobalt-chromium based alloys), fitting over the tibia and an ultra-high molecular weight polyethylene surface attached to the baseplate, serving as a spacer between the baseplate and the metal implant that covers the end of the femur. Finally the implant that covers the back of the patella is typically made of ultra-high molecular weight polyethylene.

The implant may be, in particular, an endosseous implant, such as a dental endosseous implant. Moreover, the implant may have the form of, e.g., a screw, a plate, a nail, or a pin.

The surface of the implant can be made of any suitable material. In particular, the surface of the implant can be made of (or consist of) a metal, a metal alloy, or a ceramic.

If the surface of the implant is made of (or consists of) a metal or a metal alloy, it is preferred that said surface is made of (or consists of) titanium, chromium, niobium, tantalum, vanadium, zirconium, aluminum, cobalt, nickel, stainless steel, or an alloy of any of the aforementioned metals. More preferably, the surface of the implant is made of (or consists of) titanium or a titanium alloy, such as, e.g., grade 4 titanium, Ti-6Al-4V alloy (grade 5 titanium), Ti-6Al-4V ELI alloy (grade 23 titanium; preferably Ti-6Al-4V ELI as defined in the ASTM F136-13 standard, DOI: 10.1520/F0136), a titanium-niobium alloy, or a titanium-zirconium alloy. A further preferred metal alloy is cobalt-chromium; accordingly, the surface of the implant may also be made of (or consist of) a cobalt-chromium alloy.

If the surface of the implant is made of (or consists of) a ceramic, it is preferred that said ceramic is an oxide, a carbide, a nitride, an oxynitride, a carbonitride, or an oxycarbide of a metal or of a metal alloy (including, e.g., of any one of the specific metals or metal alloys mentioned herein above). In particular, said metal or metal alloy may be titanium, chromium, niobium, tantalum, vanadium, zirconium, aluminum, cobalt, nickel, stainless steel, or an alloy of any of these metals. Specific examples of preferred ceramics include titanium oxide, titanium carbide, titanium nitride, titanium oxynitride, titanium carbonitride, titanium oxycarbide, aluminum oxide, zirconium oxide, silicon oxide, aluminum oxide/zirconium oxide, or aluminum oxide/zirconium oxide/yttrium oxide. Accordingly, it is preferred that the surface of the implant is made of (or consists of) a ceramic selected from titanium oxide, titanium carbide, titanium nitride, titanium oxynitride, titanium carbonitride, and titanium oxycarbide. It is also preferred that the surface of the implant is made of (or consists of) a ceramic selected from aluminum oxide, zirconium oxide, silicon oxide, aluminum oxide/zirconium oxide, and aluminum oxide/zirconium oxide/yttrium oxide.

While the bulk of the implant can be made of the same material or of a different material than the implant surface, it is typically made of the same material. The entire implant may also be made of the same material as the implant surface. For the treatment with a phosphonic acid compound in accordance with the present invention, it is the material of the implant surface (e.g., to a depth of about 10 nm) that is particularly relevant.

The implant may further have any surface topology. Accordingly, the implant may have a smooth surface or a rough surface. The implant may also have a smooth surface topology on one or more parts of its surface (e.g. on one or more sides), and a rough surface topology on one or more other parts of its surface (e.g. on one or more other sides).

The process of treating an implant in accordance with the first aspect of the invention results in the production of a surface-treated implant. In accordance with the second aspect, the invention also relates to a process of producing a surface-treated implant, which may comprise the same steps as the process of the first aspect. The surface-treated implant thus obtained may further be placed in a packaging. The present invention also relates to the implant that is obtainable by the process of the first or the second aspect, including any of the preferred or exemplary embodiments of this process described herein above.

The implant according to the fourth aspect of the present invention is an implant having a surface made of a metal, a metal alloy or a ceramic, wherein a (i.e., at least one) phosphonic acid compound or a pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy (XPS), of at least 70% of a reference maximum surface coverage (which is defined further below).

This implant is highly advantageous as compared to previously known implants treated with phosphonic acid compounds since its surface is covered by a particularly dense monolayer of the phosphonic acid compound (or the pharmaceutically acceptable salt, ester or amide thereof), which results in an improved implant biocompatibility and improved osseointegration. In contrast thereto, previously known phosphonic acid compound-treated implants have an implant surface covered by a less densely packed monolayer of the phosphonic acid compound, resulting in a less pronounced improvement of biocompatibility and osseointegration, or have an implant surface covered by multiple layers of the phosphonic acid compound, which is disadvantageous since the additional layers of phosphonic acid compound can eventually flake off and can thus impair osseointegration. The implant according to the fourth aspect of the invention can be produced, e.g., using the process of the first or the second aspect of the present invention.

Preferably, the phosphonic acid compound (or the pharmaceutically acceptable salt, ester or amide thereof) is bound to the surface of the implant and forms a monolayer having an implant surface coverage, in terms of the ratio of the phosphorus content to the metal content as determined by X-ray photoelectron spectroscopy, of at least about 75% of the reference maximum surface coverage, more preferably at least about 80% of the reference maximum surface coverage, even more preferably at least about 85% of the reference maximum surface coverage, even more preferably at least about 90% of the reference maximum surface coverage, yet even more preferably at least about 95% of the reference maximum surface coverage, still more preferably at least about 98% of the reference maximum surface coverage, and most preferably at least about 99% of the reference maximum surface coverage.

The above-mentioned "reference maximum surface coverage" is a reference value which can be determined for any given implant to be treated with any given phosphonic acid compound. Specifically, the reference maximum surface coverage refers to the surface coverage, in terms of the ratio of the phosphorus content to the metal content as determined by X-ray photoelectron spectroscopy, that is obtained if the implant (i.e., a corresponding untreated implant) is first pre-treated with a 2% (v/v) aqueous solution, having a pH greater than 12, of an alkaline phosphate-free liquid cleaning concentrate under sonication at a temperature of 65° C. for a period of 30 min, is then rinsed with water under sonication at a temperature of 65° C. until the used water after rinsing has a pH of 6.2±0.5, and is then treated with a 5 mM aqueous solution of the phosphonic acid compound or the pharmaceutically acceptable salt, ester or amide thereof under sonication at a temperature of 65° C. for a period of 60 min, wherein said liquid cleaning concentrate comprises 5% (w/w) to 15% (w/w) of methylglycinediacetate and 1% (w/w) to 5% (w/w) of potassium hydroxide and has a pH greater than 12. Accordingly, the liquid cleaning concentrate may be, e.g., deconex 15 PF-x. The liquid cleaning concentrate preferably comprises (or, even more preferably, consists of) 10% (w/w) of methylglycinediacetate, 3% (w/w) of potassium hydroxide, and water, and has a pH greater than 12 (e.g., a pH ≥14). The 2% (v/v) aqueous solution can be prepared by mixing the alkaline phosphate-free liquid cleaning concentrate with water so as to obtain a 2% (v/v) solution of the cleaning concentrate. Likewise, the 5 mM aqueous solution of the phosphonic acid compound or the pharmaceutically acceptable salt, ester or amide thereof can be prepared by mixing the corresponding compound with water so as to obtain a 5 mM aqueous solution. The sonication is preferably carried out in an ultrasonic bath by applying ultrasound at a frequency of 30 kHz. It will be understood that the reference maximum surface coverage is a reference value which can be determined for any given implant and any given phosphonic acid compound (or a pharmaceutically acceptable salt, ester or amide thereof, or any given mixture of two or more such compounds) and, consequently, that it is to be determined using the same implant and the same phosphonic acid compound (or the same pharmaceutically acceptable salt, ester or amide thereof, or the same mixture of phosphonic acid compounds, salts, esters or amides) as in the case of the implant of interest, and that the same parts of the implant surface (preferably the entire implant surface) must be treated for the determination of this reference value as are treated in the case of the implant of interest. Furthermore, as the above-described maximum surface coverage is a reference value, it will be understood that the implants of the fourth aspect of the invention may also have an implant surface coverage with a monolayer of the respective phosphonic acid compound of more than 100% of the reference maximum surface coverage.

The ratio of the phosphorus content to the metal content is to be determined by X-ray photoelectron spectroscopy (XPS), both for establishing the surface coverage of the implant according to the fourth aspect with the respective phosphonic acid compound(s) and for establishing the corresponding reference maximum surface coverage for such an implant treated with such phosphonic acid compound(s). In XPS analysis, electrons in the test material are excited with X-rays so strongly that they leave their atom and eventually the sample surface. The kinetic energy of these photoelectrons can be analyzed with a hemispherical analyzer and hence their binding energy can be calculated. This permits to determine quantitatively the chemical composition as % atomic concentration (also referred to herein as "content") of each element in the top 5-10 nm of the surface. The area of analysis is typically 700 μm×700 μm. Survey spectra are typically recorded between 0 eV and 1200 eV binding energy.

A higher ratio of the phosphorus content to the metal content indicates that a greater amount of the corresponding phosphonic acid compound(s) is bound to the implant surface. The phosphorus (P) content is considered in relation to the metal content in order to exclude any possible interferences, e.g., from variations in the carbon content resulting from the presence (or absence) of organic contaminants on the implant surface (e.g., due to hydrocarbon absorption from the environment). The metal content to be determined by XPS corresponds to the total content of the metals comprised in the material of the implant surface. For example, in the case of an implant having a surface made of the titanium alloy Ti-6Al-4V ("grade 5 titanium"), the contents of titanium (Ti), aluminum (Al) and vanadium (V) can be added up in order to determine the metal content of the corresponding implant. Likewise, the contents of the following elements determined by XPS can be added up to determine the metal content of the corresponding implant: titanium for an implant having a surface made of titanium; iron, nickel and chromium for an implant having a surface made of stainless steel; cobalt, chromium and molybdenum for an implant having a surface made of cobalt chrome; zirconium and yttrium for an implant having a surface made of YZT zirconia (yttria stabilized zirconia); zirconium and aluminum for an implant having a surface made of a Biolox ceramic (CeramTec GmbH, Plochingen, Germany); zirconium and aluminum for an implant having a surface made of ATZ zirconia (alumina toughened zirconia); or zirconium, aluminum and yttrium for an implant having a surface made of alumina toughened zirconia, stabilized with yttria. It is preferred that the contents of (or at least of) the metals Mg, Al, Ti, V, Cr, Mn, Fe, Co, Ni, Zn, Sr, Y, Zr, Nb, Mo, Tc, Pd, Ag, Hf, Ta, Pt, and Au (more preferably the contents of the metals Mg, Al, Si, K, Ca, Ti, V, Cr, Mn, Fe, Co, Ni, Cu, Zn, Ga, Rb, Sr, Y, Zr, Nb, Mo, Tc, Ru, Rh, Pd, Ag, Cd, In, Sn, Sb, Hf, Ta, W, Pt, Au, and Pb) in the implant surface are determined by XPS. The contents of all those of the aforementioned metals that are present at a content greater than the measurement threshold can then be added up to establish the metal content of the implant. The XPS measurements can be conducted, e.g., as described in Example 8. XPS measurement procedures are further described, e.g., in: Chastain J & King R C (eds.), Handbook of X-ray photoelectron spectroscopy: a reference book of standard spectra for identification and interpretation of XPS data, Physical Electronics, Inc., Eden Prairie, Minn., USA, 1992; Crist B V, Handbooks of Monochromatic XPS Spectra, Volumes 1-5, XPS International, LLC, Mountain View, Calif., USA, 2004; Briggs D & Grant J T (eds.), Surface analysis by Auger and X-ray photoelectron spectroscopy, IM publications, 2003; or Watts J F, *Vacuum,* 1994, 45(6-7), 653-671.

The presence of a monolayer of the phosphonic acid compound or the pharmaceutically acceptable salt, ester or amide thereof on the surface of the implant can be verified using techniques known in the art. For example, the thickness of the layer of phosphonic acid compound on the implant surface can be measured using depth profiling by X-ray photoelectron spectroscopy (XPS). In particular, depth profiling by XPS typically involves combining sequences of ion gun sputtering cycles with XPS measurements, wherein an ion gun is used to etch the material for a defined period of time before being turned off, and XPS spectra are then acquired. Each sputtering cycle exposes a new surface, whose elemental composition can be analyzed by XPS. Such sputtering cycles followed by XPS measurements can be continued until the layer of phosphonic acid compound is removed, which is reflected by the disappearance of the phosphorus peak (P2p). If the thickness of the phosphonic acid compound layer thus measured corresponds to the size of one molecule of the corresponding phosphonic acid compound, it can be concluded that this layer is a monolayer (i.e., a monomolecular layer) of the phosphonic acid compound.

The further features of the implant according to the fourth aspect, including in particular the type of implant, the material of the implant surface, and the phosphonic acid compound (or the pharmaceutically acceptable salt, ester or amide thereof) bound to the implant surface, are preferably as described herein above in connection with the process of the first aspect of the invention.

The following definitions apply throughout the present specification, unless specifically indicated otherwise.

The term "sonication" refers to the application of sound energy to a sample, typically at a frequency equal to or greater than about 16 kHz (also referred to as "ultrasound"; e.g., from about 16 kHz to about 200 MHz, preferably from about 20 kHz to about 2 MHz, more preferably from about 25 kHz to about 200 kHz, even more preferably from about 30 kHz to about 100 kHz). Thus, if a process step is to be conducted "under sonication", the corresponding step shall carried out while applying sound at any of the above-described frequencies (e.g., in an ultrasonic bath).

The term "phosphonic acid group" refers to a group —P(=O)(—OH)$_2$ which is attached to a carbon atom of the remainder of the corresponding compound. It does, consequently, not refer to a phosphoric acid group, i.e., —O—P(=O)(—OH)$_2$. A "phosphonic acid compound" contains at least one group —P(=O)(—OH)$_2$ that is attached to a carbon atom of the compound.

The term "hydrocarbon" (or "hydrocarbon compound") refers to a compound consisting of carbon atoms and hydrogen atoms. A hydrocarbon may be saturated or unsaturated. It may further be acyclic (i.e., non-cyclic) or cyclic, or it may be composed of both acyclic and cyclic groups/subunits. An acyclic hydrocarbon or an acyclic group/subunit comprised in a hydrocarbon may be linear or branched. A "$C_{1-30}$ hydrocarbon" denotes a hydrocarbon having 1 to 30 carbon atoms. Exemplary hydrocarbon compounds include, inter alia, an alkane, an alkene, an alkyne, a cycloalkane, a cycloalkene, an arene, or a composite molecule composed of two or more of the aforementioned compounds (such as, e.g., an alkylcycloalkane, an alkylcycloalkene, an alkylarylalkene, an arylalkane, or an alkynylarene).

The term "hydrocarbon group" refers to a group consisting of carbon atoms and hydrogen atoms. A hydrocarbon group may be saturated or unsaturated. It may further be acyclic or cyclic, or it may be composed of both acyclic and cyclic groups/subunits. An acyclic hydrocarbon group or an acyclic subunit in a hydrocarbon group may be linear or branched. A "$C_{1-30}$ hydrocarbon group" denotes a hydrocarbon group having 1 to 30 carbon atoms. Exemplary hydrocarbon groups include, inter alia, alkyl, alkenyl, alkynyl, cycloalkyl, cycloalkenyl, aryl, or a composite group composed of two or more of the aforementioned groups (such as, e.g., alkylcycloalkyl, alkylcycloalkenyl, alkylarylalkenyl, arylalkyl, or alkynylaryl).

The term "alicyclic" is used in connection with cyclic groups and denotes that the corresponding cyclic group is non-aromatic.

The term "alkane" refers to a saturated acyclic hydrocarbon compound which may be linear or branched. Accordingly, an "alkane" does not comprise any carbon-to-carbon double bond or any carbon-to-carbon triple bond. A "$C_{1-5}$ alkane" denotes an alkane having 1 to 5 carbon atoms. Examples of an alkane include, inter alia, methane, ethane, propane (e.g., n-propane or isopropane), or butane (e.g., n-butane, isobutane, sec-butane, or tert-butane).

The term "alkyl" refers to a monovalent saturated acyclic hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Examples of an alkyl group include, inter alia, methyl, ethyl, propyl (e.g., n-propyl or isopropyl), or butyl (e.g., n-butyl, isobutyl, sec-butyl, or tert-butyl).

The term "alkene" refers to an unsaturated acyclic hydrocarbon compound which may be linear or branched and comprises one or more (e.g., one or two) carbon-to-carbon double bonds while it does not comprise any carbon-to-carbon triple bond. The term "$C_{2-5}$ alkene" denotes an alkene having 2 to 5 carbon atoms. Examples of an alkene include, inter alia, ethene, propene, butene, butadiene (e.g., buta-1,3-diene), pentene, or pentadiene (e.g., isoprene).

The term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Examples of an alkenyl group include, inter alia, ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl).

The term "alkyne" refers to an unsaturated acyclic hydrocarbon compound which may be linear or branched and comprises one or more (e.g., one or two) carbon-to-carbon triple bonds and optionally one or more carbon-to-carbon double bonds. The term "$C_{2-5}$ alkyne" denotes an alkyne having 2 to 5 carbon atoms. Examples of an alkyne include, inter alia, ethyne, propyne, or butyne.

The term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-5}$ alkynyl" denotes an alkynyl group having 2 to 5 carbon atoms. Examples of an alkynyl group include, inter alia, ethynyl, propynyl (e.g., propargyl), or butynyl.

The term "cycloalkane" refers to a saturated cyclic hydrocarbon compound, including monocyclic rings as well as bridged ring, spiro ring and/or fused ring systems (which may be composed, e.g., of two or three rings; such as, e.g., a fused ring system composed of two or three fused rings). A "cycloalkane" may, e.g., refer to cyclopropane, cyclobutane, cyclopentane, cyclohexane, cycloheptane, decalin (i.e., decahydronaphthalene), or adamantane. Unless defined otherwise, "cycloalkane" preferably refers to a $C_{3-11}$ cycloalkane, and more preferably refers to a $C_{3-7}$ cycloalkane.

The term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl.

The term "cycloalkene" refers to an unsaturated cyclic but non-aromatic hydrocarbon compound, including monocyclic rings as well as bridged ring, spiro ring and/or fused ring systems (which may be composed, e.g., of two or three rings; such as, e.g., a fused ring system composed of two or three fused rings), wherein said hydrocarbon compound comprises one or more (e.g., one or two) carbon-to-carbon double bonds and does not comprise any carbon-to-carbon triple bond. A "cycloalkene" may, e.g., refer to cyclopropene, cyclobutene, cyclopentene, cyclohexene, cyclohexadiene, cycloheptene, or cycloheptadiene. Unless defined otherwise, "cycloalkene" preferably refers to a $C_{3-11}$ cycloalkene, and more preferably refers to a $C_{3-7}$ cycloalkene.

The term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl.

The term "arene" refers to an aromatic cyclic hydrocarbon compound, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). An "arene" may, e.g., refer to benzene (i.e., $C_6H_6$), naphthalene, 1,2-dihydronaphthalene, 1,2,3,4-tetrahydronaphthalene, indane, indene, anthracene, phenanthrene, 9H-fluorene, or azulene. Unless defined otherwise, an "arene" preferably has 6 to 14 ring atoms, more preferably 6 to 10 ring atoms, even more preferably refers to benzene or naphthalene, and most preferably refers to benzene.

The term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

The term "halogen" (or "halogen group") refers to fluoro (—F), chloro (—Cl), bromo (—Br), or iodo (—I).

The term "amino acid" refers to a compound comprising at least one carboxylic acid group and at least one amino group. An "amino acid" may be an α-amino acid, particularly any one of the 20 standard proteinogenic α-amino acids (i.e., Ala, Arg, Asn, Asp, Cys, Glu, Gin, Gly, His, lie, Leu, Lys, Met, Phe, Pro, Ser, Thr, Trp, Tyr, and Val) but also a non-proteinogenic and/or non-standard α-amino acid (such as, e.g., ornithine, citrulline, homolysine, pyrrolysine, 4-hydroxyproline, α-methylalanine (i.e., 2-aminoisobutyric acid), norvaline, norleucine, terleucine (tert-leucine), labionin, or an alanine or glycine that is substituted at the side chain with a cyclic group (e.g., a cycloalkyl group, a heterocycloalkyl group, an aryl group, or a heteroaryl group) like, e.g., cyclopentylalanine, cyclohexylalanine, phenylalanine, naphthylalanine, pyridylalanine, thienylalanine, cyclohexylglycine, or phenylglycine), or a β-amino acid (e.g., β-alanine), a γ-amino acid (e.g., γ-aminobutyric acid, isoglutamine, or statine), or a δ-amino acid. Unless defined otherwise, it is preferred that the "amino acid" is an α-amino acid, more preferably it is any one of the 20 standard proteinogenic α-amino acids (preferably in the form of the L-isomer).

The term "peptide" refers to a polymer of two or more amino acids linked via amide bonds that are formed between an amino group of one amino acid and a carboxyl group of another amino acid. The amino acids comprised in the peptide, which are also referred to as amino acid residues, may be selected from the 20 standard proteinogenic α-amino acids (i.e., Ala, Arg, Asn, Asp, Cys, Glu, Gin, Gly, His, lie, Leu, Lys, Met, Phe, Pro, Ser, Thr, Trp, Tyr, and Val) but also from non-proteinogenic and/or non-standard α-amino acids (such as, e.g., ornithine, citrulline, homolysine, pyrrolysine, 4-hydroxyproline, α-methylalanine (i.e., 2-aminoisobutyric acid), norvaline, norleucine, terleucine (tert-leucine), labionin, or an alanine or glycine that is substituted at the side chain with a cyclic group (e.g., a cycloalkyl group, a heterocycloalkyl group, an aryl group, or a heteroaryl group)

like, e.g., cyclopentylalanine, cyclohexylalanine, phenylalanine, naphthylalanine, pyridylalanine, thienylalanine, cyclohexylglycine, or phenylglycine) as well as β-amino acids (e.g., β-alanine), γ-amino acids (e.g., γ-aminobutyric acid, isoglutamine, or statine) and δ-amino acids. Preferably, the amino acid residues comprised in the peptide are selected from α-amino acids, more preferably from the 20 standard proteinogenic α-amino acids (which can be present as the L-isomer or the D-isomer, and are preferably all present as the L-isomer). The peptide may be unmodified or may be modified, e.g., at its N-terminus, at its C-terminus and/or at a functional group in the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts PG & Greene T W, Greene's protective groups in organic synthesis, John Wiley & Sons, 2006. Such modifications may also include the covalent attachment of one or more polyethylene glycol (PEG) chains (forming a PEGylated peptide), the glycosylation and/or the acylation with one or more fatty acids (e.g., one or more $C_{8-30}$ alkanoic or alkenoic acids; forming a fatty acid acylated peptide). The amino acid residues comprised in the peptide may, e.g., be present as a linear molecular chain (forming a linear peptide) or may form one or more rings (corresponding to a cyclic peptide). The peptide may also form oligomers consisting of two or more identical or different molecules. Abbreviated designations of peptides are well-known in the art, such as, e.g., "c(RGDfK)" which refers to cyclo(Arg-Gly-Asp-(D-Phe)-Lys).

The term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group).

For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

The term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

The terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups and compounds are referred to as being "optionally substituted" in this specification. Generally, these groups or compounds may carry one or more substituents, such as, e.g., one, two, three or four substituents. It will be understood that the maximum number of substituents is limited by the number of attachment sites available on the substituted moiety. Unless defined otherwise, the "optionally substituted" groups or compounds referred to in this specification carry preferably not more than two substituents and may, in particular, carry only one substituent. Moreover, unless defined otherwise, it is preferred that the optional substituents are absent, i.e. that the corresponding groups or compounds are unsubstituted.

As used herein, unless explicitly indicated otherwise or contradicted by context, the terms "a", "an" and "the" are used interchangeably with "one or more" and "at least one". Thus, for example, an implant having "a" phosphonic acid compound bound to its surface can be interpreted as referring to an implant having "at least one" phosphonic acid compound (or "one or more" phosphonic acid compounds) bound to its surface.

The term "about" preferably refers to ±10% of the indicated numerical value, more preferably to ±5% of the indicated numerical value, and in particular to the exact numerical value indicated. If the term "about" is used in connection with the endpoints of a range, it preferably refers to the range from the lower endpoint −10% of its indicated numerical value to the upper endpoint +10% of its indicated numerical value, more preferably to the range from of the lower endpoint −5% to the upper endpoint +5%, and even more preferably to the range defined by the exact numerical values of the lower endpoint and the upper endpoint. If the term "about" is used in connection with the endpoint of an open-ended range, it preferably refers to the corresponding range starting from the lower endpoint −10% or from the upper endpoint +10%, more preferably to the range starting from the lower endpoint −5% or from the upper endpoint +5%, and even more preferably to the open-ended range defined by the exact numerical value of the corresponding endpoint.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

Unless specifically indicated otherwise, all properties and parameters referred to herein (including, e.g., any amounts/concentrations indicated in "% (v/v)" or in "mg/ml", as well as any pH values) are preferably to be determined at standard ambient temperature and pressure conditions, particularly at a temperature of 20° C. (293.15 K) and at an atmospheric pressure of 101.325 kPa (1 atm).

Moreover, unless indicated otherwise, any reference to an industry standard, a pharmacopeia, or a manufacturer's manual refers to the corresponding latest version that was available at the priority date (i.e., at the earliest filing date) of the present specification.

It is to be understood that the present invention specifically relates to each and every combination of features and embodiments described herein, including any combination of general and/or preferred features/embodiments.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention particularly relates to the following items:

1. A process of treating an implant, the process comprising the following step:
    treating the surface of the implant with at least one phosphonic acid compound or a pharmaceutically acceptable salt, ester or amide thereof at a temperature of about 50° C. to about 90° C.
2. The process of item 1, wherein the step of treatment with the phosphonic acid compound is conducted at a temperature of about 55° C. to about 75° C.
3. The process of item 1 or 2, wherein the step of treatment with the phosphonic acid compound is conducted at a temperature of about 60° C. to about 70° C.
4. The process of any one of items 1 to 3, wherein the step of treatment with the phosphonic acid compound is conducted at a temperature of about 65° C.
5. The process of any one of items 1 to 4, wherein the step of treatment with the phosphonic acid compound is conducted under sonication.

6. The process of any one of items 1 to 5, wherein the phosphonic acid compound is a $C_{1-30}$ hydrocarbon which is substituted with 1 to 6 phosphonic acid groups, wherein said hydrocarbon is optionally substituted with one or more groups independently selected from hydroxy and halogen, and further wherein one or more carbon atoms comprised in said hydrocarbon are optionally each replaced by a heteroatom independently selected from nitrogen, oxygen and sulfur.

7. The process of any one of items 1 to 6, wherein the phosphonic acid compound is a $C_{1-15}$ hydrocarbon which is substituted with 1 to 6 phosphonic acid groups.

8. The process of any one of items 1 to 7, wherein the phosphonic acid compound is a $C_{1-10}$ alkane which is substituted with 3 to 6 phosphonic acid groups.

9. The process of any one of items 1 to 8, wherein the phosphonic acid compound is a linear $C_{2-6}$ alkane which is substituted with 3 or 4 phosphonic acid groups.

10. The process of any one of items 1 to 6, wherein the phosphonic acid compound is methanephosphonic acid, ethanephosphonic acid, propane-1-phosphonic acid, propane-2-phosphonic acid, methane-1,1-diphosphonic acid, ethane-1,1-diphosphonic acid, ethane-1,2-diphosphonic acid, propane-1,1-diphosphonic acid, propane-2,2-diphosphonic acid, propane-1,2-diphosphonic acid, propane-1,1,3-diphosphonic acid, ethane-1,1,1-triphosphonic acid, ethane-1,1,2-triphosphonic acid, propane-1,1,1-triphosphonic acid, propane-1,1,2-triphosphonic acid, propane-1,2,3-triphosphonic acid, propane-1,2,2-triphosphonic acid, propane-1,2,3-triphosphonic acid, butane-1,1,1-triphosphonic acid, butane-1,1,2-triphosphonic acid, butane-1,1,3-triphosphonic acid, butane-1,1,4-triphosphonic acid, butane-1,2,2-triphosphonic acid, butane-2,2,3-triphosphonic acid, butane-1,3,3-triphosphonic acid, butane-1,2,3-triphosphonic acid, butane-1,2,4-triphosphonic acid, pentane-1,1,5-triphosphonic acid, pentane-2,2,5-triphosphonic acid, hexane-1,1,6-triphosphonic acid, hexane-2,2,6-triphosphonic acid, propane-1,1,1,2-tetraphosphonic acid, propane-1,1,1,3-tetraphosphonic acid, propane-1,1,2,2-tetraphosphonic acid, propane-1,1,2,3-tetraphosphonic acid, propane-1,1,3,3-tetraphosphonic acid, propane-1,2,2,3-tetraphosphonic acid, butane-1,1,4,4-tetraphosphonic acid, pentane-1,1,5,5-tetraphosphonic acid, hexane-1,1,1,6,6-tetraphosphonic acid, heptane-1,4,4,7-tetraphosphonic acid, octane-1,4,4,8-tetraphosphonic acid, nonane-1,5,5,9-tetraphosphonic acid, pentane-1,1,3,5,5-pentaphosphonic acid, or pentane-1,1,2,4,5,5-hexaphosphonic acid.

11. The process of any one of items 1 to 10, wherein the phosphonic acid compound is propane-1,1,3,3-tetraphosphonic acid.

12. The process of any one of items 1 to 6, wherein the phosphonic acid compound is tert-butyl phosphonic acid, 2-methyl-propane-1,1,1-triphosphonic acid, 2-methyl-propane-1,1,3-triphosphonic acid, 2-(phosphono-methyl)-propane-1,3-diphosphonic acid, 2-methyl-propane-1,1,3,3-tetraphosphonic acid, 2-methyl-butane-1,1,1-triphosphonic acid, 3-methyl-butane-1,1,1-triphosphonic acid, 2-(phosphono-methyl)-propane-1,1,1-diphosphonic acid, 2-methyl-butane-1,1,3-triphosphonic acid, 2-methyl-butane-1,1,4-triphosphonic acid, 3-methyl-butane-2,2,4-triphosphonic acid, 3-methyl-butane-1,1,4-triphosphonic acid, 2-(phosphono-methyl)-butane-1,3-diphosphonic acid, 2-(phosphono-methyl)-butane-1,4-diphosphonic acid, 3-methyl-butane-1,1,2-triphosphonic acid, 2-methyl-butane-1,1,4,4-tetraphosphonic acid, 2-methyl-pentane-1,1,1-triphosphonic acid, 2-(phosphono-methyl)-pentane-1,1-diphosphonic acid, 2-methyl-pentane-1,1,3-triphosphonic acid, 2-methyl-pentane-1,1,4-triphosphonic acid, 2-methyl-pentane-1,1,5-triphosphonic acid, 2-methyl-pentane-1,3,3-triphosphonic acid, 4-methyl-pentane-2,2,5-triphosphonic acid, 4-methyl-pentane-1,1,5-triphosphonic acid, 2-(phosphono-methyl)-pentane-1,3-diphosphonic acid, 2-methyl-pentane-1,3,4-triphosphonic acid, 2-(phosphono-methyl)-pentane-1,4-diphosphonic acid, 2-(phosphono-methyl)-pentane-1,5-diphosphonic acid, 2-methyl-pentane-1,3,5-triphosphonic acid, 4-methyl-pentane-1,2,5-triphosphonic acid, 2-methyl-pentane-1,1,5,5-tetraphosphonic acid, 3-methyl-pentane-1,1,1-triphosphonic acid, 3-methyl-pentane-1,1,2-triphosphonic acid, 3-(phosphono-methyl)-pentane-1,1-diphosphonic acid, 3-methyl-pentane-1,1,5-triphosphonic acid, 3-(triphosphono-methyl)-pentane, 3-(phosphono-methyl)-pentane-1,5-diphosphonic acid, 3-methyl-pentane-2,2,5-triphosphonic acid, 2-methyl-hexane-1,1,1-triphosphonic acid, 2-(phosphono-methyl)-hexane-1,6-diphosphonic acid, 2-methyl-hexane-1,1,6,6-tetraphosphonic acid, 4-methyl-heptane-1,1,1-triphosphonic acid, 4-methyl-heptane-1,1,6,6-tetraphosphonic acid, 2-methyl-octane-1,1,1-triphosphonic acid, 2-methyl-octane-1,1,8,8-tetraphosphonic acid, 3-(bisphosphono-methyl)-butane-1,1,4,4-tetraphosphonic acid, 3-(bisphosphono-methyl)-pentane-1,1,5,5-tetraphosphonic acid, or diethylenetriamine penta(methylene phosphonic acid).

13. The process of any one of items 1 to 6, wherein the phosphonic acid compound is vinyl phosphonic acid, 1-propene-3-phosphonic acid, 2-propene-3-phosphonic acid, 1-propene-2-phosphonic acid, ethene-1,1-diphosphonic acid, ethene-1,2-diphosphonic acid, 1-propene-1,1-diphosphonic acid, 1-propene-3,3-diphosphonic acid, 1-propene-1,2-diphosphonic acid, 1-propene-2,3-diphosphonic acid, 1-propene-1,3-diphosphonic acid, 1-ethene-1,1,2-triphosphonic acid, 1-propene-3,3,3-triphosphonic acid, 1-propene-1,1,2-triphosphonic acid, 1-propene-2,3,3-triphosphonic acid, 1-propene-1,1,3-triphosphonic acid, 1-propene-1,3,3-triphosphonic acid, 1-propene-1,2,3-triphosphonic acid, 1-butene-4,4,4-triphosphonic acid, 2-butene-4,4,4-triphosphonic acid, 1-butene-1,1,2-triphosphonic acid, 2-butene-3,4,4-triphosphonic acid, 1-butene-3,4,4-triphosphonic acid, 1-butene-1,3,3-triphosphonic acid, 2-butene-1,1,3-triphosphonic acid, 1-butene-2,4,4-triphosphonic acid, 1-butene-1,1,4-triphosphonic acid, 2-butene-1,1,4-triphosphonic acid, 1-butene-1,4,4-triphosphonic acid, 1-butene-3,3,4-triphosphonic acid, 1-butene-2,3,3-triphosphonic acid, 1-butene-1,3,3-triphosphonic acid, 1-butene-1,2,3-triphosphonic acid, 2-butene-2,3,4-triphosphonic acid, 1-butene-2,3,4-triphosphonic acid, 1-butene-1,2,4-triphosphonic acid, 2-butene-1,2,4-triphosphonic acid, 1-butene-1,3,4-triphosphonic acid, 2-pentene-1,1,5-triphosphonic acid, 2-pentene-1,5,5-triphosphonic acid, 1-pentene-1,5,5-triphosphonic acid, 2-pentene-1,4,4-triphosphonic acid, 1-pentene-1,4,4-triphosphonic acid, 1-hexene-1,1,6-triphosphonic acid, 2-hexene-1,1,6-triphosphonic acid, 3-hexene-1,1,6-triphosphonic acid, 2-hexene-1,6,6-triphosphonic acid, 1-hexene-1,6,6-triphosphonic acid, 1-hexene-1,5,5-triphosphonic acid, 2-hexene-1,5,5-triphosphonic acid, 3-hexene-2,2,6-triphosphonic acid, 1-propene-2,3,3,3-tetraphosphonic acid, 1-propene-1,3,3,3-tetraphosphonic acid, 1-propene-1,2,3,3-tetraphosphonic acid, 1-propene-1,1,3,3-tetraphosphonic acid, 1-butene-1,1,4,4-tetraphosphonic acid, 2-butene- 1,1,4,4-tetraphosphonic acid, 1-pentene-1,1,5,5-tetraphosphonic acid, 2-pentene-1,1,5,5-tetraphosphonic acid, 1-hexene-1,1,6,6-tetraphosphonic acid, 2-hexene-1,1,6,6-tetraphosphonic acid, 3-hexene-1,1,6,6-tetraphosphonic acid, 1-heptene-1,4,4,7-tetraphosphonic acid, 2-heptene-1,4,4,7-tetraphosphonic acid, 1-octene-1,4,4,8-tetraphosphonic acid, 2-octene-1,4,4,8-tetraphosphonic acid, 3-octene-1,5,5,8-tetraphosphonic acid, 1-nonene-1,5,5,9-tetraphosphonic acid, 2-nonene-1,5,5,9-tetraphosphonic acid, or 3-nonene-1,5,5,9-tetraphosphonic acid.

14. The process of any one of items 1 to 6, wherein the phosphonic acid compound is 1-cyclopentyl-phosphonic acid, 1,1-cyclopentyl-diphosphonic acid, 1,2-cyclopentyl-diphosphonic acid, 1,3-cyclopentyl-diphosphonic acid, 1-cyclohexyl-phosphonic acid, 1,1-cyclohexyl-diphosphonic acid, 1,2-cyclohexyl-diphosphonic acid, 1,3-cyclohexyl-diphosphonic acid, 1,4-cyclohexyl-diphosphonic acid, or phenyl-1-phosphonic acid.

15. The process of any one of items 1 to 6, wherein the phosphonic acid compound is a bisphosphonic acid.

16. The process of any one of items 1 to 6 and 15, wherein the phosphonic acid compound is etidronic acid, clodronic acid, alendronic acid, tiludronic acid, neridronic acid, olpadronic acid, risedronic acid, pamidronic acid, ibandronic acid, zoledronic acid, incadronic acid, minodronic acid, or EB-1053.

17. The process of any one of items 1 to 5, wherein the phosphonic acid compound is an amino acid which is substituted with 1 to 6 phosphonic acid groups.

18. The process of any one of items 1 to 5, wherein the phosphonic acid compound is a peptide of 2 to 15 amino acid residues, which is substituted with 1 to 6 phosphonic acid groups.

19. The process of any one of items 1 to 5 and 18, wherein the phosphonic acid compound is a peptide of 3 to 15 amino acid residues, which contains the amino acid sequence RGD, and wherein the peptide is substituted with 1 to 6 phosphonic acid groups.

20. The process of item 19, wherein said peptide is selected from RGD, GRGD, RGDE, RGDT, RGDS, GRGDS, GRGDSP, GRGDSPC, GRGDSPK, GRGDSC, RGDS-PASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), and c(GRGDSP).

21. The process of any one of items 1 to 5, wherein the phosphonic acid compound is a statin substituted with 1 to 6 phosphonic acid groups, an analgesic substituted with 1 to 6 phosphonic acid groups, an antiinflammatory agent substituted with 1 to 6 phosphonic acid groups, or vitamin D substituted with 1 to 6 phosphonic acid groups.

22. The process of any one of items 1 to 5, wherein the phosphonic acid compound is aspirin substituted with 1 to 6 phosphonic acid groups, or ibuprofen substituted with 1 to 6 phosphonic acid groups.

23. The process of any one of items 1 to 22, wherein the surface of the implant is treated with said phosphonic acid compound or a pharmaceutically acceptable salt thereof.

24. The process of any one of items 1 to 23, wherein the pharmaceutically acceptable salt of the phosphonic acid compound is an alkali metal salt or an alkaline earth metal salt.

25. The process of any one of items 1 to 23, wherein the pharmaceutically acceptable salt of the phosphonic acid compound is a sodium salt, a potassium salt, a calcium salt, a magnesium salt, a strontium salt, or a technetium salt.

26. The process of any one of items 1 to 22, wherein the pharmaceutically acceptable ester of the phosphonic acid compound is a $C_{1-6}$ alkyl phosphonate.

27. The process of any one of items 1 to 22 and 26, wherein the pharmaceutically acceptable ester of the phosphonic acid compound is a methyl ester, an ethyl ester, an n-propyl ester, an isopropyl ester, an n-butyl ester, a tert-butyl ester, an n-pentyl ester, or an n-hexyl ester.

28. The process of any one of items 1 to 22, wherein the pharmaceutically acceptable amide of the phosphonic acid compound is an N,N-di($C_{1-6}$ alkyl) phosphonamidate.

29. The process of item 28, wherein the $C_{1-6}$ alkyl groups comprised in said N,N-di($C_{1-6}$ alkyl) phosphonamidate are selected from methyl, ethyl, n-propyl, isopropyl, n-butyl, tert-butyl, n-pentyl, and n-hexyl.

30. The process of any one of items 1 to 16, wherein the surface of the implant is treated with a pharmaceutically acceptable amide of the phosphonic acid compound, and wherein said amide is formed from the phosphonic acid compound and an amino acid.

31. The process of any one of items 1 to 16, wherein the surface of the implant is treated with a pharmaceutically acceptable amide of the phosphonic acid compound, and wherein said amide is formed from the phosphonic acid compound and a peptide of 2 to 15 amino acid residues.

32. The process of item 31, wherein the pharmaceutically acceptable amide is formed from the phosphonic acid compound and a peptide of 3 to 15 amino acid residues, wherein said peptide contains the amino acid sequence RGD.

33. The process of item 32, wherein said peptide is selected from RGD, GRGD, RGDE, RGDT, RGDS, GRGDS, GRGDSP, GRGDSPC, GRGDSPK, GRGDSC, RGDS-PASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), and c(GRGDSP).

34. The process of any one of items 1 to 33, wherein the phosphonic acid compound or the pharmaceutically acceptable salt, ester or amide thereof is employed at a concentration of about 0.5 mM to about 10 mM.

35. The process of any one of items 1 to 34, wherein the surface of the implant is treated with two or more different phosphonic acid compounds or pharmaceutically acceptable salts, esters or amides thereof.

36. The process of any one of items 1 to 35, wherein the process further comprises, before the step of treatment with the phosphonic acid compound, a step of pre-treating the surface of the implant with a cleaning agent.

37. The process of item 36, wherein the step of pre-treatment with the cleaning agent is conducted at a temperature of about 50° C. to about 90° C.

38. The process of item 36 or 37, wherein the step of pre-treatment with the cleaning agent is conducted at a temperature of about 55° C. to about 75° C.

39. The process of any one of items 36 to 38, wherein the step of pre-treatment with the cleaning agent is conducted at a temperature of about 60° C. to about 70° C.

40. The process of any one of items 36 to 39, wherein the step of pre-treatment with the cleaning agent is conducted at a temperature of about 65° C.

41, The process of any one of items 36 to 40, wherein the step of pre-treatment with the cleaning agent is conducted under sonication.

42. The process of any one of items 36 to 41, wherein the cleaning agent is a phosphate-free alkaline cleaning agent.

43. The process of any one of items 36 to 42, wherein the cleaning agent comprises a chelating agent and an inorganic base.
44. The process of any one of items 36 to 43, wherein the cleaning agent comprises methylglycinediacetic acid or a salt thereof.
45. The process of any one of items 36 to 44, wherein the cleaning agent is a 0.5% (v/v) to 5% (v/v) aqueous solution of an alkaline phosphate-free liquid concentrate, wherein the liquid concentrate has a pH greater than 12 and comprises about 5% (w/w) to about 15% (w/w) of methylglycinediacetate and about 1% (w/w) to about 5% (w/w) of an inorganic base, and wherein said 0.5% (v/v) to 5% (v/v) aqueous solution has a pH equal to or greater than 11.
46. The process of any one of items 36 to 45, wherein the cleaning agent is a 2% (v/v) aqueous solution of an alkaline phosphate-free liquid concentrate, wherein the liquid concentrate has a pH greater than 12 and comprises about 5% (w/w) to about 15% (w/w) of methylglycinediacetate and about 1% (w/w) to about 5% (w/w) of an inorganic base, and wherein said 2% (v/v) aqueous solution has a pH greater than 12.
47. The process of any one of items 43 to 46, wherein the inorganic base is potassium hydroxide and/or sodium hydroxide.
48. The process of any one of items 36 to 47, wherein the process further comprises, after the step of pre-treatment with the cleaning agent and before the step of treatment with the phosphonic acid compound, a first step of rinsing the surface of the implant with water.
49. The process of item 48, wherein the first step of rinsing with water is conducted at a temperature of about 50° C. to about 90° C.
50. The process of item 48 or 49, wherein the first step of rinsing with water is conducted at a temperature of about 55° C. to about 75° C.
51. The process of any one of items 48 to 50, wherein the first step of rinsing with water is conducted at a temperature of about 60° C. to about 70° C.
52. The process of any one of items 48 to 51, wherein the first step of rinsing with water is conducted at a temperature of about 65° C.
53. The process of any one of items 48 to 52, wherein the first step of rinsing with water is conducted under sonication.
54. The process of any one of items 48 to 53, wherein the first step of rinsing with water is repeated until the used water after rinsing has a pH of 6.2±0.5.
55. The process of any one of items 1 to 54, wherein the process further comprises, after the step of treatment with the phosphonic acid compound, a second step of rinsing the surface of the implant with water.
56. The process of item 55, wherein the second step of rinsing with water is conducted at a temperature of about 50° C. to about 90° C.
57. The process of item 55 or 56, wherein the second step of rinsing with water is conducted at a temperature of about 55° C. to about 75° C.
58. The process of any one of items 55 to 57, wherein the second step of rinsing with water is conducted at a temperature of about 60° C. to about 70° C.
59. The process of any one of items 55 to 58, wherein the second step of rinsing with water is conducted at a temperature of about 65° C.
60. The process of any one of items 55 to 59, wherein the second step of rinsing with water is conducted under sonication.
61. The process of any one of items 55 to 60, wherein the second step of rinsing with water is repeated until the used water after rinsing has a pH of 6.2±0.5.
62. The process of any one of items 1 to 61, wherein all steps of the process are conducted at a temperature of about 50° C. to about 90° C.
63. The process of any one of items 1 to 62, wherein all steps of the process are conducted at a temperature of about 55° C. to about 75° C.
64. The process of any one of items 1 to 63, wherein all steps of the process are conducted at a temperature of about 60° C. to about 70° C.
65. The process of any one of items 1 to 64, wherein all steps of the process are conducted at a temperature of about 65° C.
66. The process of any one of items 1 to 65, wherein all steps of the process are conducted under sonication.
67. The process of any one of items 1 to 66, wherein the process comprises the following steps:
pre-treating the surface of the implant with the cleaning agent;
rinsing the surface of the implant with water;
treating the surface of the implant with the phosphonic acid compound or the pharmaceutically acceptable salt, ester or amide thereof; and
rinsing the surface of the implant with water;
wherein all of the above-mentioned steps are conducted under sonication at a temperature of about 55° C. to about 75° C.
68. The process of any one of items 1 to 67, wherein the implant is a bone-anchored implant or a soft tissue-interfacing implant.
69. The process of any one of items 1 to 68, wherein the implant is a dental abutment, a coronary stent, a dental implant, a hip implant, a spinal implant, a small joints implant, a shoulder implant, or a knee implant.
70. The process of any one of items 1 to 69, wherein the implant is an endosseous implant.
71. The process of any one of items 1 to 70, wherein the implant is a dental endosseous implant.
72. The process of any one of items 1 to 71, wherein the implant has the form of a screw, a plate, a nail, or a pin.
73. The process of any one of items 1 to 72, wherein the surface of the implant is made of a metal, a metal alloy, or a ceramic.
74. The process of any one of items 1 to 73, wherein the surface of the implant is made of a metal or a metal alloy.
75. The process of any one of items 1 to 74, wherein the surface of the implant is made of titanium, chromium, niobium, tantalum, vanadium, zirconium, aluminum, cobalt, nickel, stainless steel, or an alloy of any of the aforementioned metals.
76. The process of any one of items 1 to 75, wherein the surface of the implant is made of titanium or a titanium alloy.
77. The process of any one of items 1 to 76, wherein the surface of the implant is made of grade 4 titanium, Ti-6Al-4V alloy (grade 5 titanium), Ti-6Al-4V ELI alloy (grade 23 titanium), a titanium-niobium alloy, or a titanium-zirconium alloy.
78. The process of any one of items 1 to 75, wherein the surface of the implant is made of a cobalt-chromium alloy.
79. The process of any one of items 1 to 73, wherein the surface of the implant is made of a ceramic.

80. The process of any one of items 1 to 73 and 79, wherein the surface of the implant is made of a ceramic which is an oxide, a carbide, a nitride, an oxynitride, a carbonitride, or an oxycarbide of a metal or of a metal alloy.

81. The process of item 80, wherein said metal or metal alloy is selected from titanium, chromium, niobium, tantalum, vanadium, zirconium, aluminum, cobalt, nickel, stainless steel, and alloys thereof.

82. The process of any one of items 1 to 73 and 79 to 81, wherein the surface of the implant is made of a ceramic selected from titanium oxide, titanium carbide, titanium nitride, titanium oxynitride, titanium carbonitride, and titanium oxycarbide.

83. The process of any one of items 1 to 73 and 79, wherein the surface of the implant is made of a ceramic selected from aluminum oxide, zirconium oxide, silicon oxide, aluminum oxide/zirconium oxide, and aluminum oxide/zirconium oxide/yttrium oxide.

84. A process of producing a surface-treated implant, comprising conducting the process of any one of items 1 to 83 to obtain the surface-treated implant.

85. The process of item 84, further comprising a step of placing the surface-treated implant in a packaging.

86. An implant obtainable by the process of any one of items 1 to 85.

87. An implant having a surface made of a metal, a metal alloy or a ceramic, wherein a phosphonic acid compound or a pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy, of at least 70% of a reference maximum surface coverage,
wherein the reference maximum surface coverage refers to the surface coverage, in terms of the ratio of the phosphorus content to the metal content as determined by X-ray photoelectron spectroscopy, that is obtained if the implant is first pre-treated with a 2% (v/v) aqueous solution, having a pH greater than 12, of an alkaline phosphate-free liquid cleaning concentrate under sonication at a temperature of 65° C. for a period of 30 min, is then rinsed with water under sonication at a temperature of 65° C. until the used water after rinsing has a pH of 6.2±0.5, and is then treated with a 5 mM aqueous solution of the phosphonic acid compound or the pharmaceutically acceptable salt, ester or amide thereof under sonication at a temperature of 65° C. for a period of 60 min, wherein said liquid cleaning concentrate comprises 5% (w/w) to 15% (w/w) of methylglycinediacetate and 1% (w/w) to 5% (w/w) of potassium hydroxide and has a pH greater than 12.

88. The implant of item 87, wherein the phosphonic acid compound or the pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy, of at least about 80% of said reference maximum surface coverage.

89. The implant of item 87 or 88, wherein the phosphonic acid compound or the pharmaceutically acceptable salt, ester or amide thereof is bound to the surface of the implant and forms a monolayer having an implant surface coverage, in terms of the ratio of the phosphorus content to the metal content as determined by X-ray photoelectron spectroscopy, of at least about 90% of said reference maximum surface coverage.

90. The implant of any one of items 87 to 89, wherein the phosphonic acid compound is a $C_{1-30}$ hydrocarbon which is substituted with 1 to 6 phosphonic acid groups, wherein said hydrocarbon is optionally substituted with one or more groups independently selected from hydroxy and halogen, and further wherein one or more carbon atoms comprised in said hydrocarbon are optionally each replaced by a heteroatom independently selected from nitrogen, oxygen and sulfur.

91. The implant of any one of items 87 to 90, wherein the phosphonic acid compound is a $C_{1-15}$ hydrocarbon which is substituted with 1 to 6 phosphonic acid groups.

92. The implant of any one of items 87 to 91, wherein the phosphonic acid compound is a $C_{1-10}$ alkane which is substituted with 3 to 6 phosphonic acid groups.

93. The implant of any one of items 87 to 92, wherein the phosphonic acid compound is a linear $C_{2-6}$ alkane which is substituted with 3 or 4 phosphonic acid groups.

94. The implant of any one of items 87 to 90, wherein the phosphonic acid compound is methanephosphonic acid, ethanephosphonic acid, propane-1-phosphonic acid, propane-2-phosphonic acid, methane-1,1-diphosphonic acid, ethane-1,1-diphosphonic acid, ethane-1,2-diphosphonic acid, propane-1,1-diphosphonic acid, propane-2,2-diphosphonic acid, propane-1,2-diphosphonic acid, propane-1,3-diphosphonic acid, ethane-1,1,1-triphosphonic acid, ethane-1,1,2-triphosphonic acid, propane-1,1,1-triphosphonic acid, propane-1,1,2-triphosphonic acid, propane-1,1,3-triphosphonic acid, propane-1,2,2-triphosphonic acid, propane-1,2,3-triphosphonic acid, butane-1,1,1-triphosphonic acid, butane-1,1,2-triphosphonic acid, butane-1,1,3-triphosphonic acid, butane-1,1,4-triphosphonic acid, butane-1,2,2-triphosphonic acid, butane-2,2,3-triphosphonic acid, butane-1,3,3-triphosphonic acid, butane-1,2,3-triphosphonic acid, butane-1,2,4-triphosphonic acid, pentane-1,1,5-triphosphonic acid, pentane-2,2,5-triphosphonic acid, hexane-1,1,6-triphosphonic acid, hexane-2,2,6-triphosphonic acid, propane-1,1,1,2-tetraphosphonic acid, propane-1,1,1,3-tetraphosphonic acid, propane-1,1,2,2-tetraphosphonic acid, propane-1,1,2,3-tetraphosphonic acid, propane-1,1,3,3-tetraphosphonic acid, propane-1,2,2,3-tetraphosphonic acid, butane-1,1,4,4-tetraphosphonic acid, pentane-1,1,5,5-tetraphosphonic acid, hexane-1,1,6,6-tetraphosphonic acid, heptane-1,4,4,7-tetraphosphonic acid, octane-1,4,4,8-tetraphosphonic acid, nonane-1,5,5,9-tetraphosphonic acid, pentane-1,1,3,5,5-pentaphosphonic acid, or pentane-1,1,2,4,5,5-hexaphosphonic acid.

95. The implant of any one of items 87 to 94, wherein the phosphonic acid compound is propane-1,1,3,3-tetraphosphonic acid.

96. The implant of any one of items 87 to 90, wherein the phosphonic acid compound is tert-butyl phosphonic acid, 2-methyl-propane-1,1,1-triphosphonic acid, 2-methyl-propane-1,1,3-triphosphonic acid, 2-(phosphono-methyl)-propane-1,3-diphosphonic acid, 2-methyl-propane-1,1,3,3-tetraphosphonic acid, 2-methyl-butane-1,1,1-triphosphonic acid, 3-methyl-butane-1,1,1-triphosphonic acid, 2-(phosphono-methyl)-propane-1,1-diphosphonic acid, 2-methyl-butane-1,1,3-triphosphonic acid, 2-methyl-butane-1,1,4-triphosphonic acid, 3-methyl-butane-2,2,4-triphosphonic acid, 3-methyl-butane-1,1,4-triphosphonic acid, 2-(phosphono-methyl)-butane-1,3-diphosphonic acid, 2-(phosphono-methyl)-butane-1,4-diphosphonic acid, 3-methyl-butane-1,1,2-triphosphonic acid, 2-methyl-butane-1,1,4,4-tetraphosphonic acid, 2-methyl-pentane-1,1,1- triphosphonic acid, 2-(phosphono-methyl)-pentane-1,1-diphosphonic acid, 2-methyl-pentane-1,1,3-triphosphonic acid, 2-methyl-pentane-1,1,4-triphosphonic acid, 2-methyl-pentane-1,1,5-triphosphonic acid, 2-methyl-pentane-1,3,3-triphosphonic acid, 4-methyl-pentane-2,2,5-triphosphonic acid, 4-methyl-pentane-1,1,5-triphosphonic acid, 2-(phosphono-methyl)-pentane-1,3-diphosphonic acid, 2-methyl-pentane-1,3,4-triphosphonic acid, 2-(phosphono-methyl)-pentane-1,4-diphosphonic acid, 2-(phosphono-methyl)-pentane-1,5-diphosphonic acid, 2-methyl-pentane-1,3,5-triphosphonic acid, 4-methyl-pentane-1,2,5-triphosphonic acid, 2-methyl-pentane-1,1,5,5-tetraphosphonic acid, 3-methyl-pentane-1,1,1-triphosphonic acid, 3-methyl-pentane-1,1,2-triphosphonic acid, 3-(phosphono-methyl)-pentane-1,1-diphosphonic acid, 3-methyl-pentane-1,1,5-triphosphonic acid, 3-(triphosphono-methyl)-pentane, 3-(phosphono-methyl)-pentane-1,5-diphosphonic acid, 3-methyl-pentane-2,2,5-triphosphonic acid, 2-methyl-hexane-1,1,1-triphosphonic acid, 2-(phosphono-methyl)-hexane-1,6-diphosphonic acid, 2-methyl-hexane-1,1,6,6-tetraphosphonic acid, 4-methyl-heptane-1,1,1-triphosphonic acid, 4-methyl-heptane-1,1,6,6-tetraphosphonic acid, 2-methyl-octane-1,1,1-triphosphonic acid, 2-methyl-octane-1,1,8,8-tetraphosphonic acid, 3-(bisphosphono-methyl)-butane-1,1,4,4-tetraphosphonic acid, 3-(bisphosphono-methyl)-pentane-1,1,5,5-tetraphosphonic acid, or diethylenetriamine penta(methylene phosphonic acid).

97. The implant of any one of items 87 to 90, wherein the phosphonic acid compound is vinyl phosphonic acid, 1-propene-3-phosphonic acid, 2-propene-3-phosphonic acid, 1-propene-2-phosphonic acid, ethene-1,1-diphosphonic acid, ethene-1,2-diphosphonic acid, 1-propene-1,1-diphosphonic acid, 1-propene-3,3-diphosphonic acid, 1-propene-1,2-diphosphonic acid, 1-propene-2,3-diphosphonic acid, 1-propene-1,3-diphosphonic acid, 1-ethene-1,1,2-triphosphonic acid, 1-propene-3,3,3-triphosphonic acid, 1-propene-1,1,2-triphosphonic acid, 1-propene-2,3,3-triphosphonic acid, 1-propene-1,1,3-triphosphonic acid, 1-propene-1,3,3-triphosphonic acid, 1-propene-1,2,3-triphosphonic acid, 1-butene-4,4,4-triphosphonic acid, 2-butene-4,4,4-triphosphonic acid, 1-butene-1,1,2-triphosphonic acid, 2-butene-3,4,4-triphosphonic acid, 1-butene-3,4,4-triphosphonic acid, 1-butene-1,1,3-triphosphonic acid, 2-butene-1,1,3-triphosphonic acid, 1-butene-2,4,4-triphosphonic acid, 1-butene-1,1,4-triphosphonic acid, 2-butene-1,1,4-triphosphonic acid, 1-butene-1,4,4-triphosphonic acid, 1-butene-3,3,4-triphosphonic acid, 1-butene-2,3,3-triphosphonic acid, 1-butene-1,3,3-triphosphonic acid, 1-butene-1,2,3-triphosphonic acid, 2-butene-2,3,4-triphosphonic acid, 1-butene-2,3,4-triphosphonic acid, 1-butene-1,2,4-triphosphonic acid, 2-butene-1,2,4-triphosphonic acid, 1-butene-1,3,4-triphosphonic acid, 2-pentene-1,1,5-triphosphonic acid, 2-pentene-1,5,5-triphosphonic acid, 1-pentene-1,5,5-triphosphonic acid, 2-pentene-1,4,4-triphosphonic acid, 1-pentene-1,4,4-triphosphonic acid, 1-hexene-1,1,6-triphosphonic acid, 2-hexene-1,1,6-triphosphonic acid, 3-hexene-1,1,6-triphosphonic acid, 2-hexene-1,6,6-triphosphonic acid, 1-hexene-1,6,6-triphosphonic acid, 1-hexene-1,5,5-triphosphonic acid, 2-hexene-1,5,5-triphosphonic acid, 3-hexene-2,2,6-triphosphonic acid, 1-propene-2,3,3,3-tetraphosphonic acid, 1-propene-1,3,3,3-tetraphosphonic acid, 1-propene-1,2,3,3-tetraphosphonic acid, 1-propene-1,1,3,3-tetraphosphonic acid, 1-butene-1,1,4,4-tetraphosphonic acid, 2-butene-1,1,4,4-tetraphosphonic acid, 1-pentene-1,1,5,5-tetraphosphonic acid, 2-pentene-1,1,5,5-tetraphosphonic acid, 1-hexene-1,1,6,6-tetraphosphonic acid, 2-hexene-1,1,6,6-tetraphosphonic acid, 3-hexene-1,1,6,6-tetraphosphonic acid, 1-heptene-1,4,4,7-tetraphosphonic acid, 2-heptene-1,4,4,7-tetraphosphonic acid, 1-octene-1,4,4,8-tetraphosphonic acid, 2-octene-1,4,4,8-tetraphosphonic acid, 3-octene-1,5,5,8-tetraphosphonic acid, 1-nonene-1,5,5,9-tetraphosphonic acid, 2-nonene-1,5,5,9-tetraphosphonic acid, or 3-nonene-1,5,5,9-tetraphosphonic acid.

98. The implant of any one of items 87 to 90, wherein the phosphonic acid compound is 1-cyclopentyl-phosphonic acid, 1,1-cyclopentyl-diphosphonic acid, 1,2-cyclopentyl-diphosphonic acid, 1,3-cyclopentyl-diphosphonic acid, 1-cyclohexyl-phosphonic acid, 1,1-cyclohexyl-diphosphonic acid, 1,2-cyclohexyl-diphosphonic acid, 1,3-cyclohexyl-diphosphonic acid, 1,4-cyclohexyl-diphosphonic acid, or phenyl-1-phosphonic acid.

99. The implant of any one of items 87 to 90, wherein the phosphonic acid compound is a bisphosphonic acid.

100. The implant of any one of items 87 to 90 and 99, wherein the phosphonic acid compound is etidronic acid, clodronic acid, alendronic acid, tiludronic acid, neridronic acid, olpadronic acid, risedronic acid, pamidronic acid, ibandronic acid, zoledronic acid, incadronic acid, minodronic acid, or EB-1053.

101. The implant of any one of items 87 to 89, wherein the phosphonic acid compound is an amino acid which is substituted with 1 to 6 phosphonic acid groups.

102. The implant of any one of items 87 to 89, wherein the phosphonic acid compound is a peptide of 2 to 15 amino acid residues, which is substituted with 1 to 6 phosphonic acid groups.

103. The implant of any one of items 87 to 89 and 102, wherein the phosphonic acid compound is a peptide of 3 to 15 amino acid residues, which contains the amino acid sequence RGD, and wherein the peptide is substituted with 1 to 6 phosphonic acid groups.

104. The implant of item 103, wherein said peptide is selected from RGD, GRGD, RGDE, RGDT, RGDS, GRGDS, GRGDSP, GRGDSPC, GRGDSPK, GRGDSC, RGDSPASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), and c(GRGDSP).

105. The implant of any one of items 87 to 89, wherein the phosphonic acid compound is a statin substituted with 1 to 6 phosphonic acid groups, an analgesic substituted with 1 to 6 phosphonic acid groups, an antiinflammatory agent substituted with 1 to 6 phosphonic acid groups, or vitamin D substituted with 1 to 6 phosphonic acid groups.

106. The implant of any one of items 87 to 89, wherein the phosphonic acid compound is aspirin substituted with 1 to 6 phosphonic acid groups, or ibuprofen substituted with 1 to 6 phosphonic acid groups.

107. The implant of any one of items 87 to 106, wherein said phosphonic acid compound or a pharmaceutically acceptable salt thereof is bound to the surface of the implant.

108. The implant of any one of items 87 to 107, wherein the pharmaceutically acceptable salt of the phosphonic acid compound is an alkali metal salt or an alkaline earth metal salt.

109. The implant of any one of items 87 to 107, wherein the pharmaceutically acceptable salt of the phosphonic acid compound is a sodium salt, a potassium salt, a calcium salt, a magnesium salt, a strontium salt, or a technetium salt.

110. The implant of any one of items 87 to 106, wherein the pharmaceutically acceptable ester of the phosphonic acid compound is a $C_{1-6}$ alkyl phosphonate.

111. The implant of any one of items 87 to 106 and 110, wherein the pharmaceutically acceptable ester of the phosphonic acid compound is a methyl ester, an ethyl ester, an n-propyl ester, an isopropyl ester, an n-butyl ester, a tert-butyl ester, an n-pentyl ester, or an n-hexyl ester.

112. The implant of any one of items 87 to 106, wherein the pharmaceutically acceptable amide of the phosphonic acid compound is an N,N-di($C_{1-6}$ alkyl) phosphonamidate.

113. The implant of item 112, wherein the $C_{1-6}$ alkyl groups comprised in said N,N-di($C_{1-6}$ alkyl) phosphonamidate are selected from methyl, ethyl, n-propyl, isopropyl, n-butyl, tert-butyl, n-pentyl, and n-hexyl.

114. The implant of any one of items 87 to 100, wherein a pharmaceutically acceptable amide of the phosphonic acid compound is bound to the surface of the implant, and wherein said amide is formed from the phosphonic acid compound and an amino acid.

115. The implant of any one of items 87 to 100, wherein a pharmaceutically acceptable amide of the phosphonic acid compound is bound to the surface of the implant, and wherein said amide is formed from the phosphonic acid compound and a peptide of 2 to 15 amino acid residues.

116. The implant of item 115, wherein the pharmaceutically acceptable amide is formed from the phosphonic acid compound and a peptide of 3 to 15 amino acid residues, wherein said peptide contains the amino acid sequence RGD.

117. The implant of item 116, wherein said peptide is selected from RGD, GRGD, RGDE, RGDT, RGDS, GRGDS, GRGDSP, GRGDSPC, GRGDSPK, GRGDSC, RGDSPASSKP, GRGDNP, GRGDTP, RGDC, RGDV, DRGDS, YRGDS, rGDW, GFRGDGQ, CRGDFPASSC, c(RGDfK), c(RGDfV), cilengitide, c(RGDfC), c(RGDyK), c(GRGDSPA), and c(GRGDSP).

118. The implant of any one of items 87 to 117, wherein the implant is a bone-anchored implant or a soft tissue-anchored implant.

119. The implant of any one of items 87 to 118, wherein the implant is a dental abutment, a coronary stent, a dental implant, a hip implant, a spinal implant, a small joints implant, a shoulder implant, or a knee implant.

120. The implant of any one of items 87 to 119, wherein the implant is an endosseous implant.

121. The implant of any one of items 87 to 120, wherein the implant is a dental endosseous implant.

122. The implant of any one of items 87 to 121, wherein the implant has the form of a screw, a plate, a nail, or a pin.

123. The implant of any one of items 87 to 122, wherein the surface of the implant is made of a metal or a metal alloy.

124. The implant of any one of items 87 to 123, wherein the surface of the implant is made of titanium, chromium, niobium, tantalum, vanadium, zirconium, aluminum, cobalt, nickel, stainless steel, or an alloy of any of the aforementioned metals.

125. The implant of any one of items 87 to 124, wherein the surface of the implant is made of titanium or a titanium alloy.

126. The implant of any one of items 87 to 125, wherein the surface of the implant is made of grade 4 titanium, Ti-6Al-4V alloy (grade 5 titanium), Ti-6Al-4V ELI alloy (grade 23 titanium), a titanium-niobium alloy, or a titanium-zirconium alloy.

127. The implant of any one of items 87 to 124, wherein the surface of the implant is made of a cobalt-chromium alloy.

128. The implant of any one of items 87 to 122, wherein the surface of the implant is made of a ceramic.

129. The implant of any one of items 87 to 122 and 128, wherein the surface of the implant is made of a ceramic which is an oxide, a carbide, a nitride, an oxynitride, a carbonitride, or an oxycarbide of a metal or of a metal alloy.

130. The implant of item 129, wherein said metal or metal alloy is selected from titanium, chromium, niobium, tantalum, vanadium, zirconium, aluminum, cobalt, nickel, stainless steel, and alloys thereof.

131. The implant of any one of items 87 to 122 and 128 to 130, wherein the surface of the implant is made of a ceramic selected from titanium oxide, titanium carbide, titanium nitride, titanium oxynitride, titanium carbonitride, and titanium oxycarbide.

132. The implant of any one of items 87 to 122 and 128, wherein the surface of the implant is made of a ceramic selected from aluminum oxide, zirconium oxide, silicon oxide, aluminum oxide/zirconium oxide, and aluminum oxide/zirconium oxide/yttrium oxide.

133. The implant of any one of items 87 to 89, wherein the implant is obtainable by the process of any one of items 1 to 85.

The invention is also described by the following illustrative figures. The appended figures show:

FIG. 1: Phosphorus over metal ratio ("Phosphorus/Metal") of titanium grade 4 cylinders, the surface of which was treated with a phosphonic acid compound using either the process according to the invention (Example 12) or a comparative process according to EP-A-1343545 (Example 13). See Example 14.

Figure 2:
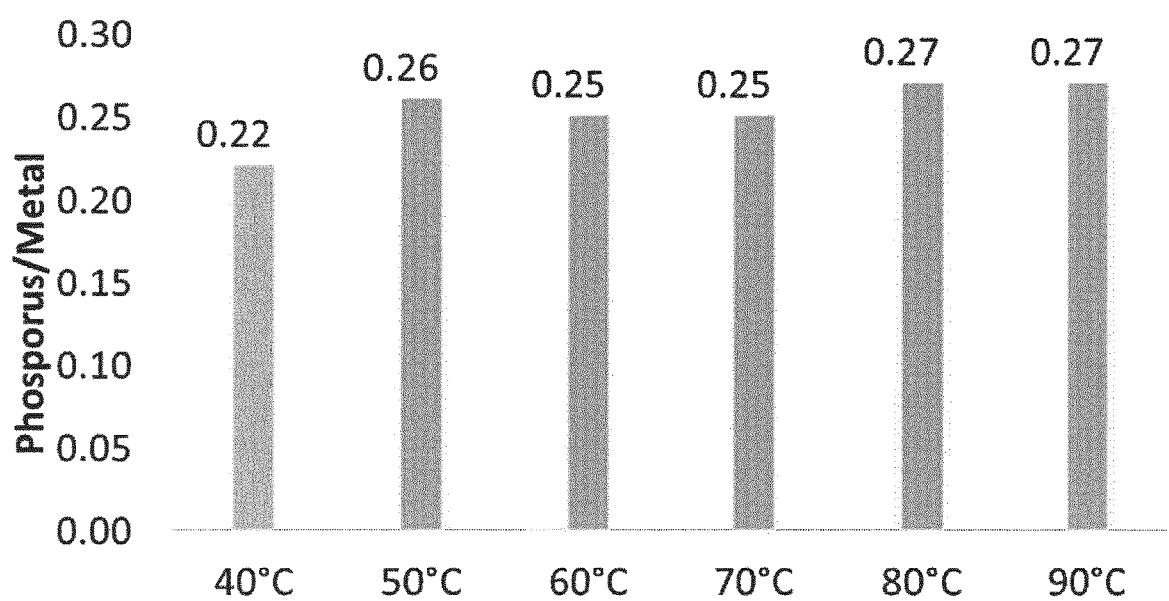

FIG. 2: Phosphorus over metal ratio ("Phosphorus/Metal") of titanium grade 4 cylinders, the surface of which was treated with a phosphonic acid compound at different temperatures in accordance with the present invention or at a lower temperature (reference). See Example 15.

Figure 3:
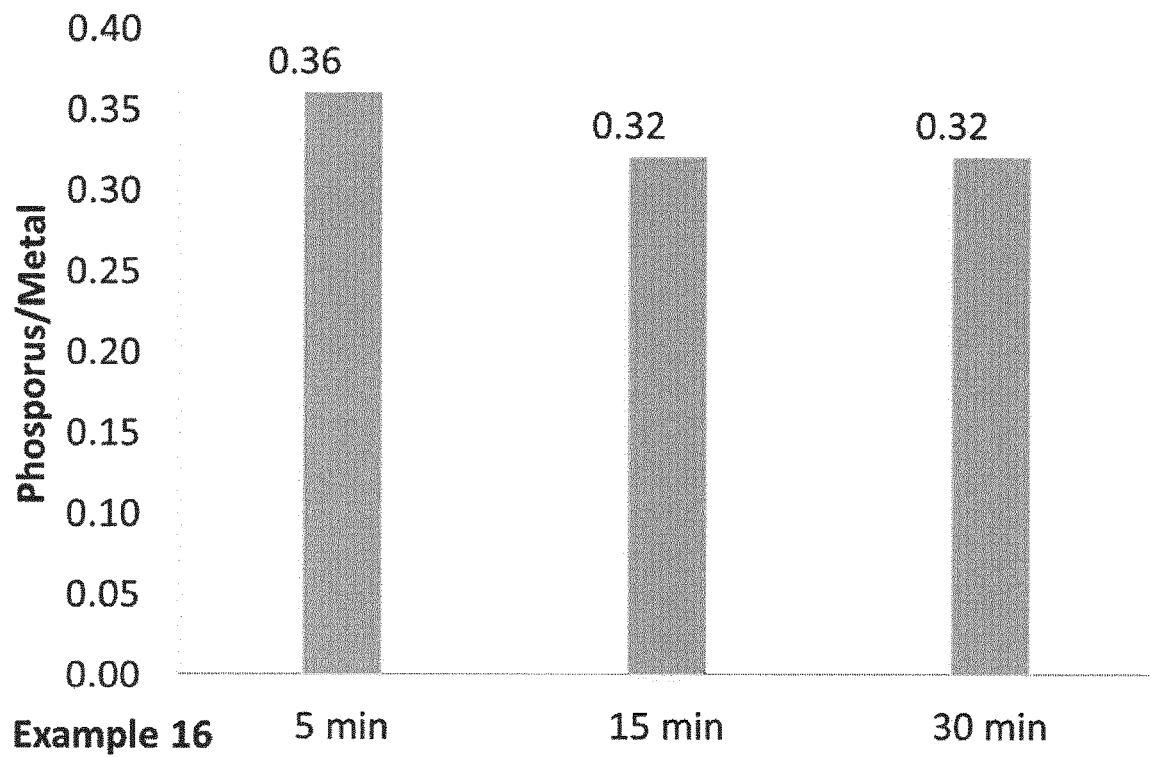

FIG. 3: Phosphorus over metal ratio ("Phosphorus/Metal") of titanium grade 4 cylinders, the surface of which was treated with a phosphonic acid compound in accordance with the invention, carrying out a pre-treatment cleaning step for different time periods. See Example 16.

Figure 4:
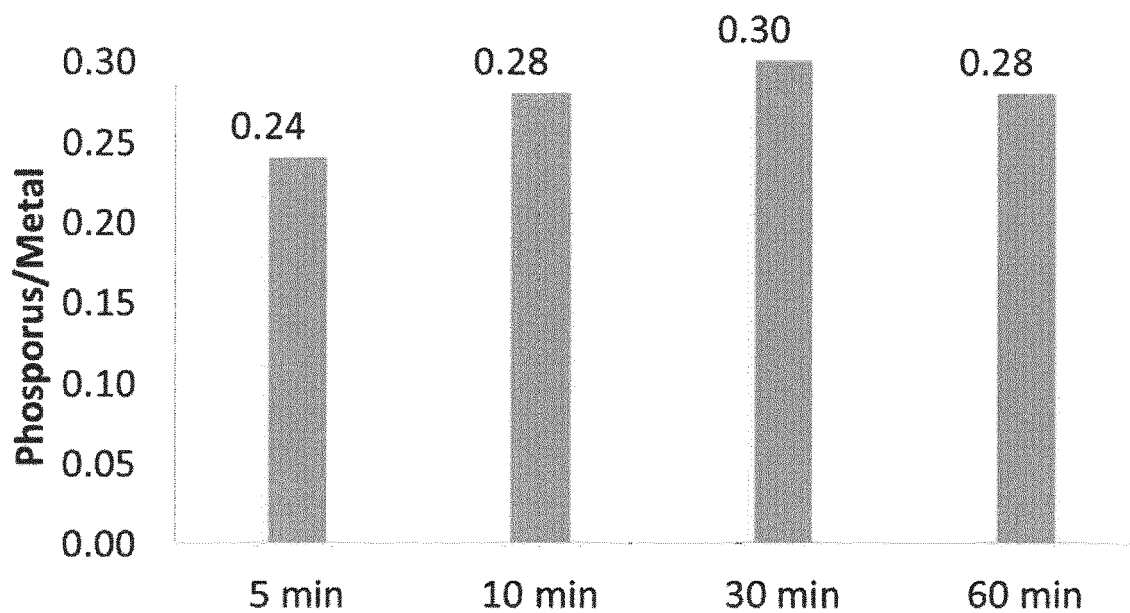

FIG. 4: Phosphorus over metal ratio ("Phosphorus/Metal") of titanium grade 4 cylinders, the surface of which was treated with a phosphonic acid compound for different time periods in accordance with the invention. See Example 17.

Figure 5:
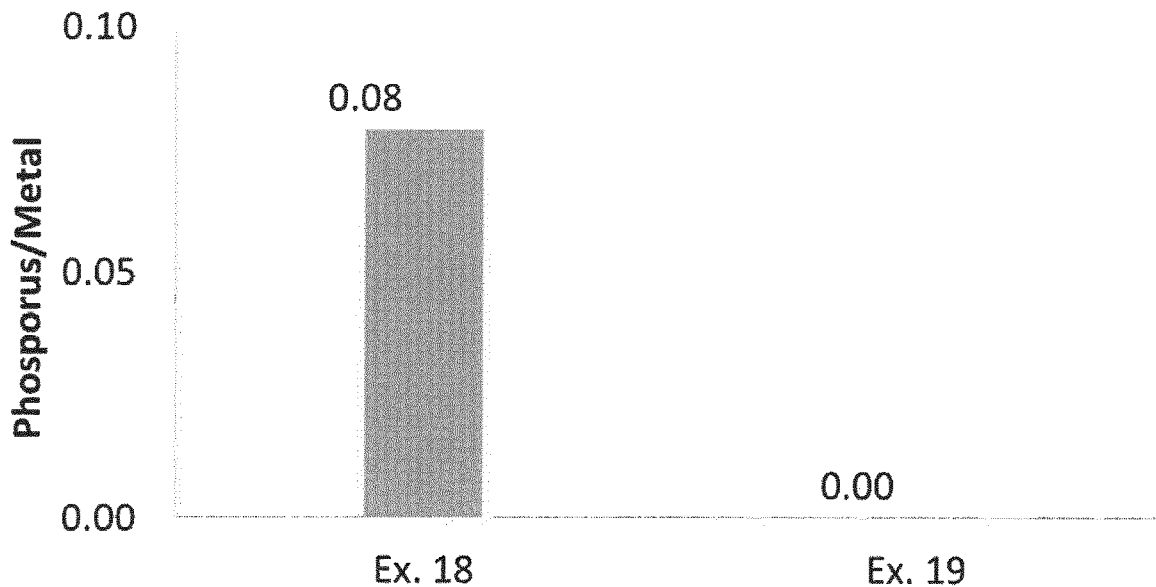

FIG. 5: Phosphorus over metal ratio ("Phosphorus/Metal") of cobalt chrome discs, the surface of which was treated with a phosphonic acid compound using either the process according to the invention (Example 18) or a comparative process according to EP-A-1343545 (Example 19). See Example 20.

Figure 6:
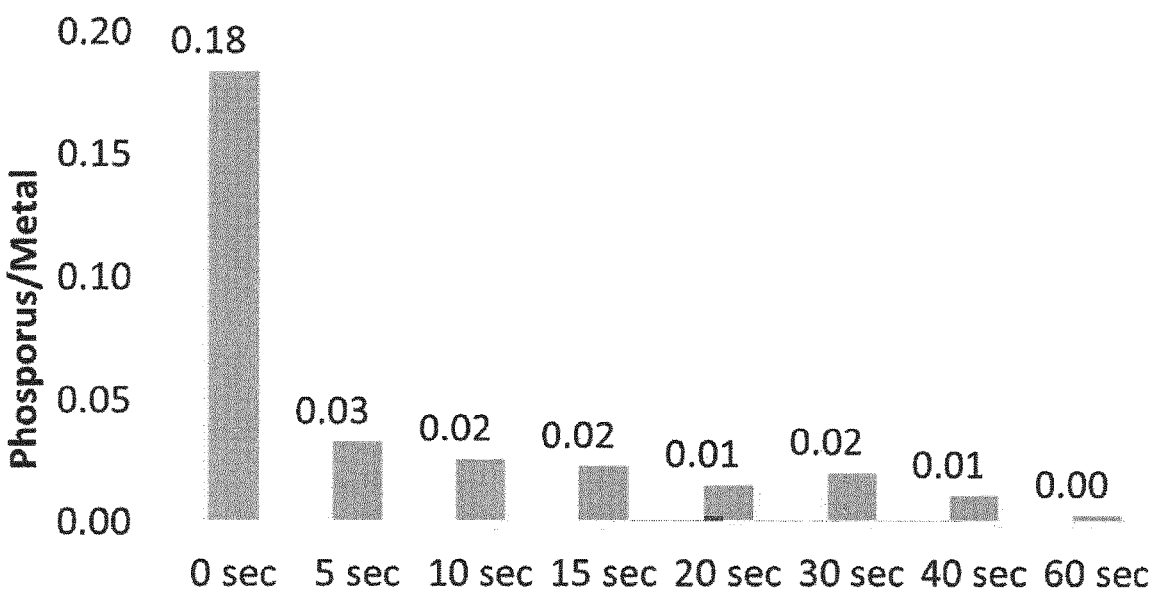

FIG. 6: Determination of the thickness of a layer of phosphonic acid compound on the surface of ceramic discs by depth profiling using XPS (see Example 27).

The invention will now be described by reference to the following examples which are merely illustrative and are not to be construed as a limitation of the scope of the present invention.

EXAMPLES

Example 1

A Titanium grade 23 dental implant (bulk composition atomic concentration Titanium 90%, Aluminum 6%, Vanadium 4%; length 11.0 mm, diameter 3.75 mm) was provided with a roughened surface, produced by sand blasting and acid etching according to industry standards. The dental implant was immersed in 40 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 30 min. The implant was removed from the cleaning agent solution and rinsed with water as follows: 2 times with 40 ml, swirling at room temperature; 4 times with 40 ml, sonicating for 2 min at 65° C.; 1 time with 40 ml, swirling at room temperature. The implant was then placed into 5 ml of a 0.7 mM aqueous solution of 1,1,3,3-propane tetraphosphonic acid. The solution was placed in the ultrasonic bath and sonicated at 65° C. for 10 min. The implant was rinsed with water as follows: 2 times with 10 ml, swirling at room temperature; 1 time with 10 ml, sonicating for 2 min at 65° C.; 1 time with 10 ml, swirling at room temperature. The dental implant was dried in a desiccator over $P_2O_5$ and under vacuum (ca 20 mbar) for at least 3 hours.

Example 2

A ceramic disc (bulk composition atomic concentration Alumina 80%, Zirconia 20%; length 1.5 mm, diameter 10.0 mm) was provided with a smooth surface. The disc was immersed in 40 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 30 min. The disc was removed from the cleaning agent solution and rinsed with water as follows: 2 times with 50 ml, swirling at room temperature; 4 times with 50 ml, sonicating for 2 min at 65° C. The disc was then placed into 10 ml of a 0.7 mM aqueous solution of 1,1,3,3-propane tetraphosphonic acid. The solution was placed in the ultrasonic bath and sonicated at 65° C. for 60 min. The disc was rinsed with water as follows: 2 times with 10 ml, swirling at room temperature; 1 time with 10 ml, sonicating for 2 min at 65° C. The disc was dried in a desiccator over $P_2O_5$ and under vacuum (ca 20 mbar) for at least 3 hours.

Example 3

A ceramic dental implant (alumina toughened zirconia, yttria stabilized; length 11.0 mm, diameter 3.8 mm) was provided with a smooth surface. The dental implant was immersed in 50 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 70° C. for 15 min. This step was repeated a second time. The implant was removed from the cleaning agent solution and rinsed with water as follows: 2 times with 50 ml, swirling at room temperature; 3 times with 50 ml, sonicating for 2 min at 70° C. The implant was then placed into 15 ml of a 0.7 mM aqueous solution of 1,1,3,3-propane tetraphosphonic acid. The solution was placed in the ultrasonic bath and sonicated at 70° C. for 60 min. The implant was rinsed with water as follows: 1 time with 10 ml, swirling at room temperature; 2 times with 10 ml, sonicating for 2 min at 65° C.; 1 time with 10 ml, swirling at room temperature. The dental implant was dried in a desiccator over $P_2O_5$ and under vacuum (ca 20 mbar) for at least 3 hours.

Example 4

Ten Titanium grade 23 dental implants (bulk composition atomic concentration Titanium 90%, Aluminum 6%, Vanadium 4%; length 11.0 mm, diameter 3.75 mm) were provided with a roughened surface, produced by sand blasting and acid etching according to industry standards. The dental implants were immersed in 400 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 30 min. The implants were removed from the cleaning agent solution and rinsed with water as follows: 2 times with 400 ml, swirling at room temperature; 4 times with 400 ml, sonicating for 2 min at 65° C.; 1 time with 400 ml, swirling at room temperature. The implants were then placed one after the other into 5 ml of a 0.7 mM aqueous solution of 1,1,3,3-propane tetraphosphonic acid. The solution was placed in the ultrasonic bath and sonicated at 65° C. for 10 min. After the treatment with the phosphonic acid, each implant was rinsed with water as follows: 1 time with 10 ml, swirling at room temperature; 1 time with 10 ml, sonicating for 2 min at 65° C.; 1 time with 10 ml, swirling at room temperature. The dental implants were dried in a desiccator over $P_2O_5$ and under vacuum (ca 30 mbar) for at least 3 hours.

Example 5 (Comparative Example)

A Titanium grade 23 dental implant (bulk composition atomic concentration Titanium 90%, Aluminum 6%, Vanadium 4%; length 13.0 mm, diameter 3.75 mm) was provided with a roughened surface, produced by sand blasting and acid etching according to industry standards. The implant was immersed in 13 ml of a 0.7 mM aqueous solution of 1,1,3,3-propane tetraphosphonic acid. The solution was placed in an ultrasonic bath and sonicated at room temperature for 10 min. The implant was rinsed with water as follows: 1 time with 10 ml, swirling at room temperature; 2 times with 10 ml, sonicating for 1 min at room temperature. The dental implant was dried in a heating oven (ca 70° C.) for at least 1 hour. This surface treatment is in accordance with the surface treatment described in EP-A-1343545.

Example 6 (Comparative Example)

A ceramic disc (bulk composition atomic concentration Alumina 80%, Zirconia 20%; length 5.0 mm, diameter 15.0 mm) was provided with a smooth surface on one side and a roughened surface on the other side. The sample was immersed in 30 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at room temperature for 5 min. The solution was then removed and replaced by fresh 2% (v/v) aqueous solution of deconex 15 PF-x. Sonication was repeated at room temperature for 5 min. This cleaning step was repeated 4 times in total. The disc was removed from the cleaning agent solution and rinsed with water as follows: 6 times with 30 ml, sonicating for 5 min at room temperature. The water from the second to last rinse was tested and a pH greater than 6.2 was found. The disc was then placed into 20 ml of a 0.7 mM aqueous solution of 1,1,3,3-propane tetraphosphonic acid. The solution was swirled thoroughly and left to stand at room temperature for 30 min. It was briefly swirled again and left to stand for an additional 5 min. The disc was rinsed with water as follows: 3 times with 20 ml, swirling at room temperature. The ceramic disc was dried in a desiccator over $P_2O_5$ and under vacuum (ca 20 mbar) for at least 3 hours.

This surface treatment is in accordance with the surface treatment described in EP-A-1343545.

Example 7 (Comparative Example)

A ceramic disc (EZY95Bio-TZP, bulk composition atomic concentration Zirconia+Yttria+HfO$_2$=99.9%; length 5.0 mm, diameter 1.25 mm) was provided with a smooth surface. The sample was immersed in 30 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at room temperature for 5 min. The solution was then removed and replaced by fresh 2% (v/v) aqueous solution of deconex 15 PF-x. Sonication was repeated at room temperature for 5 min. This cleaning step was repeated 4 times in total. The sample was removed from the cleaning agent solution and rinsed with water as follows: 6 times with 65 ml, sonicating for 5 min at room temperature. The water from the second to last rinse was tested and a pH of 5.8 was found. The disc was rinsed again with water as follows: 4 times with 30 ml, sonicating for 5 min at room temperature. The water from the last rinse was tested and a pH of 5.9 was found. This was considered acceptable. The disc was then placed into 1.5 ml of a 0.7 mM aqueous solution of 1,1,3,3-propane tetraphosphonic acid. The solution was swirled thoroughly and left to stand at room temperature for 30 min. It was briefly swirled again and left to stand for an additional 5 min. The disc was rinsed with water as follows: 3 times with 20 ml, swirling at room temperature. The ceramic disc was dried in a desiccator over P$_2$O$_5$ and under vacuum (ca 20 mbar) for at least 3 hours. This surface treatment is in accordance with the surface treatment described in EP-A-1343545.

Example 8

Following the surface treatment with one phosphonic acid compound as described in Examples 1 to 7 the samples were analyzed by X-ray photoelectron spectroscopy (XPS). XPS analyses were performed on an Axis Ultra spectrometer from Kratos (Kratos, Manchester, U.K.) equipped with a concentric hemispherical analyzer and using a monochromatized aluminum anode X-ray source (Al K$\alpha_{1,2}$ 1486.6 eV, full width at half maximum, fwhm=0.85 eV, 15 kV, 150 W). The samples were investigated under ultrahigh vacuum conditions: $10^{-8}$-$10^{-7}$ Pa. Spectra were taken at a 90° takeoff angle with respect to the surface. A sample area of 300×700 µm$^2$ or 700×700 µm$^2$ was analyzed with a pass energy of 80.0 eV for survey scans. The spectrometer was calibrated by using Cu 2p3/2 (932.7 eV) and Au 4f7/2 (84.0 eV) signals. Surface sensitivity factors used to determine the atomic concentrations were those of the instrument. Spectra were peak fitted after background subtraction by assuming a Gaussian/Lorentzian (90-70/10-30) peak shape. All peaks between 0 eV to 1200 eV were inspected. The % atomic concentration of each element is shown in the table below.

| | % atomic concentration from survey spectra | | | | | | | |
|---|---|---|---|---|---|---|---|---|
| Element from survey[a] | Titanium Grade 23 dental implant (Ex. 1) | Titanium Grade 23 dental implant #8 (Ex. 4) | Titanium Grade 23 dental implant #10 (Ex. 4) | Titanium Grade 23 dental implant (Comp. Ex. 5) | Ceramic disc (Ex. 2) | Ceramic disc (Comp. Ex. 6) | Ceramic dental implant (Ex. 3) | Ceramic dental implant (Comp. Ex. 7) |
| Ti2p | 18.5 | 17.7 | 18.3 | 16.9 | 0.0 | 0.0 | 0.0 | 0.0 |
| Al2s | 2.3 | 1.8 | 3.1 | 2.4 | 19.0[b] | 27.0[b] | 8.8 | 0.0 |
| Zr3d | 0.0 | 0.0 | 0.0 | 0.0 | 6.5 | 4.6 | 14.1 | 20.4 |
| V2p | 0.4 | 0.4 | 0.5 | 0.5 | 0.0 | 0.0 | 0.0 | 0.0 |
| Y3d | 0.0 | 0.0 | 0.0 | 0.0 | 0.2 | 0.2 | 1.8 | 2.6 |
| Hf4d | 0.0 | 0.0 | 0.0 | 0.0 | 0.0 | 0.0 | 0.0 | 1.5 |
| O1s | 54.4 | 55.3 | 55.6 | 50.5 | 58.9 | 54.5 | 59.0 | 57.6 |
| C1s | 19.5 | 19.3 | 18.0 | 23.7 | 11.4 | 10.9 | 13.0 | 14.4 |
| P2p | 4.0 | 3.7 | 3.3 | 2.2 | 3.6 | 2.0 | 3.0 | 2.1 |
| Phosphorus/Metal | 0.18[c] | 0.18[c] | 0.15[c] | 0.11[c] | 0.14[d] | 0.06[d] | 0.12[e] | 0.08[f] |

[a] S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤1%.
[b] Al2p was measured.
[c] Metal = sum % atomic concentrations (Ti2p + Al2s + V2p)
[d] Metal = sum % atomic concentrations (Al2p + Zr3d)
[e] Metal = sum % atomic concentrations (Al2s + Zr3d + Y3d)
[f] Metal = sum % atomic concentrations (Zr3d + Y3d + Hf4d)

The phosphorus over metal ratio ("Phosphorus/Metal") was calculated dividing the % atomic concentration of phosphorus by the sum of the % atomic concentrations of all metals expected in the analyzed sample. When the phosphorus over metal ratios obtained with the surface treatment process according to the present invention (Examples 1 to 4) were compared to those obtained in Comparative Examples 5 to 7 (obtained in accordance with the surface treatment described in EP-A-1343545), it was found that the ratios obtained with the process according to the invention were significantly higher than those obtained in Comparative Examples 5 to 7, which indicates that a better surface coverage was obtained with the surface treatment process of the invention. The XPS results of the implants treated as per Example 4 furthermore showed that 5 ml of a 0.7 mM solution of 1,1,3,3-propane tetraphosphonic acid can be used to treat up to 8 dental implants.

Example 9

Ten Titanium grade 23 dental implants (bulk composition atomic concentration Titanium 90%, Aluminum 6%, Vanadium 4%; length 11.0 mm, diameter 3.75 mm) were provided with a roughened surface, produced by sand blasting and acid etching according to industry standards. The dental implants were immersed in 400 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 30 min. The implants were removed from the cleaning agent solution and rinsed with water as follows: 2 times with 400 ml, swirling at room temperature; 4 times with 400 ml, sonicating for 2 min at 65° C.; 1 time with 400 ml, swirling at room temperature. The implants were then placed by group of 2 into 5 ml of the following concentrations of 1,1,3,3-propane tetraphosphonic acid: 0.7 mM, 2 mM, 3.5 mM, 5 mM, 7 mM. The solutions were placed in the ultrasonic bath and sonicated at 65° C. for 10 min. After the treatment with the phosphonic acid, each implant was rinsed with water as follows: 2 times with 10 ml, swirling at room temperature; 1 time with 10 ml, sonicating for 2 min at 65° C.; 1 time with 10 ml, swirling at room temperature. The implants were dried in a desiccator over $P_2O_5$ and under vacuum (ca 30 mbar) for at least 3 hours. The samples were analyzed by X-ray photoelectron spectroscopy (XPS). Same analysis conditions as described in Example 8 were used. The % atomic concentration of each element is shown in the table below.

| | % atomic concentration from survey spectra | | | | |
|---|---|---|---|---|---|
| Element from survey[a] | Titanium Grade 23 dental implant (0.7 mM) | Titanium Grade 23 dental implant (2 mM) | Titanium Grade 23 dental implant (3.5 mM) | Titanium Grade 23 dental implant (5 mM) | Titanium Grade 23 dental implant (7 mM) |
| Ti2p | 18.5 | 18.6 | 19.0 | 19.2 | 19.2 |
| Al2s | 2.3 | 2.5 | 2.8 | 2.5 | 2.5 |
| V2p | 0.4 | 0.5 | 0.5 | 0.5 | 0.5 |
| O1s | 54.4 | 54.1 | 56.7 | 56.7 | 56.2 |
| C1s | 19.5 | 19.9 | 16.7 | 16.2 | 16.6 |
| P2p | 4.0 | 3.8 | 3.7 | 4.0 | 4.0 |
| Phosphorus/Metal[b] | 0.19 | 0.18 | 0.17 | 0.18 | 0.18 |

[a]Zr3d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration < 1%.
[b]Metal = sum % atomic concentrations (Ti2p + Al2s + V2p)

The phosphorus over metal ratio was calculated and was the same at each concentration tested. This indicated the formation of a full monolayer of phosphonic acid molecules at all concentrations.

Example 10

Four ceramic dental implants (alumina toughened zirconia, yttria stabilized; length 11.0 mm, diameter 3.8 mm) were provided with a smooth surface. The dental implants were immersed in 300 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 70° C. for 15 min. This step was repeated a second time. The implants were removed from the cleaning agent solution and rinsed with water as follows: 2 times with 300 ml, swirling at room temperature; 3 times with 300 ml, sonicating for 2 min at 70° C. The implants were then placed into 15 ml of the following concentrations of 1,1,3,3-propane tetraphosphonic acid: 0.7 mM, 2.5 mM, 5 mM, 10 mM. The solutions were placed in the ultrasonic bath and sonicated at 70° C. for 60 min. After treatment, the implants were rinsed with water as follows: 1 time with 10 ml, swirling at room temperature; 1 time with 10 ml, sonicating for 2 min at 70° C.; 1 time with 10 ml, swirling at room temperature. The implants were dried in a desiccator over $P_2O_5$ and under vacuum (ca 20 mbar) for at least 3 hours.

The samples were analyzed by X-ray photoelectron spectroscopy (XPS). Same analysis conditions as described in Example 8 were used. The % atomic concentration of each element is shown in the table below.

| | % atomic concentration from survey spectra | | | |
|---|---|---|---|---|
| Element from survey[a] | Ceramic dental implant (0.7 mM) | Ceramic dental implant (2.5 mM) | Ceramic dental implant (5 mM) | Ceramic dental implant (10 mM) |
| Al2s | 8.8 | 9.6 | 9.5 | 9.0 |
| Zr3d | 14.1 | 14.8 | 14.9 | 15.5 |
| Y3d | 1.8 | 1.8 | 1.7 | 1.7 |
| O1s | 59.0 | 56.5 | 57.8 | 58.8 |
| C1s | 13.0 | 13.4 | 12.4 | 11.6 |
| P2p | 3.0 | 3.1 | 2.9 | 3.2 |
| Phosphorus/Metal[b] | 0.12 | 0.12 | 0.11 | 0.12 |

[a]Ti2p, V2p, N1s, S2p, Ca2p, Cl2p, Na1s, K2p, Zn2p, Cu2p, Pb4f, Ni2p, Co2p, Cr2p, Fe2p, Mo3d, Mg2p and F1s were not detected. Si2p was detected at % atomic concentration < 1%.
[b]Metal = sum % atomic concentrations (Al2s + Zr3d + Y3d)

The phosphorus over metal ratio was calculated and was the same at each concentration tested. This indicated the formation of a full monolayer of phosphonic acid molecules at all concentrations.

Example 11

A Titanium grade 5 dental implant (bulk composition atomic concentration Titanium 90%, Aluminum 6%, Vanadium 4%; length 11.0 mm, diameter 3.75 mm) is provided with a roughened surface, produced by sand blasting and acid etching according to industry standards. The dental implant is immersed in 30 ml of a 2% (v/v) aqueous solution of deconex 15 PF-x (which is a phosphate free, potassium hydroxide based standard cleaning agent). The solution is placed in an ultrasonic bath (output frequency 30 kHz) and sonicated at 65° C. for 15 min. The implant is removed from the cleaning agent solution and rinsed with water as follows: 2 times with 30 ml, swirling at room temperature; 4 times with 30 ml, sonicating for 2 min at 65° C.; 1 time with 30 ml, swirling at room temperature. The implant is then placed into 5 ml of a 0.5 mM aqueous solution of one of the following phosphonic acids: propane-1-phosphonic acid (PA-1), propane-1,3-diphosphonic acid (PA-2), tert-butyl phosphonic acid (PA-3), 1-propene-3-phosphonic acid (PA-4), 1-cyclohexyl phosphonic acid (PA-5), phenyl-1-phosphonic acid (PA-6), diethylenetriamine penta(methylene phosphonic acid) (PA-7), 2-amino-3-phosphonopropionic acid (PA-8), 2-(2-phosphonoacetoxy)benzoic acid (PA-9), etidronic acid (PA-10). The solution is placed in the ultrasonic bath and sonicated at 65° C. for 10 min. The implant is rinsed with water as follows: 2 times with 10 ml, swirling at room temperature; 1 time with 10 ml, sonicating for 2 min at 65° C.; 1 time with 10 ml, swirling at room temperature. The dental implant is dried in a desiccator over $P_2O_5$ and under vacuum (ca 20 mbar) for at least 3 hours. The samples are analyzed by X-ray photoelectron spectroscopy (XPS). Same analysis conditions as described in Example 8 are used. The prospective % atomic concentration of each element is shown in the table below.

solution and rinsed with water as follows: 2 times with 10 ml, swirling at room temperature; 4 times with 10 ml, sonicating for 2 min at room temperature; 1 time with 10 ml, swirling at room temperature. The cylinders were then placed into 6 ml of a 0.7 mM aqueous solution of 1,1,3,3-propane tetraphosphonic acid. The solution was swirled thoroughly and left to stand at room temperature for 15 min. The cylinders were rinsed with water as follows: 2 times with 10 ml, swirling at room temperature; 1 time with 10 ml, sonicating for 2 min at room temperature; 1 time with 10 ml, swirling at room temperature. The cylinders were dried in a

| % atomic concentration from survey spectra (prospective data) | | | | | | | | | | |
|---|---|---|---|---|---|---|---|---|---|---|
| From survey[a] | PA-1 | PA-2 | PA-3 | PA-4 | PA-5 | PA-6 | PA-7 | PA-8 | PA-9 | PA-10 |
| Phosphorus/Metal[b] (surface treatment as described herein above) | 0.16-0.20 | 0.16-0.20 | 0.16-0.20 | 0.16-0.20 | 0.16-0.20 | 0.16-0.20 | 0.16-0.20 | 0.16-0.20 | 0.16-0.20 | 0.16-0.20 |
| Phosphorus/Metal (surface treatment as described in Comp. Example 6) | 0.05-0.11 | 0.05-0.11 | 0.05-0.11 | 0.05-0.11 | 0.05-0.11 | 0.05-0.11 | 0.05-0.11 | 0.05-0.11 | 0.05-0.11 | 0.05-0.11 |

[a]The XPS survey shows the expected elements (Ti2p, Al2s, V2p, O1s, C1s, P2p, N1s) for all compounds tested. Other elements Zr3d, Y3d, Si2p, S2p, Ca2p, Cl2p, Na1s, K2p, Zn2p, Cu2p, Pb4f, Ni2p, Co2p, Cr2p, Fe2p, Mo3d, Mg2p and F1s.
[b]Metal = sum % atomic concentrations (Ti2p + Al2s + V2p)

Example 12

Two Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were immersed in 6 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 15 min. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed into 6 ml of a 0.7 mM aqueous solution of 1,1,3,3-propane tetraphosphonic acid. The solution was placed in the ultrasonic bath and sonicated at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

Example 13 (Comparative Example)

Two Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were immersed in 6 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at room temperature for 15 min. The cylinders were removed from the cleaning agent desiccator over $P_2O_5$ and under vacuum (ca 20 mbar) for at least 3 hours. This surface treatment is in accordance with the surface treatment described in EP-A-1343545.

Example 14

Following the surface treatment with one phosphonic acid compound as described in Examples 12 and 13, the samples were analyzed by X-ray photoelectron spectroscopy (XPS). Same analysis conditions as described in Example 8 were used. The % atomic concentration of each element is shown in the table below.

| % atomic concentration from survey spectra (average of 2 analysis points) | | |
|---|---|---|
| Element from survey[a] | Titanium Grade 4 cylinder (Example 12) | Titanium Grade 4 cylinder (Example 13) |
| Ti2p | 16.4 | 17.7 |
| O1s | 53.5 | 48.2 |
| C1s | 24.0 | 30.7 |
| P2p | 4.0 | 2.6 |
| Phosphorus/Metal | 0.25[b] | 0.15[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤ 2.2%.
[b]Metal = sum % atomic concentrations (Ti2p)

The phosphorus over metal ratio ("Phosphorus/Metal") was calculated and it was found that the ratio obtained with the process according to the present invention (Example 12) was significantly higher than that obtained with the comparative process described in Example 13, as also illustrated in FIG. 1. This indicates that a better surface coverage was obtained with the surface treatment process of the invention.

Example 15

Twelve Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed by 2 into 6 glass bottles and immersed in 6 ml of a 2% (v/v) aqueous solution of deconex 15 PF-x (which is a phosphate free, potassium hydroxide based standard cleaning agent). The 6 solutions were placed in an ultrasonic bath (output frequency 30 kHz) and sonicated at 40° C., 50° C., 60° C., 70° C., 80° C. and 90° C., respectively, for 15 min. The cylinders were removed from the cleaning agent solution and rinsed with water as follows: 2 times with 10 ml, swirling at room temperature; 4 times with 10 ml, sonicating for 2 min at 40° C., 50° C., 60° C., 70° C., 80° C. and 90° C., respectively; 1 time with 10 ml, swirling at room temperature. The cylinders were then placed by 2 into 6 glass bottles and immersed in 6 ml of a 0.7 mM aqueous solution of 1,1,3,3-propane tetraphosphonic acid. The 6 solutions were placed in the ultrasonic bath and sonicated at 40° C., 50° C., 60° C., 70° C., 80° C. and 90° C., respectively, for 15 min. The cylinders were rinsed with water as follows: 2 times with 10 ml, swirling at room temperature; 1 time with 10 ml, sonicating for 2 min at 40° C., 50° C., 60° C., 70° C., 80° C. and 90° C., respectively; 1 time with 10 ml, swirling at room temperature. The cylinders were dried in a desiccator over $P_2O_5$ and under vacuum (ca 20 mbar) for at least 3 hours.

The samples were then analyzed by X-ray photoelectron spectroscopy (XPS). Same analysis conditions as described in Example 8 were used. The % atomic concentration of each element is shown in the table below.

| % atomic concentration from survey spectra (average of 2 analysis points) | | | | | | |
|---|---|---|---|---|---|---|
| Element from survey[a] | 40° C. | 50° C. | 60° C. | 70° C. | 80° C. | 90° C. |
| Ti2p | 17.9 | 17.3 | 17.0 | 16.6 | 16.6 | 15.7 |
| O1s | 50.9 | 51.1 | 51.9 | 52.6 | 51.2 | 50.7 |
| C1s | 27.0 | 26.4 | 26.0 | 25.7 | 27.1 | 28.2 |
| P2p | 3.9 | 4.5 | 4.2 | 4.1 | 4.5 | 4.3 |
| Phosphorus/Metal | 0.22[b] | 0.26[b] | 0.25[b] | 0.25[b] | 0.27[b] | 0.27[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤1.0%.
[b]Metal = sum % atomic concentrations (Ti2p)

The phosphorus over metal ratio ("Phosphorus/Metal") was calculated and it was found that a better surface coverage was obtained at a temperature ≥50° C. This is also illustrated in FIG. 2.

Example 16

Six Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed by 2 into 3 glass bottles and immersed in 6 ml of a 2% (v/v) aqueous solution of deconex 15 PF-x (which is a phosphate free, potassium hydroxide based standard cleaning agent). The 3 solutions were placed in an ultrasonic bath (output frequency 30 kHz) and sonicated at 65° C. for 5, 15 and 30 min, respectively. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed by 2 into 3 glass bottles and immersed in 6 ml of a 0.7 mM aqueous solution of 1,1,3,3-propane tetraphosphonic acid. The 3 solutions were placed in the ultrasonic bath and sonicated at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

The samples were then analyzed by X-ray photoelectron spectroscopy (XPS). Same analysis conditions as described in Example 8 were used. The % atomic concentration of each element is shown in the table below.

| % atomic concentration from survey spectra (average of 2 analysis points) | | | |
|---|---|---|---|
| Element from survey[a] | Deconex 15PF-x 5 min | Deconex 15PF-x 15 min | Deconex 15PF-x 30 min |
| Ti2p | 14.6 | 15.8 | 15.7 |
| O1s | 51.0 | 51.7 | 51.6 |
| C1s | 27.9 | 26.4 | 27.0 |
| P2p | 5.3 | 5.1 | 4.9 |
| Phosphorus/Metal | 0.36[b] | 0.32[b] | 0.32[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤ 1.2%.
[b]Metal = sum % atomic concentrations (Ti2p)

The phosphorus over metal ratio ("Phosphorus/Metal") was calculated and it was found that a better surface coverage was obtained when the pre-treatment with deconex 15 PF-x is carried out for 5 min with sonication. This is also shown in FIG. 3.

Example 17

Eight Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed by 2 into 4 glass bottles and immersed in 6 ml of a 2% (v/v) aqueous solution of deconex 15 PF-x (which is a phosphate free, potassium hydroxide based standard cleaning agent). The 4 solutions were placed in an ultrasonic bath (output frequency 30 kHz) and sonicated at 65° C. for 15 min. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed by 2 into 4 glass bottles and immersed in 6 ml of a 0.7 mM aqueous solution of 1,1,3,3-propane tetraphosphonic acid. The 4 solutions were placed in the ultrasonic bath and sonicated at 65° C. for 5, 10, 30 and 60 min, respectively. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

The samples were then analyzed by X-ray photoelectron spectroscopy (XPS). Same analysis conditions as described in Example 8 were used. The % atomic concentration of each element is shown in the table below.

| % atomic concentration from survey spectra (average of 2 analysis points) | | | | |
|---|---|---|---|---|
| Element from survey[a] | Phosphonic acid 5 min | Phosphonic acid 10 min | Phosphonic acid 30 min | Phosphonic acid 60 min |
| Ti2p | 17.0 | 16.4 | 16.3 | 16.8 |
| O1s | 50.9 | 51.4 | 52.4 | 52.3 |
| C1s | 27.0 | 26.7 | 25.7 | 25.3 |
| P2p | 4.1 | 4.5 | 4.8 | 4.8 |
| Phosphorus/Metal | 0.24[b] | 0.28[b] | 0.30[b] | 0.28[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤ 1.0%.
[b]Metal = sum % atomic concentrations (Ti2p)

The phosphorus over metal ratio ("Phosphorus/Metal") was calculated and it was found that a better surface coverage was obtained when the treatment with the phosphonic acid is carried out from 10 to 60 min with sonication. This is also shown in FIG. 4.

Example 18

Two Cobalt Chrome discs (bulk composition atomic concentration Cobalt 64%, Chrome 28%, Molybdenum 6%, other elements 2%; length 1.5 mm, diameter 5.0 mm) were provided with a machined surface. The 2 discs were placed into a glass bottle and immersed in 6 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 65° C. for 15 min. The discs were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The discs were then placed into a glass bottle and immersed in 4 ml of a 0.7 mM aqueous solution of 1,1,3,3-propane tetraphosphonic acid. The solution was placed in the ultrasonic bath and sonicated at 65° C. for 15 min. The discs were rinsed with water as follows: 2 times with 10 ml, swirling at room temperature; 1 time with 10 ml, sonicating for 2 min at 65° C.; 1 time with 10 ml, swirling at room temperature. The discs were dried in a desiccator over $P_2O_5$ and under vacuum (ca 20 mbar) for at least 3 hours.

Example 19 (Comparative Example)

Two Cobalt Chrome discs (bulk composition atomic concentration Cobalt 64%, Chrome 28%, Molybdenum 6%, other elements 2%; length 1.5 mm, diameter 5.0 mm) were provided with a machined surface. The 2 discs were placed into a glass bottle and immersed in 6 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at room temperature for 15 min. The discs were removed from the cleaning agent solution and rinsed with water as follows: 2 times with 10 ml, swirling at room temperature; 4 times with 10 ml, sonicating for 2 min at room temperature; 1 time with 10 ml, swirling at room temperature. The discs were then placed into a glass bottle and immersed in 4 ml of a 0.7 mM aqueous solution of 1,1,3,3-propane tetraphosphonic acid. The solution was swirled thoroughly and left to stand at room temperature for 15 min. The discs were rinsed with water as follows: 2 times with 10 ml, swirling at room temperature; 1 time with 10 ml, sonicating for 2 min at room temperature; 1 time with 10 ml, swirling at room temperature. The discs were dried in a desiccator over $P_2O_5$ and under vacuum (ca 20 mbar) for at least 3 hours. This surface treatment is in accordance with the surface treatment described in EP-A-1343545.

Example 20

Following the surface treatment with one phosphonic acid compound as described in Examples 18 and 19, the samples were analyzed by X-ray photoelectron spectroscopy (XPS). Same analysis conditions as described in Example 8 were used. The % atomic concentration of each element is shown in the table below.

| % atomic concentration from survey spectra (average of 2 analysis points) | | |
|---|---|---|
| Element from survey[a] | Cobalt Chrome disc (Example 18) | Cobalt Chrome disc (Example 19) |
| Cr2p | 12.2 | 11.0 |
| Co2p | 8.6 | 8.6 |
| Mo3d | 1.5 | 1.5 |
| O1s | 29.5 | 24.8 |
| C1s | 39.6 | 47.3 |
| P2p | 1.7 | 0.0 |
| Phosphorus/Metal | 0.08[b] | 0.00[b] |

[a]Al2p, Zr3d, V2p, Y3d, Hf4d, Si2p, Ca2p, Cl2p, Na1s, K2p, Zn2p, Cu2p, Pb4f, Ni2p, Fe2p, Ti2p, Mg2p and F1s were not detected. N1s and S2p were detected at % atomic concentration ≤ 7.0%.
[b]Metal = sum % atomic concentrations (Cr2p + Co2p + Mo3d)

The phosphorus over metal ratio ("Phosphorus/Metal") was calculated and it was found that the ratio obtained with the process according to the present invention (Example 18) was significantly higher than that obtained with the comparative process described in Example 19, which indicates that a better surface coverage was obtained with the surface treatment process of the invention. This is also illustrated in FIG. 5.

Example 21

Twelve Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed by 2 into 6 glass bottles and immersed in 6 ml of a 2% (v/v) aqueous solution of deconex 15 PF-x (which is a phosphate free, potassium hydroxide based standard cleaning agent). The 6 solutions were placed in an ultrasonic bath (output frequency 30 kHz) and sonicated at 65° C. for 15 min. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed by 2 into 6 glass bottles and immersed in 6 ml of the phosphonic acid compound described in the table below at the reported concentrations. The 6 solutions were placed in the ultrasonic bath and sonicated at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

The samples were then analyzed by X-ray photoelectron spectroscopy (XPS). Same analysis conditions as described in Example 8 were used. The % atomic concentration of each element is shown in the table below.

| | % atomic concentration from survey spectra (average of 2 analysis points) | | | | | |
|---|---|---|---|---|---|---|
| Element from survey[a] | Propane-1-phosphonic acid (A) | t-Butyl phosphonic acid (B) | Phenyl-1-phosphonic acid (C) | Diethylenetriamine penta(methylene phosphonic acid) (D) | Etidronic acid (E) | Methylene-1,1-di phosphonic acid (F) |
| Concentration (mM) | 2 | 2 | 2 | 0.4 | 1 | 1 |
| Ti2p | 21.9 | 21.8 | 21.9 | 19.3 | 21.4 | 20.5 |
| O1s | 50.8 | 50.0 | 50.3 | 51.9 | 52.2 | 52.4 |
| C1s | 26.5 | 27.5 | 26.9 | 22.8 | 24.4 | 24.7 |
| P2p | 0.5 | 0.4 | 0.7 | 3.0 | 2.0 | 2.2 |
| Phosphorus/Metal | 0.02[b] | 0.02[b] | 0.03[b] | 0.16[b] | 0.09[b] | 0.10[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤0.3%.
[b]Metal = sum % atomic concentrations (Ti2p)

The phosphorus over metal ratio ("Phosphorus/Metal") was calculated and it was found that using the process according to the present invention, titanium cylinders could be successfully treated with a variety of phosphonic acid compounds.

Example 22

Three Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed in 3 glass bottles and immersed in 5 ml of a 2% (v/v) aqueous solution of deconex 15 PF-x (which is a phosphate free, potassium hydroxide based standard cleaning agent). The solutions were placed in an ultrasonic bath (output frequency 30 kHz) and sonicated at 65° C. for 15 min. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed into 3 glass bottles and immersed into 3 ml of a 0.7 mM aqueous solution of 1,1,3,3-propane tetraphosphonic acid. The solutions were placed in the ultrasonic bath and sonicated at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

Example 23

Three Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed in 3 glass bottles and immersed in 5 ml of a 2% (v/v) aqueous solution of deconex 15 PF-x (which is a phosphate free, potassium hydroxide based standard cleaning agent). The solutions were placed in an ultrasonic bath (output frequency 30 kHz) and sonicated at 65° C. for 15 min. The cylinders were removed from the cleaning agent solution and rinsed with water as follows: 2 times with 10 ml, swirling at room temperature; 4 times with 10 ml, sonicating for 2 min at 65° C.; 1 time with 10 ml, swirling at room temperature. The cylinders were then placed into 3 glass bottles and immersed into 3 ml of a 0.7 mM aqueous solution of 1,1,3,3-propane tetraphosphonic acid. The solutions were swirled thoroughly and left to stand at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

Example 24

Following the surface treatment with one phosphonic acid compound as described in Examples 22 and 23, the samples were analyzed by X-ray photoelectron spectroscopy (XPS). Same analysis conditions as described in Example 8 were used. The % atomic concentration of each element is shown in the table below.

| | % atomic concentration from survey spectra (average of 6 analysis points) | |
|---|---|---|
| Element from survey[a] | Titanium Grade 4 cylinder (Example 22) | Titanium Grade 4 cylinder (Example 23) |
| Ti2p | 17.7 | 18.1 |
| O1s | 53.0 | 53.0 |
| C1s | 23.1 | 23.1 |
| P2p | 4.9 | 4.0 |
| Phosphorus/Metal | 0.28[b] | 0.22[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤ 1.7%.
[b]Metal = sum % atomic concentrations (Ti2p)

The phosphorus over metal ratio ("Phosphorus/Metal") was calculated and it was found that using sonication during the surface treatment with the phosphonic acid compound (Example 22) led to a better surface coverage when compared to the surface treatment with the phosphonic acid compound whereby sonication was not carried out (Example 23).

Example 25

Three Titanium grade 4 cylinders (bulk composition atomic concentration Titanium 100%; length 6.0 mm, diameter 2.4 mm) were provided with a roughened surface, produced by sand blasting and acid etching according to industry standards. The cylinders were placed in 3 glass bottles and immersed in 3 ml of a 0.7 mM aqueous solution of 1,1,3,3-propane tetraphosphonic acid. The solutions were placed in an ultrasonic bath (output frequency 30 kHz) and sonicated at 65° C. for 15 min. The cylinders were rinsed with water as follows: 2 times with 10 ml, swirling at room temperature; 1 time with 10 ml, sonicating for 2 min at 65° C.; 1 time with 10 ml, swirling at room temperature. The cylinders were dried in a desiccator over $P_2O_5$ and under vacuum (ca 20 mbar) for at least 3 hours.

Example 26

Following the surface treatment with one phosphonic acid compound as described in Examples 22 and 25, the samples were analyzed by X-ray photoelectron spectroscopy (XPS). Same analysis conditions as described in Example 8 were used. The % atomic concentration of each element is shown in the table below.

% atomic concentration from survey spectra (average of 6 analysis points)

| Element from survey[a] | Titanium Grade 4 cylinder (Example 22) | Titanium Grade 4 cylinder (Example 25) |
|---|---|---|
| Ti2p | 17.7 | 17.3 |
| O1s | 53.0 | 51.6 |
| C1s | 23.1 | 25.4 |
| P2p | 4.9 | 4.2 |
| Phosphorus/Metal | 0.28[b] | 0.24[b] |

[a]Al2p, Zr3d, V2p, Y3d, Hf4d, S2p, Ca2p, Cl2p, Na1s, K2p, Zn2p, Cu2p, Pb4f, Ni2p, Co2p, Cr2p, Fe2p, Mo3d, Mg2p and F1s were not detected. N1s and Si2p were detected at % atomic concentration ≤ 1.4%.
[b]Metal = sum % atomic concentrations (Ti2p)

The phosphorus over metal ratio ("Phosphorus/Metal") was calculated and it was found that pre-treatment with deconex 15 PF-x enhances surface coverage (Example 22) when compared to the surface treatment whereby deconex 15 PF-x was not used (Example 25).

Example 27

Two ceramic discs (yttria stabilized zirconia; length 5.0 mm, diameter 1.0 mm) were provided with a roughened surface, produced by sand blasting and acid etching according to industry standards. The discs were immersed in 80 ml of a 2% (v/v) aqueous solution of deconex 15 PF-x (which is a phosphate free, potassium hydroxide based standard cleaning agent). The solution was placed in an ultrasonic bath (output frequency 30 kHz) and sonicated at 70° C. for 15 min. This step was repeated a second time. The discs were removed from the cleaning agent solution and rinsed with water as follows: 2 times with 90 ml, swirling at room temperature; 3 times with 90 ml, sonicating for 2 min at 70° C. The discs were then placed into 2 glass bottles and immersed into 2.5 ml of a 0.7 mM aqueous solution of 1,1,3,3-propane tetraphosphonic acid. The solutions were placed in the ultrasonic bath and sonicated at 70° C. for 60 min. The discs were rinsed with water as follows: 1 time with 10 ml, swirling at room temperature; 1 time with 10 ml, sonicating for 2 min at 65° C.; 1 time with 10 ml, swirling at room temperature. The discs were dried in a desiccator over $P_2O_5$ and under vacuum (ca 20 mbar) for at least 3 hours.

Following the surface treatment, the thickness of the phosphonic acid layer was determined by depth profiling using XPS. Ion gun sputtering cycles were alternated with XPS measurements. An ion gun was used to etch the material for a defined period of time. Once turned off, XPS spectra were acquired. The depth profiles were performed using a Kratos AXIS Nova high resolution spectrometer. An Al-standard source was used for the measurement. Depth profile sputtering was performed by scanning a 3.8 keV Ar+ beam at 100 µA extractor current over an area of 4 mm×4 mm. The sputter rate of $Ta_2O_5$ standards measured under these conditions (6 nm/min) was used to convert sputter time in approximate sputter depth. Spectra were measured after the following sputtering times: 0, 5, 10, 15, 20, 30, 40, 60 sec. Spectra were peak fitted after background subtraction by assuming a Gaussian/Lorentzian (90-70/10-30) peak shape. All peaks between 0 eV to 1200 eV were inspected. The % atomic concentration of each element is shown in the table below.

% atomic concentration from survey spectra (average of 2 analysis points)

| Element from survey[a] | 0 sec | 5 sec | 10 sec | 15 sec | 20 sec | 30 sec | 40 sec | 60 sec |
|---|---|---|---|---|---|---|---|---|
| Depth (nm) | 0 | 0.5 | 1 | 1.5 | 2 | 3 | 4 | 6 |
| Zr3d | 18.0 | 29.4 | 29.9 | 30.6 | 31.4 | 26.8 | 27.4 | 32.7 |
| Y3d | 0.7 | 0.9 | 1.0 | 1.2 | 1.1 | 1.2 | 1.2 | 1.3 |
| O1s | 56.4 | 65.7 | 67.2 | 66.2 | 66.4 | 71.4 | 71.1 | 66.0 |
| C1s | 20.9 | 3.0 | 1.2 | 1.3 | 0.5 | 0.0 | 0.0 | 0.0 |
| P2p | 3.4 | 1.0 | 0.8 | 0.7 | 0.5 | 0.6 | 0.3 | 0.1 |
| Phosphorus/Metal | 0.18[b] | 0.03[b] | 0.02[b] | 0.02[b] | 0.01[b] | 0.02[b] | 0.01[b] | 0.00[b] |

[a]Al2p, V2p, Hf4d, S2p, Ca2p, Cl2p, Si2p, Na1s, K2p, Zn2p, Cu2p, Pb4f, Ni2p, Co2p, Cr2p, Fe2p, Mo3d and Mg2p were not detected. N1s and F1s were detected at % atomic concentration ≤0.5%.
[b]Metal = sum % atomic concentrations (Zr3d + Y3d)

These results show that the phosphonic acid compound binds to the outermost surface of the discs. The phosphorus peak was measured at % atomic concentrations close to the detection limit (0.5%) after 10 seconds of sputtering. This indicated that the phosphonic acid compound formed a monolayer with a thickness of about 1 nm (which is the size of the molecule). This is also shown in FIG. 6.

---

The invention claimed is:

1. A process of treating an implant, the process comprising the following step:
   treating the surface of the implant with at least one phosphonic acid compound or a pharmaceutically acceptable salt, ester or amide thereof under sonication at a temperature of about 50° C. to about 90° C.;
   wherein the process further comprises, before the step of treatment with the phosphonic acid compound, a step of pre-treating the surface of the implant with a cleaning agent, wherein the cleaning agent is a 0.5% (v/v) to 5% (v/v) aqueous solution of an alkaline phosphate-free liquid concentrate, wherein the liquid concentrate has a pH greater than 12 and comprises about 5% (w/w) to about 15% (w/w) of methylglycinediacetate and about 1% (w/w) to about 5% (w/w) of an inorganic base, and wherein said 0.5% (v/v) to 5% (v/v) aqueous solution has a pH equal to or greater than 11.

2. The process of claim 1, wherein the step of treatment with the phosphonic acid compound is conducted under sonication at a temperature of about 60° C. to about 70° C.

3. The process of claim 1, wherein the step of pre-treatment with the cleaning agent is conducted at a temperature of about 50° C. to about 90° C.

4. The process of claim 1, wherein the step of pretreatment with the cleaning agent is conducted under sonication.

5. The process of claim 1, wherein the phosphonic acid compound is a $C_{1-30}$ hydrocarbon which is substituted with 1 to 6 phosphonic acid groups, wherein said hydrocarbon is optionally substituted with one or more groups independently selected from the group consisting of hydroxy and halogen, and further wherein one or more carbon atoms comprised in said hydrocarbon are optionally each replaced by a heteroatom independently selected from the group consisting of nitrogen, oxygen and sulfur.

6. The process of claim 1, wherein the phosphonic acid compound is a $C_{1-15}$ hydrocarbon which is substituted with 1 to 6 phosphonic acid groups.

7. The process of claim 6, wherein said hydrocarbon is substituted with 3 to 6 phosphonic acid groups.

8. The process of claim 1, wherein the phosphonic acid compound is a $C_{1-10}$ alkane which is substituted with 3 to 6 phosphonic acid groups.

9. The process of claim 1, wherein the phosphonic acid compound is a linear $C_{2-6}$ alkane which is substituted with 3 or 4 phosphonic acid groups.

10. The process of claim 1, wherein the phosphonic acid compound is selected from the group consisting of methanephosphonic acid, ethanephosphonic acid, propane-1-phosphonic acid, propane-2-phosphonic acid, methane-1,1-diphosphonic acid, ethane-1,1-diphosphonic acid, ethane-1,2-diphosphonic acid, propane-1,1-diphosphonic acid, propane-2,2-diphosphonic acid, propane-1,2-diphosphonic acid, propane-1,3-diphosphonic acid, ethane-1,1,1-triphosphonic acid, ethane-1,1,2-triphosphonic acid, propane-1,1,1-triphosphonic acid, propane-1,1,2-triphosphonic acid, propane-1,1,3-triphosphonic acid, propane-1,2,2-triphosphonic acid, propane-1,2,3-triphosphonic acid, butane-1,1,1-triphosphonic acid, butane-1,1,2-triphosphonic acid, butane-1,1,3-triphosphonic acid, butane-1,1,4-triphosphonic acid, butane-1,2,2-triphosphonic acid, butane-2,2,3-triphosphonic acid, butane-1,3,3-triphosphonic acid, butane-1,2,3-triphosphonic acid, butane-1,2,4-triphosphonic acid, pentane-1,1,5-triphosphonic acid, pentane-2,2,5-triphosphonic acid, hexane-1,1,6-triphosphonic acid, hexane-2,2,6-triphosphonic acid, propane-1,1,1,2-tetraphosphonic acid, propane-1,1,1,3-tetraphosphonic acid, propane-1,1,2,2-tetraphosphonic acid, propane-1,1,2,3-tetraphosphonic acid, propane-1,1,3,3-tetraphosphonic acid, propane-1,2,2,3-tetraphosphonic acid, butane-1,1,4,4-tetraphosphonic acid, pentane-1,1,5,5-tetraphosphonic acid, hexane-1,1,6,6-tetraphosphonic acid, heptane-1,4,4,7-tetraphosphonic acid, octane-1,4,4,8-tetraphosphonic acid, nonane-1,5,5,9-tetraphosphonic acid, pentane-1,1,3,5,5-pentaphosphonic acid, pentane-1,1,2,4,5,5-hexaphosphonic acid, tert-butyl phosphonic acid, 2-methyl-propane-1,1,1-triphosphonic acid, 2-methyl-propane-1,1,3-triphosphonic acid, 2-(phosphono-methyl)-propane-1,3-diphosphonic acid, 2-methyl-propane-1,1,3,3-tetraphosphonic acid, 2-methyl-butane -1,1,1-triphosphonic acid, 3-methyl-butane-1,1,1-triphosphonic acid, 2-(phosphono -methyl)-propane-1,1-diphosphonic acid, 2-methyl-butane-1,1,3-triphosphonic acid, 2-methyl-butane-1,1,4-triphosphonic acid, 3-methyl-butane-2,2,4-triphosphonic acid, 3-methyl-butane-1,1,4-triphosphonic acid, 2-(phosphono-methyl)-butane-1,3-diphosphonic acid, 2-(phosphono-methyl)-butane-1,4-diphosphonic acid, 3-methyl-butane-1,1,2-triphosphonic acid, 2-methyl-butane-1,1,4,4-tetraphosphonic acid, 2-methyl-pentane -1,1,1-triphosphonic acid, 2-(phosphono-methyl)-pentane-1,1-diphosphonic acid, 2-methyl-pentane-1,1,3-triphosphonic acid, 2-methyl-pentane-1,1,4-triphosphonic acid, 2-methyl-pentane-1,1,5-triphosphonic acid, 2-methyl-pentane-1,3,3-triphosphonic acid, 4-methyl-pentane-2,2,5-triphosphonic acid, 4-methyl-pentane- 1,1,5-triphosphonic acid, 2-(phosphono-methyl)-pentane-1,3-diphosphonic acid, 2-methyl-pentane- 1,3,4-triphosphonic acid, 2-(phosphono-methyl)-pentane-1,4-diphosphonic acid, 2-(phosphono -methyl)-pentane-1,5-diphosphonic acid, 2-methyl-pentane-1,3,5-triphosphonic acid, 4-methyl-pentane-1,2,5-triphosphonic acid, 2-methyl-pentane-1,1,5,5-tetraphosphonic acid, 3-methyl-pentane-1,1,1-triphosphonic acid, 3-methyl-pentane-1,1,2-triphosphonic acid, 3-(phosphono-methyl)-pentane-1,1-diphosphonic acid, 3-methyl-pentane-1,1,5-triphosphonic acid, 3-(triphosphono-methyl)-pentane, 3-(phosphono-methyl)-pentane -1,5-diphosphonic acid, 3-methyl-pentane-2,2,5-triphosphonic acid, 2-methyl-hexane -1,1,1-triphosphonic acid, 2-(phosphono-methyl)-hexane-1,6-diphosphonic acid, 2-methyl-hexane-1,1,6,6-tetraphosphonic acid, 4-methyl-heptane-1,1,1-triphosphonic acid, 4-methyl-heptane-1,1,6,6-tetraphosphonic acid, 2-methyl-octane-1,1,1-triphosphonic acid, 2-methyl-octane-1,1,8,8-tetraphosphonic acid, 3-(bisphosphono -methyl)-butane-1,1,4,4-tetraphosphonic acid, 3-(bisphosphono-methyl)-pentane-1,1,5,5-tetraphosphonic acid, diethylenetriamine penta(methylene phosphonic acid), vinyl phosphonic acid, 1-propene-3-phosphonic acid, 2-propene-3-phosphonic acid, 1-propene -2-phosphonic acid, ethene-1,1-diphosphonic acid, ethene-1,2-diphosphonic acid, 1-propene-1,1-diphosphonic acid, 1-propene-3,3-diphosphonic acid, 1-propene-1,2-diphosphonic acid, 1-propene-2,3-diphosphonic acid, 1-propene-1,3-diphosphonic acid, 1-ethene-1,1,2-triphosphonic acid, 1-propene-3,3,3-triphosphonic acid, 1-propene-1,1,2-triphosphonic acid, 1-propene-2,3,3-triphosphonic acid, 1-propene-1,1,3-triphosphonic acid, 1-propene-1,3,3-triphosphonic acid, 1-propene-1,2,3-triphosphonic acid, 1-butene -4,4,4-triphosphonic acid, 2-butene-4,4,4-triphosphonic acid, 1-butene-1,1,2-triphosphonic acid, 2-butene-3,4,4-triphosphonic acid, 1-butene-3,4,4-triphosphonic acid, 1-butene -1,1,3-triphosphonic acid, 2-butene-1,1,3-triphosphonic acid, 1-butene-2,4,4-triphosphonic acid, 1-butene-1,1,4-triphosphonic acid, 2-butene-1,1,4-triphosphonic acid, 1-butene -1,4,4-triphosphonic acid, 1-butene-3,3,4-triphosphonic acid, 1-butene-2,3,3-triphosphonic acid, 1-butene-1,3,3-triphosphonic acid, 1-butene-1,2,3-triphosphonic acid, 2-butene -2,3,4-triphosphonic acid, 1-butene-2,3,4-triphosphonic acid, 1-butene-1,2,4-triphosphonic acid, 2-butene-1,2,4-triphosphonic acid, 1-butene-1,3,4-triphosphonic acid, 2-pentene -1,1,5-triphosphonic acid, 2-pentene-1,5,5-triphosphonic acid, 1-pentene-1,5,5-triphosphonic acid, 2-pentene-1,4,4-triphosphonic acid, 1-pentene-1,4,4-triphosphonic acid, 1-hexene-1,1,6-triphosphonic acid, 2-hexene-1,1,6-triphosphonic acid, 3-hexene -1,1,6-triphosphonic acid, 2-hexene-1,6,6-triphosphonic acid, 1-hexene-1,6,6-triphosphonic acid, 1-hexene-1,5,5-triphosphonic acid, 2-hexene-1,5,5-triphosphonic acid, 3-hexene-2,2,6-triphosphonic acid, 1-propene-2,3,3,3-tetraphosphonic acid, 1-propene-1,3,3,3-tetraphosphonic acid, 1-propene-1,2,3,3-tetraphosphonic acid, 1-propene-1,1,3,3-tetraphosphonic acid, 1-butene-1,1,4,4-tetraphosphonic acid, 2-butene -1,1,4,4-tetraphosphonic acid, 1-pentene-1,1,5,5-tetraphosphonic acid, 2-pentene-1,1,5,5-tetraphosphonic acid, 1-hexene-1,1,6,6-tetraphosphonic acid, 2-hexene-1,1,6,6-tetraphosphonic acid, 3-hexene-1,1,6,6-tetraphosphonic acid, 1-heptene-1,4,4,7-tetraphosphonic acid, 2-heptene-1,4,4,7-tetraphosphonic acid, 1-octene-1,4,4,8-tetraphosphonic acid, 2-octene-1,4,4,8-tetraphosphonic acid, 3-octene-1,5,5,8-tetraphosphonic acid, 1-nonene-1,5, 5,9-tetraphosphonic acid, 2-nonene-1,5,5,9-tetraphosphonic acid, 3-nonene-1,5,5,9-tetraphosphonic acid, 1-cyclopentyl-phosphonic acid, 1,1-cyclopentyl-diphosphonic acid, 1,2-cyclopentyl-diphosphonic acid, 1,3-cyclopentyl-diphosphonic acid, 1-cyclohexyl-phosphonic acid, 1,1-cyclohexyl-diphosphonic acid, 1,2-cyclohexyl-diphosphonic acid, 1,3-cyclohexyl-diphosphonic acid, 1,4-cyclohexyl-diphosphonic acid, and phenyl-1-phosphonic acid.

11. The process of claim 1, wherein the phosphonic acid compound is propane-1,1,3,3-tetraphosphonic acid.

12. The process of claim 1, wherein the implant is a dental abutment, a coronary stent, a dental implant, a hip implant, a spinal implant, a small joints implant, a shoulder implant, or a knee implant.

13. The process of claim 1, wherein the surface of the implant is made of titanium, chromium, niobium, tantalum, vanadium, zirconium, aluminum, cobalt, nickel, stainless steel, or an alloy of any of the aforementioned metals.

14. The process of claim 1, wherein the surface of the implant is made of titanium or a titanium alloy.

15. The process of claim 1, wherein the surface of the implant is made of a cobalt-chromium alloy.

16. The process of claim 1, wherein the surface of the implant is made of a ceramic which is an oxide, a carbide, a nitride, an oxynitride, a carbonitride, or an oxycarbide of a metal or of a metal alloy, wherein said metal or metal alloy is selected from the group consisting of titanium, chromium, niobium, tantalum, vanadium, zirconium, aluminum, cobalt, nickel, stainless steel, and alloys thereof.

* * * * *

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 1

Gly Arg Gly Asp
1

<210> SEQ ID NO 2
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 2

Arg Gly Asp Glu
1

<210> SEQ ID NO 3
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 3

Arg Gly Asp Thr
1

<210> SEQ ID NO 4
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 4

Arg Gly Asp Ser
1

<210> SEQ ID NO 5
<211> LENGTH: 5
<212> TYPE: PRT
<213> ORGANISM: Artificial Sequence
<220> FEATURE:
<223> OTHER INFORMATION: RGD-containing peptide

<400> SEQUENCE: 5

Gly Arg Gly Asp Ser
1               5

<210> SEQ ID NO 6
<211> LENGTH: 6

```
<212> TYPE: PRT
<213> ORGANISM: Artificial Sequence
<220> FEATURE:
<223> OTHER INFORMATION: RGD-containing peptide

<400> SEQUENCE: 6

Gly Arg Gly Asp Ser Pro
1               5

<210> SEQ ID NO 7
<211> LENGTH: 7
<212> TYPE: PRT
<213> ORGANISM: Artificial Sequence
<220> FEATURE:
<223> OTHER INFORMATION: RGD-containing peptide

<400> SEQUENCE: 7

Gly Arg Gly Asp Ser Pro Cys
1               5

<210> SEQ ID NO 8
<211> LENGTH: 7
<212> TYPE: PRT
<213> ORGANISM: Artificial Sequence
<220> FEATURE:
<223> OTHER INFORMATION: RGD-containing peptide

<400> SEQUENCE: 8

Gly Arg Gly Asp Ser Pro Lys
1               5

<210> SEQ ID NO 9
<211> LENGTH: 6
<212> TYPE: PRT
<213> ORGANISM: Artificial Sequence
<220> FEATURE:
<223> OTHER INFORMATION: RGD-containing peptide

<400> SEQUENCE: 9

Gly Arg Gly Asp Ser Cys
1               5

<210> SEQ ID NO 10
<211> LENGTH: 10
<212> TYPE: PRT
<213> ORGANISM: Artificial Sequence
<220> FEATURE:
<223> OTHER INFORMATION: RGD-containing peptide

<400> SEQUENCE: 10

Arg Gly Asp Ser Pro Ala Ser Ser Lys Pro
1               5                   10

<210> SEQ ID NO 11
<211> LENGTH: 6
<212> TYPE: PRT
<213> ORGANISM: Artificial Sequence
<220> FEATURE:
<223> OTHER INFORMATION: RGD-containing peptide

<400> SEQUENCE: 11

Gly Arg Gly Asp Asn Pro
1               5

<210> SEQ ID NO 12
<211> LENGTH: 6
<212> TYPE: PRT
```

```
<213> ORGANISM: Artificial Sequence
<220> FEATURE:
<223> OTHER INFORMATION: RGD-containing peptide

<400> SEQUENCE: 12

Gly Arg Gly Asp Thr Pro
1               5

<210> SEQ ID NO 13
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 13

Arg Gly Asp Cys
1

<210> SEQ ID NO 14
<211> LENGTH: 4
<212> TYPE: PRT
<213> ORGANISM: Artificial Sequence
<220> FEATURE:
<223> OTHER INFORMATION: RGD-containing peptide

<400> SEQUENCE: 14

Arg Gly Asp Val
1

<210> SEQ ID NO 15
<211> LENGTH: 5
<212> TYPE: PRT
<213> ORGANISM: Artificial Sequence
<220> FEATURE:
<223> OTHER INFORMATION: RGD-containing peptide

<400> SEQUENCE: 15

Asp Arg Gly Asp Ser
1               5

<210> SEQ ID NO 16
<211> LENGTH: 5
<212> TYPE: PRT
<213> ORGANISM: Artificial Sequence
<220> FEATURE:
<223> OTHER INFORMATION: RGD-containing peptide

<400> SEQUENCE: 16

Tyr Arg Gly Asp Ser
1               5

<210> SEQ ID NO 17
<211> LENGTH: 4
<212> TYPE: PRT
<213> ORGANISM: Artificial Sequence
<220> FEATURE:
<223> OTHER INFORMATION: RGD-containing peptide
<220> FEATURE:
<221> NAME/KEY: VARIANT
<222> LOCATION: 1
<223> OTHER INFORMATION: replace/ D-Arg

<400> SEQUENCE: 17

Arg Gly Asp Trp
1
```

```
<210> SEQ ID NO 18
<211> LENGTH: 7
<212> TYPE: PRT
<213> ORGANISM: Artificial Sequence
<220> FEATURE:
<223> OTHER INFORMATION: RGD-containing peptide

<400> SEQUENCE: 18

Gly Phe Arg Gly Asp Gly Gln
1               5

<210> SEQ ID NO 19
<211> LENGTH: 10
<212> TYPE: PRT
<213> ORGANISM: Artificial Sequence
<220> FEATURE:
<223> OTHER INFORMATION: RGD-containing peptide

<400> SEQUENCE: 19

Cys Arg Gly Asp Phe Pro Ala Ser Ser Cys
1               5                   10

<210> SEQ ID NO 20
<211> LENGTH: 5
<212> TYPE: PRT
<213> ORGANISM: Artificial Sequence
<220> FEATURE:
<221> NAME/KEY: BINDING
<222> LOCATION: 1..5
<223> OTHER INFORMATION: cyclo
<220> FEATURE:
<223> OTHER INFORMATION: RGD-containing peptide
<220> FEATURE:
<221> NAME/KEY: VARIANT
<222> LOCATION: 4
<223> OTHER INFORMATION: replace/ D-Phe

<400> SEQUENCE: 20

Arg Gly Asp Phe Lys
1               5

<210> SEQ ID NO 21
<211> LENGTH: 5
<212> TYPE: PRT
<213> ORGANISM: Artificial Sequence
<220> FEATURE:
<221> NAME/KEY: BINDING
<222> LOCATION: 1..5
<223> OTHER INFORMATION: cyclo
<220> FEATURE:
<223> OTHER INFORMATION: RGD-containing peptide
<220> FEATURE:
<221> NAME/KEY: VARIANT
<222> LOCATION: 4
<223> OTHER INFORMATION: replace/ D-Phe

<400> SEQUENCE: 21

Arg Gly Asp Phe Val
1               5

<210> SEQ ID NO 22
<211> LENGTH: 5
<212> TYPE: PRT
<213> ORGANISM: Artificial Sequence
<220> FEATURE:
<221> NAME/KEY: BINDING
<222> LOCATION: 1..5
<223> OTHER INFORMATION: cyclo
<220> FEATURE:
<223> OTHER INFORMATION: RGD-containing sequence
<220> FEATURE:
```

```
<221> NAME/KEY: VARIANT
<222> LOCATION: 4
<223> OTHER INFORMATION: replace/ D-Phe

<400> SEQUENCE: 22

Arg Gly Asp Phe Cys
1               5

<210> SEQ ID NO 23
<211> LENGTH: 5
<212> TYPE: PRT
<213> ORGANISM: Artificial Sequence
<220> FEATURE:
<221> NAME/KEY: BINDING
<222> LOCATION: 1..5
<223> OTHER INFORMATION: cyclo
<220> FEATURE:
<223> OTHER INFORMATION: RGD-containing peptide
<220> FEATURE:
<221> NAME/KEY: VARIANT
<222> LOCATION: 4
<223> OTHER INFORMATION: replace/ D-Tyr

<400> SEQUENCE: 23

Arg Gly Asp Tyr Lys
1               5

<210> SEQ ID NO 24
<211> LENGTH: 7
<212> TYPE: PRT
<213> ORGANISM: Artificial Sequence
<220> FEATURE:
<221> NAME/KEY: BINDING
<222> LOCATION: 1..7
<223> OTHER INFORMATION: cyclo
<220> FEATURE:
<223> OTHER INFORMATION: RGD-containing peptide

<400> SEQUENCE: 24

Gly Arg Gly Asp Ser Pro Ala
1               5

<210> SEQ ID NO 25
<211> LENGTH: 6
<212> TYPE: PRT
<213> ORGANISM: Artificial Sequence
<220> FEATURE:
<221> NAME/KEY: BINDING
<222> LOCATION: 1..6
<223> OTHER INFORMATION: cyclo
<220> FEATURE:
<223> OTHER INFORMATION: RGD-containing peptide

<400> SEQUENCE: 25

Gly Arg Gly Asp Ser Pro
1               5
```